US008217025B2

(12) United States Patent
Flores-Riveros et al.

(10) Patent No.: US 8,217,025 B2
(45) Date of Patent: Jul. 10, 2012

(54) DRUG SCREENING AND TREATMENT METHODS

(75) Inventors: Jaime Flores-Riveros, Thousand Oaks, CA (US); James M. Frincke, Carlsbad, CA (US); Christopher Reading, San Diego, CA (US); Dwight Stickney, Granite Bay, CA (US); Clarence N. Ahlem, San Diego, CA (US)

(73) Assignee: Harbor Therapeutics, Inc., San Diego, CA (US)

( * ) Notice: Subject to any disclaimer, the term of this patent is extended or adjusted under 35 U.S.C. 154(b) by 1170 days.

(21) Appl. No.: 11/942,664

(22) Filed: Nov. 19, 2007

(65) Prior Publication Data

US 2008/0146532 A1   Jun. 19, 2008

Related U.S. Application Data

(63) Continuation-in-part of application No. 11/941,934, filed on Nov. 17, 2007.

(60) Provisional application No. 60/866,395, filed on Nov. 17, 2006, provisional application No. 60/866,700, filed on Nov. 21, 2006, provisional application No. 60/868,042, filed on Nov. 30, 2006, provisional application No. 60/885,003, filed on Jan. 15, 2007, provisional application No. 60/888,058, filed on Feb. 2, 2007.

(51) Int. Cl.
*A61K 31/56* (2006.01)
(52) U.S. Cl. ..................................................... 514/178
(58) Field of Classification Search .................. None
See application file for complete search history.

(56) References Cited

U.S. PATENT DOCUMENTS

| 4,421,752 | A  | 12/1983 | Brand et al. |
| 4,898,694 | A  | 2/1990  | Schwartz et al. |
| 5,028,631 | A  | 7/1991  | Schwartz et al. |
| 5,206,008 | A  | 4/1993  | Loria |
| 5,220,006 | A  | 6/1993  | Ross et al. |
| 5,256,689 | A  | 10/1993 | Chiang |
| 5,292,730 | A  | 3/1994  | Lardy |
| 5,296,481 | A  | 3/1994  | Partridge et al. |
| 5,372,996 | A  | 12/1994 | Labrie |
| 5,387,583 | A  | 2/1995  | Loria |
| 5,424,463 | A  | 6/1995  | Lardy et al. |
| 5,461,042 | A  | 10/1995 | Loria |
| 5,506,223 | A  | 4/1996  | Lardy et al. |
| 5,527,690 | A  | 6/1996  | Goldstein et al. |
| 5,567,592 | A  | 10/1996 | Benet et al. |
| 5,593,981 | A  | 1/1997  | Labrie |
| 5,714,519 | A  | 2/1998  | Cincotta et al. |
| 5,750,519 | A  | 5/1998  | Cincotta et al. |
| 5,763,396 | A  | 6/1998  | Weiner et al. |
| 5,763,433 | A  | 6/1998  | Morfin |
| 5,804,450 | A  | 9/1998  | Karl |
| 5,859,000 | A  | 1/1999  | Dowell et al. |
| 5,859,051 | A  | 1/1999  | Adams et al. |
| 5,878,750 | A  | 3/1999  | Clemens |
| 5,912,240 | A  | 6/1999  | Loria |
| 6,028,052 | A  | 2/2000  | Heyman et al. |
| 6,054,453 | A  | 4/2000  | Lohray et al. |
| 6,110,906 | A  | 8/2000  | Labrie et al. |
| 6,147,108 | A  | 11/2000 | Hauptman |
| 6,159,966 | A  | 12/2000 | Lohray et al. |
| 6,166,049 | A  | 12/2000 | Smith |
| 6,200,998 | B1 | 3/2001  | Sahoo et al. |
| 6,214,570 | B1 | 4/2001  | Rittersdorf et al. |
| 6,303,661 | B1 | 10/2001 | Demuth et al. |
| 6,316,503 | B1 | 11/2001 | Li et al. |
| 6,329,404 | B1 | 12/2001 | Ikeda et al. |
| 6,333,340 | B1 | 12/2001 | Ross et al. |
| 6,395,767 | B2 | 5/2002  | Robl et al. |
| 6,548,261 | B1 | 4/2003  | Smith et al. |
| 6,555,126 | B2 | 4/2003  | Murad et al. |
| 6,558,906 | B2 | 5/2003  | Obokata et al. |
| 6,602,710 | B1 | 8/2003  | Chang et al. |
| 6,620,821 | B2 | 9/2003  | Robl |
| 6,631,330 | B1 | 10/2003 | Poynard |
| 6,653,064 | B1 | 11/2003 | Jochum et al. |
| 6,667,299 | B1 | 12/2003 | Ahlem et al. |
| 6,875,782 | B2 | 4/2005  | Cheng et al. |
| 6,881,581 | B2 | 4/2005  | Jones et al. |
| 6,887,712 | B1 | 5/2005  | Medford et al. |
| 6,893,830 | B1 | 5/2005  | Janowski et al. |
| 6,949,555 | B2 | 9/2005  | Guitard et al. |
| 7,462,610 | B2 | 12/2008 | Lardy et al. |
| 7,482,334 | B2 | 1/2009  | Frincke et al. |

(Continued)

FOREIGN PATENT DOCUMENTS

AU   2005/211675   10/2005

(Continued)

OTHER PUBLICATIONS

U.S. Appl. No. 60/407,146, filed Aug. 28, 2002, Ahlem et al.

(Continued)

*Primary Examiner* — Sreeni Padmanabhan
*Assistant Examiner* — Svetlana M Ivanova
(74) *Attorney, Agent, or Firm* — Daryl D Muenchau

(57) ABSTRACT

The invention relates to methods identify or characterize compounds that can be used to treat specified clinical disorders such as hyperglycemia and type 2 diabetes. Compounds that can be used in these methods include 4α-fluoro-17α-ethynylandrost-5-ene-3β,7β,17β-triol, 4α-fluoro-17α-ethynylandrost-5-ene-3β,7α,17β-triol, 4α-fluoro-17α-ethynylandrost-5-ene-3α,7β,17β-triol and 4α-fluoro-17α-ethynylandrost-5-ene-3β,17β-triol-7-one.

14 Claims, No Drawings

U.S. PATENT DOCUMENTS

| | | | |
|---|---|---|---|
| 7,524,835 | B2 | 4/2009 | Frincke |
| 7,696,189 | B1 | 4/2010 | Frincke |
| 7,776,845 | B2 | 8/2010 | Frincke |
| 7,842,680 | B2 | 11/2010 | Lardy et al. |
| 7,863,261 | B2 | 1/2011 | Frincke |
| 7,910,755 | B2 | 3/2011 | Frincke |
| 8,080,370 | B2 | 12/2011 | Matsuura et al. |
| 8,088,570 | B2 | 1/2012 | Fujimura et al. |
| 2003/0060425 | A1* | 3/2003 | Ahlem et al. ............... 514/26 |
| 2004/0097475 | A1 | 5/2004 | Wuts |
| 2004/0116359 | A1 | 6/2004 | Ahlem et al. |
| 2006/0079492 | A1 | 4/2006 | Ahlem et al. |
| 2006/0088473 | A1 | 4/2006 | Dowding et al. |
| 2006/0211059 | A1 | 9/2006 | Taneja |
| 2007/0014719 | A1 | 1/2007 | Reading et al. |
| 2007/0129282 | A1 | 6/2007 | Ahlem et al. |
| 2008/0153792 | A1 | 6/2008 | Frincke et al. |
| 2008/0153797 | A1 | 6/2008 | Frincke et al. |
| 2008/0221074 | A1 | 9/2008 | Flores-Riveros et al. |
| 2009/0143349 | A1 | 6/2009 | Lewbart et al. |
| 2010/0075937 | A1 | 3/2010 | Flores-Riveros et al. |
| 2010/0222315 | A1 | 9/2010 | Reading et al. |
| 2010/0227841 | A1 | 9/2010 | Stickney et al. |

FOREIGN PATENT DOCUMENTS

| | | |
|---|---|---|
| EP | 1 422 234 | 5/2004 |
| WO | WO 95/10527 | 4/1995 |
| WO | WO 97/17922 | 5/1997 |
| WO | WO 01/30802 | 5/2001 |
| WO | WO 00/32201 | 6/2002 |
| WO | WO 02/069977 | 9/2002 |
| WO | WO 2004/019953 | 3/2004 |
| WO | WO 2008/039566 | 4/2008 |

OTHER PUBLICATIONS

Wang et al, Amelioration of glucose intolerance by the synthetic androstene HE3286: link to inflammatory pathways, *J. Pharmacol. Exp. Ther.*, 333(1):70-80 2010.

Ahlem et al, HE3286: a novel synthetic steroid as an oral treatment for autoimmune disease, *Ann. N. Y. Acad. Sci.*, 1173:781-790 2009.

Auci et al, A new orally bioavailable synthetic androstene inhibits collagen-induced arthritis in the mouse, *Ann. N. Y. Acad. Sci.*, 1110:630-640 2007.

Chinn et al, 3-(16β,17β-dihydroxy-3-oxoandrost-4-en-17α-yl) propionic acid gamma-lactone, its preparation and antimineralocorticoid activity, *J. Med. Chem.*, 16(7):839-843 1973.

T. Rydgren et al., Efficacy of 1400W, a novel inhibitor of inducible nitric oxide synthase, in preventing interleukin-1β-induced suppression of pancreatic islet function in vitro and multiple low-dose streptozotocin-induced diabetes in vivo, *Eur. J. Endocrinology*, 147:543-551, 2002.

R.J. Johnson et al., Potential role of sugar (fructose) in the epidemic of hypertension, obesity and the metabolic syndrome, diabetes, kidney disease, and cardiovascular disease, *Am. J. Clin. Nutrition*, 86:899-906, 2007.

G.D. Barish et al., PPARδ: a dagger in the heart of the metabolic syndrome, *J. Clin. Investigation*, 116(3):590-597, 2006.

M. Mizuno et al., Renoprotective Effects of Blockade of Angiotensin II AT1 Receptors in an Animal Model of Type 2 Diabetes, *Hypertension Res.*, 25:271-278, 2002.

S.M. Schmidhuber et al., Galanin-Like Peptides Exert Potent Vasoactive Functions In Vivo, *Journal of Investigative Dermatology*, 127:716-721, 2007.

U.S. Food and Drug Administration, Guidance for Industry M3(R2) Nonclinical Safety Studies for the Conduct of Human Clinical Trials and Marketing Authorization for Pharmaceuticals, Office of Communications, Division of Drug Information, Center for Drug Evaluation and Research, Food and Drug Administration, 10903 New Hampshire Ave. Bldg. 51, Room 2201, Silver Spring, MD 20993-0002, Jan. 2010.

U.S. Food and Drug Administration, Guidance for Industry S1C(R2) Dose Selection for Carcinogenicity Studies, Office of Communications, Division of Drug Information, Center for Drug Evaluation and Research, Food and Drug Administration, 10903 New Hampshire Ave. Bldg. 51, Room 2201, Silver Spring, MD 20993-0002, Sep. 2008.

S.E. Nissen et al., Major Adverse Cardiovascular Events in Patients With Type 2 Diabetes Mellitus, *J. American Medical Assn.*, 294(20):2581-2586, 2005.

Y. Miyazaki et al., Dose-Response Effect of Pioglitazone on Insulin Sensitivity and Insulin Secretion in Type 2 Diabetes, *Diabetes Care*, 25:517-523, 2002.

H.G. Bone et al., Effects of Atorvastatin on Bone in Postmenopausal Women with Dyslipidemia: A Double-Blind, Placebo-Controlled, Dose-Ranging Trial, *Journal of Clinical Endocrinology & Metabolism*, 92(12):4671-4677, 2007.

C.Savoia et al., Vascular inflammation in hypertension and diabetes: molecular mechanisms and therapeutic interventions, *Clinical Science*, 112:375-384, 2007.

D.C. Simonson et al., Efficacy, Safety, and Dose-Response Characteristics of Glipizide Gastrointestinal Therapeutic System on Glycemic Control and Insulin Secretion in NIDDM, *Diabetes Care*, 20(4):597-606, 1997.

T. Kadowaki et al., Adiponectin and adiponectin receptors in insulin resistance, diabetes, and the metabolic syndrome, *J. Clin. Invest.*, 116:1784-1792, 2006.

E. Stein, Results of phase I/II clinical trials with ezetimibe, a novel selective cholesterol absorption inhibitor, *European Heart Journal Supplements*, 3(Supplement E):E11-E16, 2001.

P. Gaede et al., Multifactorial Intervention and Cardiovascular Disease in Patients with Type 2 Diabetes, *New Engl. J. Med.*, 348:383-93, 2003.

F.M. Gribble et al., Randomized Dose Ranging Study of the Reduction of Fasting and Postprandial Glucose in Type 2 Diabetes by Nateglinide (A-4166), *Diabetes Care*, 24:1221-1225, 2001.

K.E. Wellen et al., Inflammation, stress, and diabetes, *J. Clin. Invest.*, 115(5):1111-1119, 2005.

K.M. Figaro et al., Diabetes, Inflammation, and Functional Decline in Older Adults, *Diabetes Care*, 29:2039-2045, 2006.

H. Schmid et al., Modular Activation of Nuclear Factor-κB Transcriptional Programs in Human Diabetic Nephropathy, *Diabetes*, 55:2993-3003, 2006.

J.V. Bjornholt, et al., Fasting blood glucose: An underestimated risk factor for cardiovascular death, *Diabetes Care*, 22(1):45-49, 1999.

K.M. Gillespie, Type 1 diabetes: pathogenesis and prevention, *Canadian Medical Assn. J.*, 175(2):165-170, 2006.

K.K. Snow et al., Do age-related macular degeneration and cardiovascular disease share common antecedents?, *Ophthalmic Epidemiology*, 6(2):125-143, 1999.

F. Topouzis et al., Association of diabetes with age-related macular degeneration in the EUREYE study, *British J. Ophthamology*, 93:1037-1041, 2009.

In re Fisher, 427 F.2d 833, 166 U.S.P.Q. 18 (C.C.P.A. 1970).

H.F. Chambers et al., Can Penicillins and other β-lactam antibiotics be used to treat tuberculosis?, *Antimicrob. Agents Chemother.*, 39(12):2620-2624, 1995.

\* cited by examiner

DRUG SCREENING AND TREATMENT METHODS

CROSS REFERENCE TO RELATED APPLICATIONS

This nonprovisional U.S. patent application is a continuation-in-part of and claims priority from pending U.S. application Ser. No. 11/941,934, filed Nov. 17, 2007, and claims priority from U.S. provisional application Ser. No. 60/866,395, filed Nov. 17, 2006, U.S. provisional application Ser. No. 60/866,700, filed Nov. 21, 2006, U.S. provisional application Ser. No. 60/868,042, filed Nov. 30, 2006, U.S. provisional application Ser. No. 60/885,003, filed Jan. 15, 2007, and U.S. provisional application Ser. No. 60/888,058, filed Feb. 2, 2007, all of which are incorporated herein by reference.

FIELD OF THE INVENTION

The invention relates to methods and compounds such as 4α-fluoro-17α-ethynylandrost-5-ene-3β,7β,17β-triol to modulate inflammation, metabolic disorders and other conditions described herein. The compounds can be used to treat or slow the progression of conditions such as type 2 diabetes, hyperglycemia and insulin resistance.

BACKGROUND OF THE INVENTION

A number of factors contribute to the establishment and maintenance of many chronic autoimmune and inflammation disorders. Often, the etiology of such disorders is not well understood. Tumor necrosis factor-α (TNFα) is a cytokine that is released primarily by mononuclear phagocytes in response to a number immunostimulators. When administered to animals or humans, it causes inflammation, fever, cardiovascular effects, hemorrhage, coagulation, and acute phase responses similar to those seen during acute infections and shock states. Excessive or unregulated TNFα production is thus implicated in a number of disease conditions. These include endotoxemia and/or toxic shock syndrome, e.g., Tracey et al., *Nature* 330:662-664 (1987) and Hinshaw et al., *Circ. Shock* 30:279-292 (1990), cachexia, e.g., Dezube et al., *Lancet,* 335(8690):662 (1990) and ARDS where high TNFα concentrations have been detected in pulmonary aspirates from ARDS patients, e.g., Millar et al., *Lancet* 2(8665):712-714 (1989).

TNFα also may be involved in bone resorption diseases, including arthritis. When activated, leukocytes can produce bone-resorption, an activity to which TNFα may contribute, e.g., Bertolini et al., *Nature* 319:516-518 (1986) and Johnson et al., *Endocrinology* 124(3):1424-1427 (1989). TNFα also has been shown to stimulate bone resorption and inhibit bone formation in vitro and in vivo through stimulation of osteoclast formation and activation combined with inhibition of osteoblast function. Blocking TNFα with monoclonal anti-TNFα antibodies has been shown to be beneficial in rheumatoid arthritis (Elliot et al., *Int. J. Pharmac.* 17(2):141-145 1995) and Crohn's disease (von Dullemen et al., *Gastroenterology,* 109(1):129-135 2005).

The nuclear factor-kappaB (NF-κB) molecule is a mediator of inflammation in a number of clinical conditions. Some therapeutic agents that are used to treat inflammation such as dexamethasone, prednisone or hydrocortisol are glucocorticoid receptor (GR) agonists and they indirectly inhibit NF-κB by increasing the activity of the GR, e.g., H. Harkonarson et al., *Am. J. Respir. Cell Mol. Biol.* 25:761-771, 2001. However, elevated levels of natural GR agonists and pharmacological levels of synthetic GR agonists usually exert unwanted toxicities including significant immune suppression and loss of bone mass or osteopenia, e.g., T. L. Popper et al., *Anti-inflammatory agents: Anti-inflammatory steroids,* R A. Scherer & M. W. Whitehouse, editors, Academic Press, New York, Chapter 9, volume 1, pages 245-294, 1974. Many of the unwanted toxicities associated with glucocorticoids are caused by activation of the GR. Thus, Identification of compounds that can inhibit NF-κB activity without causing these toxicities by activating the GR represents a class of agents that could be used to treat inflammation and associated symptoms such as pain, fever or fatigue.

Unwanted or damaging inflammation occurs in a number of chronic or acute conditions, e.g., ARDS, COPD and sepsis. Activated monocytes and neutrophils may play a role in mediating inflammation associated pathology in some of these conditions. Activated neutrophils can have increased NFκ-B in the nucleus and increased production of proinflammatory cytokines. Neutrophils can be a source of toxic oxygen species whose generation mediates, at least in part, tumor necrosis factor-alpha (TNF-α) secretion by activated macrophages. TNFα may be necessary for some of the organ injury and failure that can be seen in sepsis.

Signaling associated with inflammation can occur through different pathways and this can increase the activity of NF-κB in affected cells. NF-κB activation by tumor necrosis factor-α (TNF-α) starts with binding of TNF-α to the TNF-α receptor at the cell membrane, followed by activation of a series on signal transducers including MAP kinases. Activation of NF-κB in the cytoplasm leads to its translocation into the nucleus and activation of genes that contain the NF-κB response element in their promoters. Activation of cytoplasmic NF-κB by bacterial lipopolysaccharide (LPS) begins with binding of LPS to Toll-like receptor 4 at the cell surface and subsequent activation of intracellular signal transducers, including phosphatidylinositol-3-kinase. TNF-α and LPS are both known to induce intense inflammatory responses in vivo and in cells in vitro. Cells that respond to such proinflammatory signals include macrophages, monocytes and other types of immune cells.

Various T cell subsets appear to have a role in the development of certain disease conditions. An important role for a distinct T cell populations including regulatory and/or suppressor T cells in mediating various aspects of immunity has been suggested, e.g., E. Suri-Payer et al., *J. Immunol.,* 160(3): 1212-1218, 1998; J. Shimizu et al., *J. Immunol.,* 163(10): 5211-5218, 1999; M. Itoh et al., *J. Immunol.,* 162(9):5317-5326, 1999; A. M. Miller et al., *J. Immunol.,* 177:7398-7405, 2006. $CD4^+$ $CD25^+$ T cells may play a role in suppressing some immune responses.

Study of some of these T cell subsets in animal models have been described, e.g., U.S. Pat. No. 6,593,511. For example, a role for the study of human autoimmune conditions was examined in the scid/scid $CD4^+$ $CD45Rb^{hi}$ model. This animal model has been used to study dysregulated immune responses such as inflammation conditions and to evaluate experimental drugs and treatment protocols, e.g., K. Hong et al., *J. Immunol.,* 162:7480-7491, 1999; Powrie et al., *J. Exp. Med.,* 183(6):2669-2674, 1996.

The Foxpro3 gene, which is induced by thymus epithelium may play a role in inducing T cells to develop the $CD4^+$ $CD25^+$ or $CD4^+CD25^{high}$ (Treg or regulator T cell) phenotype. The CD25 surface antigen is the IL-2 receptor α-chain. In some animal models of autoimmune diseases, deficiency of the Foxpro3 gene is associated with the occurrence of autoimmune diseases, e.g., U.S. patent application No. 2006/0111316. Restoration of this gene appears to reduce autoimmune anomalies. Various reagents or assay protocols for $CD4^+CD25^+$ cells have been described, e.g., H. Yagi et al., *International Immunol.*, 16(11):1643-1656, 2004; W. R. Godfrey et al., *Blood*, 105(2)750-758, 2005.

Insulin resistance in glucose intolerant subjects has long been recognized. Reaven et al (*American Journal of Medicine*, 60(1):80-88, 1976) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been described by experimental, clinical and epidemiological studies (Stout, *Metabolism*, 34:7, 1985; Pyorala et al, *Diabetes/Metabolism Reviews*, 3:463, 1987). Statistically significant plasma insulin elevations at 1 and 2 hours after oral glucose load correlate with an increased risk of coronary heart disease.

One model of human diabetes is the db/db mouse. The db/db mouse model has been described, e.g., D. Koya et al., *The FASEB Journal*, 14:439-447, 2000; K. Kobayashi et al., *Metabolism*, 49(1): 22-31, 2000; J. Berger et al., *J. Biol. Chem.*, 274(10):6718-6725, 1999. The db/db mice carry a mutation in the gene encoding the leptin receptor, which confers a phenotype characterized by hyperphagia, obesity, insulin resistance and diabetes as their functional pancreatic β-cell mass deteriorates over time, particularly for animals in the C57BL/Ks genetic background. The db/db mice typically become identifiably obese at around 3 to 4 weeks of age and elevations of plasma insulin begin at 10 to 14 days. Elevations of blood sugar are seen at 4 to 8 weeks of age with an uncontrolled rise in blood sugar, severe depletion of the insulin producing β-cells of the pancreatic islets, and death by about 10 months of age. This model has been used to characterize the capacity of drug candidates to affect the onset or rate of progression of parameters, e.g., hyperglycemia and weight gain, related to the development and maintenance of diabetes.

Treatment of diabetes with PPAR-γ agonists has been associated with cardiac hypertrophy, or an increase in heart weight. Treatment with rosiglitazone maleate, a PPAR-γ agonist, indicate that patients may experience fluid accumulation and volume-related events such as edema and congestive heart failure. Cardiac hypertrophy related to PPAR-γ agonist treatment is typically treated by discontinuing the treatment.

A physiological effect of cortisol is its antagonism to insulin. High cortisol concentrations in the liver can reduce insulin sensitivity in that organ, which tends to increase gluconeogenesis and increase blood sugar levels (M. F. Dallman et al. Front Neuroendocrinol., 14:303-347, 1993). This effect aggravates impaired glucose tolerance or diabetes mellitus. In Cushing's syndrome, which is caused by excessive circulating concentrations of cortisol, the antagonism of insulin can provoke diabetes mellitus in susceptible individuals (E. J. Ross et al., Lancet, 2:646-649, 1982).

Cortisol can be converted in the body to cortisone by the 11b-dehydrogenase activity of 11b-hydroxysteroid dehydrogenase enzymes. The reverse reaction, converting inactive cortisone to active cortisol, is accomplished in certain organs by the 11b-reductase activity of these enzymes. This activity is also known as corticosteroid 11b-reductase activity. There are at least two distinct isozymes of 11β-hydroxysteroid dehydrogenase. Expression of 11β-HSD type 1 in a range of cell lines generates either a bi-directional enzyme or a predominant 11β-reductase, which can regenerate 11β-hydroxysteroid from the otherwise inert 11-keto steroid parent.

Mitochondrial phosphoenolpyruvate carboxykinase (also known as PEPCK-mitochondrial, PEPCK-M, PCK2 and mtPEPCK) is expressed in a variety of human tissues, mainly the liver, kidney, pancreas, intestine and fibroblasts (Modaressi et al., Biochem. J., 333:359-366, 1998). PEPCK-mitochondrial deficiency, while not well documented, has been associated with failure to thrive, hypoglycemia and liver abnormalities. Unlike the cytosolic form (PEPCK-C), the mitochondrial form (PEPCK-mitochondrial) is expressed constitutively and is not regulated by hormonal stimuli (Hanson and Patel, Adv. Enzymol. Relat. Areas Mol. Biol., 69:203-281, 1994). The two forms are located on separate chromosomes with localized to chromosome 14q11 and PEPCK-C resides on chromosome 20q11 (Stoffel et al., Hum. Mol. Genet. 2:1-4, 1993).

Multiple sclerosis (MS) is an autoimmune disease that is an inflammatory disease of the central nervous system (Bar-Or, A., *J. Neuroimmunol.* 100:252-259, 1999). Although the natural course of the disease has recently been improved by treatment with immunomodulatory-immunosuppressive compounds such as Interferon (IFN)-beta, copolymer, cyclophosphamide and mitoxantrone (Hafler, D. A. and Weiner, H. L., *Immunological Reviews* 144:75, 1995; Goodkin, D. E., *Lancet* 352: 1486, 1998), none of these drugs can block progression of disease and some of them have serious side-effects that limit their prolonged use. In addition, a substantial number of patients with both relapsing-remitting and secondary progressive MS exhibit poor response to IFN-β. Therefore, there is a need for novel compounds that alone or in combination therapy improve the course of MS by e.g., slowing its progression.

There is a current need for cost-effective pharmaceutical agents or treatment methods that are more effective in treating conditions described herein. The present invention provides therapeutic agents and treatment methods to treat one or more of the conditions described herein. The claimed agents and methods are useful to reduce one or more symptoms associated with the conditions described herein. Also, the use of the invention agents and methods can be combined with one or more conventional treatments for these disorders.

DESCRIPTION OF THE INVENTION

Summary of Invention Embodiments

Invention embodiments include a method to identify a compound with a potential to treat or ameliorate a metabolic disorder in a mammal, comprising selecting a compound that; (i) does not activate one, two or three of PPAR-α, PPAR-γ and PPAR-δ in human or mammalian cells in vitro by more than about 30% when compared to suitable negative control human or mammalian cells in vitro; (ii) inhibits or decreases the transcriptional activity or level of NF-κB by about 20-80% in human or mammalian cells in vitro when compared to suitable negative control human or mammalian cells in vitro; (iii) when compared to a suitable negative control or normal control, (a) decreases the degree of hyperglycemia, (b) slows the progression of hyperglycemia, (c) delays the onset of hyperglycemia, (d) decreases the rate of macular degeneration, (e) delays the onset of macular degeneration, (f) decreases the occurrence or incidence of vascular ulcers, (g) decreases the severity of vascular ulcers, (h) increases insulin sensitivity, (i) decreases glucose intolerance, (j) slows the progression or rate of loss of pancreatic β-islet cell numbers or their capacity to secrete insulin, (k) increases pancreatic β-islet cell numbers or their capacity to secrete insulin, (l) slows the rate of weight increase in db/db mice or mice with diet induced obesity, (m) decreases elevated levels of triglycerides, (n) decreases elevated levels total blood or serum cholesterol, (o) decreases normal or elevated levels of LDL, VLDL, apoB-100 or apoB-48 in blood or serum, (p) increases normal or low levels of HDL or apoA1 in blood or serum, (q) decreases or normalizes an elevated level of a phase reactive protein, optionally C reactive protein or fibrinogen in blood or serum, (r) decreases or normalizes hemoglobin $A_{1C}$, (s) decreases or normalizes fasting blood glucose levels, (t) normalizes serum or blood glucose in an oral glucose tolerance test, (u) normalizes serum or blood glucose in a 2 hour post prandial glucose test or (v) increases whole body or tissue glucose disposal or uptake in a human or another mammal in vivo, for 1, 2 or 3 of the foregoing; (iv) optionally, does not activate one or more of a glucocorticoid receptor, an androgen receptor an estrogen receptor-α, estrogen receptor-β or a biologically active variant of any of these biomolecules in human or mammalian cells in vitro by more than about 30% when compared to suitable negative control human or mammalian cells in vitro; and (v) optionally inhibits the level or activity of phosphoenolpyruvate carboxykinase (PEPCK) or a 11β-hydroxysteroid dehydrogenase (11β-HSD), optionally 11β-HSD type 1 or 11β-HSD type 2 or the level of a mRNA that encodes PEPCK or a 11β-HSD, in hepatocytes or liver-derived cells in vitro or in liver cells or tissue obtained from liver cells or tissue in vivo; optionally whereby the compound with a potential to treat or ameliorate the metabolic disorder in a mammal is identified and optionally recorded as such in a written or a readable electronic medium. In some embodiments, the compound accomplishes one or two of, e.g., a decrease in the degree of hyperglycemia, improves insulin resistance, a decrease or normalization of fasting blood glucose levels, e.g., in obese, diabetic or pre-diabetic patients or subjects, an increase in whole body or tissue glucose disposal or uptake, e.g., in a rodent or human or amelioration of diabetes as observed by improvement in one or more symptoms associated with type 2 diabetes or a hyperlipidemia condition described herein.

In other embodiments, the invention provides a method to treat a pulmonary condition, e.g., such as asthma, cystic fibrosis, lung fibrosis, acute respiratory distress syndrome (ARDS) or chronic obstructive pulmonary disease (COPD), in a mammal having the pulmonary condition comprising administering an effective amount of a compound having the structure

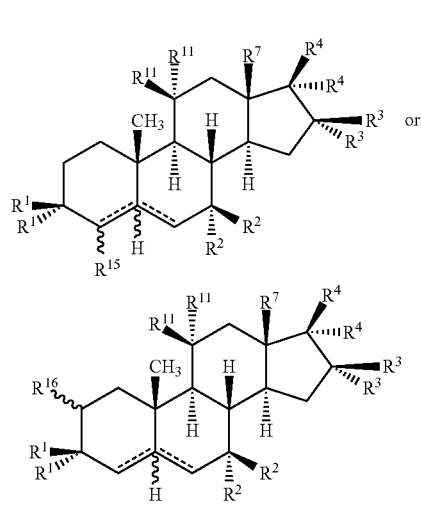

wherein the dotted lines are an optional double bond and if one is present, the hydrogen atom at the 5-position is absent, or hydrogen is present in the α- or β-configuration; wherein one $R^1$ is —H or $C_{1-8}$ optionally substituted alkyl and the other $R^1$ is —OH, an ester or an ether; one $R^2$ is —H or $C_{1-8}$ optionally substituted alkyl and the other $R^2$ is —OH or an ester, or both $R^2$ together are =O; one $R^3$ is —H and the other $R^3$ is —H, —OH, an ester or an ether; $R^4$ in the α-configuration is optionally substituted alkynyl such as optionally substituted $C_{2-4}$ alkynyl; $R^4$ in the β-configuration is —OH or an ester; $R^7$ is —CH$_3$, —C$_2$H$_5$ or —CH$_2$OH; one $R^{11}$ is —H or $C_{1-8}$ optionally substituted alkyl and the other $R^{11}$ is —H, —OH or an ester, or both $R^{11}$ together are =O or =NOH; $R^{15}$ is —H, —OH, halogen, an ester or an ether in the α-configuration or the β-configuration or =O if no double bond is present at the 4-5 position or $R^{15}$ is —H, an ester or an ether if a double bond is present at the 4-5 position; and $R^{16}$ is —H, —OH, an ester or an ether in the α-configuration or the β-configuration or =O or =NOH.

The invention provides compounds or compositions to treat, prevent, slow the progression of or ameliorate an unwanted inflammation condition an autoimmune disease or a metabolic disorder or a symptom thereof, in a mammal in need thereof, optionally wherein the mammal is a human or a non-human primate, optionally wherein the compositions comprise a formula 1 compound ("F1C") having the structure

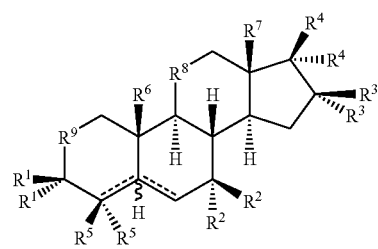

wherein, the dotted lines are optional double bonds, one $R^1$ is —H or a carbon-linked moiety such as optionally substituted alkyl and the other $R^1$ is an oxygen-linked moiety, a sulfur-linked moiety or a nitrogen-linked moiety, or both $R^1$ together are =O, =NOH or =NO—$C_{1-6}$ alkyl; one $R^2$ is —H or a carbon-linked moiety such as optionally substituted alkyl and the other $R^2$ is —H, an oxygen-linked moiety, a sulfur-linked moiety or a nitrogen-linked moiety, or both $R^2$ together are =O; one $R^3$ is —H or a carbon-linked moiety such as optionally substituted alkyl and the other $R^3$ is —H, an oxygen-linked moiety, a sulfur-linked moiety or a nitrogen-linked moiety; one $R^4$ is —H or a carbon-linked moiety such as optionally substituted alkyl and the other $R^4$ is an oxygen-linked moiety, a sulfur-linked moiety or a nitrogen-linked moiety, or both $R^4$ together are =O, =NOH or =NO—$C_{1-6}$ alkyl; one $R^5$ is —H or a carbon-linked moiety such as optionally substituted alkyl and the other $R^5$ is —H, an oxygen-linked moiety, a sulfur-linked moiety or a nitrogen-linked moiety; $R^6$ is —H or $C_{1-6}$ optionally substituted alkyl, optionally —$CH_3$; and $R^7$ is —H or $C_{1-6}$ optionally substituted alkyl, optionally —$CH_3$, —$CH_2OH$ or —$C_2H_5$; $R^8$ is —$CH_2$—, or —$C(R^{10})_2$— where $R^{10}$ independently or together are —H, =O, a carbon-linked moiety such as optionally substituted alkyl, an oxygen-linked moiety, optionally —OH or an ester or ether optionally selected from —OC(O)—$CH_3$, —OC(O)—$C_2H_5$, —$OCH_3$ and —$OC_2H_5$, a sulfur-linked moiety or a nitrogen-linked moiety; and $R^9$ is —$CH_2$—, or —$C(R^{10})_2$— where $R^{10}$ independently or together are —H, halogen, =O, a carbon-linked moiety such as optionally substituted alkyl, an oxygen-linked moiety, optionally —OH or an ester or ether optionally selected from —OC(O)—$CH_3$, —OC(O)—$C_2H_5$, —$OCH_3$ and —$OC_2H_5$, a sulfur-linked moiety or a nitrogen-linked moiety.

The invention also provides a method to identify or characterize a biological activity of a compound with a potential to treat or ameliorate a metabolic disorder in a mammal, comprising selecting a compound that (i) does not activate one, two or three of PPAR-α, PPAR-γ and PPAR-δ in human or mammalian cells in vitro by more than about 30% when compared to suitable negative control human or mammalian cells in vitro; (ii) inhibits or decreases the transcriptional activity or level of NF-κB by about 20-80% in human or mammalian cells in vitro when compared to suitable negative control human or mammalian cells in vitro; (iii) when compared to a suitable negative control or normal control, decreases hyperglycemia, slows the progression or delays the onset of hyperglycemia, increases insulin sensitivity, decreases glucose intolerance, slows the progression or rate of loss of pancreatic β-islet cell numbers or their capacity to secrete insulin, increases pancreatic β-islet cell numbers or their capacity to secrete insulin, slows the rate of weight increase in db/db mice or in subjects with diet induced or diet related obesity, decreases elevated levels of triglycerides, decreases elevated levels total blood or serum cholesterol, decreases normal or elevated levels of LDL, VLDL, apoB-100 or apoB-48 in blood or serum or increases normal or low levels of HDL or apoA1 in blood or serum or decreases an elevated level of fibrinogen in blood or serum; and (iv) optionally, does not activate one or more of a glucocorticoid receptor, a mineralcorticoid receptor, a progesterone receptor, an androgen receptor an estrogen receptor-α, estrogen receptor-β or a biologically active variant of any of these biomolecules in human or mammalian cells in vitro by more than about 30% when compared to suitable negative control human or mammalian cells in vitro. The method allows identification or characterization of the compound as having a potential to treat or ameliorate the metabolic disorder in human or another mammal.

Embodiments also include compositions comprising a formula 1 compound for the prophylaxis or treatment of an autoimmune condition, an unwanted inflammation condition or a metabolic disorder or a symptom of any of these conditions.

Other embodiments are as described elsewhere in the specification including the embodiments described herein.

DEFINITIONS

As used herein and unless otherwise stated or implied by context, terms that are used herein have the meanings that are defined here. The descriptions of embodiments and examples that are described illustrate the invention and they are not intended to limit it in any way. Unless otherwise contraindicated or implied, e.g., by including mutually exclusive elements or options, in these definitions and throughout this specification, the terms "a" and "an" mean one or more and the term "or" means and/or.

The phrase "metabolic disorder" or "metabolic disease" means one or more conditions such as type 1 diabetes, type 2 diabetes, obesity, insulin resistance, hyperglycemia, impaired glucose utilization or tolerance, impaired or reduced insulin synthesis, a hyperlipidemia condition such as hypercholesterolemia, hypertriglyceridemia or elevated free fatty acids and hypolipidemia conditions. Hypercholesterolemias include hyper-LDL cholesterolemia or elevated LDL cholesterol. Hypolipidemias include hypo-HDL cholesterolemia or low HDL cholesterol levels. Type 1 diabetes includes Immune-Mediated Diabetes Mellitus and Idiopathic Diabetes Mellitus. Type 2 diabetes includes forms with predominant or profound insulin resistance, predominant insulin deficiency and some insulin resistance and forms intermediate between these. Other descriptions are elsewhere herein.

A "formulation" or the like means a composition that one can administer to a subject, e.g., human or animal. Formulations are suitable for human or veterinary applications and would typically have expected characteristics for the formulation, e.g., parenteral formulations for human use would usually be sterile solutions or suspensions.

An "excipient", "carrier", "pharmaceutically acceptable carrier" or similar terms mean one or more component(s) or ingredient(s) that is acceptable in the sense of being compatible with the other ingredients of invention compositions or formulations and not overly deleterious to the patient, animal, tissues or cells to which the formulation is to be administered.

A "subject" means a human or animal. Usually the animal is a mammal or such as a non-human primate, rodent, lagomorph, domestic animal or game animal. Primates include chimpanzees, cynomologus monkeys, spider monkeys, and macaques, e.g., Rhesus or Pan. Rodents and lagomorphs include mice, rats, woodchucks, ferrets, rabbits and hamsters.

"Alkyl" as used here means linked normal, secondary, tertiary or cyclic carbon atoms, i.e., linear, branched, cyclic or any combination thereof. Alkyl moieties, as used herein, may be saturated, or unsaturated, i.e., the moiety may comprise one, two or more independently selected double bonds or triple bonds. Unsaturated alkyl moieties include moieties as described for alkenyl and alkynyl moieties described below. The number of carbon atoms in an alkyl group or moiety is 1 to about 30, e.g., about 1-20 or about 1-8, unless otherwise specified. Thus $C_{1-8}$ alkyl means an alkyl moiety containing 1, 2, 3, 4, 5, 6, 7 or 8 carbon atoms. When an alkyl group is specified, species may include methyl, ethyl, 1-propyl (n-propyl), 2-propyl (i-propyl, —CH($CH_3$)$_2$), 1-butyl (n-butyl), 2-methyl-1-propyl (i-butyl, —$CH_2CH(CH_3)_2$), 2-butyl (s-butyl, —CH($CH_3$)$CH_2CH_3$), 2-methyl-2-propyl (t-butyl, —C($CH_3$)$_3$), —$(CH_2)_n$—$(CHCH_3)_m$—$(CH_2)_o$—$CH_3$ and —$(CH_2)_n$—$(CHC_2H_5)_m$—$(CH_2)_o$—$CH_3$ where n, m and o independently are 0, 1, 2, 3, 4, 5, 6, 7 or 8.

"Alkenyl" as used here means a moiety that comprises linked normal, secondary, tertiary or cyclic carbon atoms, i.e., linear, branched, cyclic or any combination thereof, that comprises one or more double bonds (e.g., —CH═CH—), e.g., 1, 2, 3, 4, 5, 6 or more, typically 1 or 2. The number of carbon atoms in an alkenyl group or moiety is 2 to about 30, e.g., about 2-20 or about 2-8, unless otherwise specified, e.g., $C_{2-8}$ alkenyl or C2-8 alkenyl means an alkenyl moiety containing 2, 3, 4, 5, 6, 7 or 8 carbon atoms. When an alkenyl group is specified, species may include vinyl, allyl, —(CH$_2$)$_n$—(CH═CH)—(CH$_2$)$_m$—CH$_3$, —(CH$_2$)$_n$—(CCH$_3$═CH)—(CH$_2$)$_m$—CH$_3$, —(CH$_2$)$_n$—(CH═CCH$_3$)—(CH$_2$)$_m$—CH$_3$ and —(CH$_2$)$_n$—(CH═CH)$_{0-1}$—(CH$_2$)$_m$—CH$_2$CH═CH$_2$, where n and m independently are 0, 1, 2, 3, 4, 5, 6, 7 or 8.

"Alkynyl" as used here means a moiety that comprises linked normal, secondary, tertiary or cyclic carbon atoms, i.e., linear, branched, cyclic or any combination thereof, that comprises one or more triple bonds (—C≡C—), e.g., 1, 2, 3, 4, 5, 6 or more, typically 1 or 2 triple bonds, optionally comprising 1, 2, 3, 4, 5, 6 or more double bonds, with the remaining bonds being single bonds. The number of carbon atoms in an alkenyl group or moiety is 2 to about 30, e.g., about 2-20 or about 2-8, unless otherwise specified, e.g., $C_{2-8}$ alkynyl or $C_{2-8}$ alkynyl means an alkynyl moiety containing 2, 3, 4, 5, 6, 7 or 8 carbon atoms. When an alkynyl group is specified, groups and species may include —CCH, —CCCH$_3$, —CCCH$_2$CH$_3$, —CCC$_3$H$_7$, —CCCH$_2$C$_3$H$_7$, —(CH$_2$)$_n$—(C≡C)—(CH$_2$)$_m$—CH$_3$, and —(CH$_2$)$_n$—(C≡C)$_{0-1}$—(CH$_2$)$_m$—CH$_2$C≡CH, where n and m independently are 0, 1, 2, 3, 4, 5, 6, 7 or 8.

"Substituted alkyl", "substituted alkenyl" "substituted alkynyl" and the like mean an alkyl, alkenyl, alkynyl or another group or moiety as defined herein that has a substituent(s) or that comprises a substituent(s) that replaces a hydrogen atom(s) and is bonded to a carbon atom(s) or a substituent (s) that interrupts a carbon atom chain. Substituents include 1, 2, 3, 4, 5, 6 or more independently selected —F, —Cl, —Br, —I, —OH, —OR$^{PR}$, —SH, —SCH$_3$, —O—, —S—, —NH—, —C(O)—, —C(O)OR$^{PR}$, —CHO, —CH$_2$SH, —C═N—, —C(O)OR$^{PR}$, —C(O)CH$_3$, where R$^{PR}$ independently is hydrogen or a protecting group. Exemplary substituted alkyl or substituted alkenyl moieties are —CCCl, —CH$_2$OH, —CF$_3$ and —CH$_2$(OH)CH$_3$.

"Halogen" means fluorine, chlorine, bromine or iodine.

"Ester" means a moiety that comprises a —C(O)—O— structure. Typically, esters as used here comprise an organic moiety containing about 1-50 carbon atoms, usually about 2-20 or 2-8 carbon atoms and 0 to about 10 independently selected heteroatoms (e.g., O, S, N, P, Si), where the organic moiety is bonded to a formula 1 steroid nucleus at, e.g., R$^1$ or R$^2$ through the —C(O)—O— structure, e.g., organic moiety-C(O)—O-steroid or organic moiety-O—C(O)-steroid. The organic moiety usually comprises one or more of any of the organic groups described above, e.g., $C_{1-8}$ alkyl moieties, $C_{2-8}$ alkenyl moieties, $C_{2-8}$ alkynyl moieties, aryl moieties, $C_{2-9}$ heterocycles or substituted derivatives of any of these, e.g., comprising 1, 2, 3, 4 or more substituents, where each substituent is independently chosen. Esters include esters of succinic acid, dicarboxylic acids and amino acids such as —C(O)—(CH$_2$)$_n$—C(O)—OR$^{PR}$, —O—C(O)—(CH$_2$)$_n$—NHR$^{PR}$, —NH—(CH$_2$)$_n$—C(O)—OR$^{PR}$, where n is 1, 2, 3, 4, 5, 6, 7 or 8 and R$^{PR}$ is —H or a protecting group such as C1-4 alkyl. Esters also include structures such as —O—C(O)—O—(CH$_2$)$_n$—H and —O—C(O)—NH—(CH$_2$)$_n$—H.

Exemplary esters include one or more independently selected acetate, enanthate, propionate, isopropionate, cyclopropionate, isobutyrate, n-butyrate, valerate, caproate, isocaproate, hexanoate, heptanoate, octanoate, nonanoate, decanoate, undecanoate, phenylacetate or benzoate, which are typically hydroxyl esters. Esters also include amino acids, carbonates and carbamates including —O—C(O)—CH$_2$—NHR$^{PR}$, —O—C(O)—CH$_2$CH$_2$—NHR$^{PR}$, —O—C(O)—CH(CH$_3$)—NHR$^{PR}$, —O—C(O)—CH$_2$CH(CH$_3$)—NHR$^{PR}$, —O—C(O)—CH(NHR$^{PR}$)—CH(OR$^{PR}$)—CH$_3$, —O—C(O)—O—(CH$_2$)$_m$—H and —O—C(O)—NH—(CH$_2$)$_m$—H where R$^{PR}$ is —H or a protecting group such as $C_{1-4}$ alkyl (—CH$_3$, —C$_2$H$_5$, —C$_3$H$_7$, etc.) or —C(O)—CH$_3$ or —CH$_2$CH$_2$—O—CH$_3$ and m is 0, 1, 2, 3, 4, 5 or 6. Esters also include —O—C(O)—(CF$_2$)$_n$—CF$_3$, —O—C(O)—(CH$_2$)$_n$—CH$_3$, —O—C(O)—CH(CH$_3$)—(CH$_2$)$_n$—CH$_3$ and —O—C(O)—C(CH$_3$)$_2$—(CH$_2$)$_n$—CH$_3$ where n is 0, 1, 2, 3, 4, 5 or 6.

Preferred esters are —OC(O)CH$_3$, —OC(O)C$_2$H$_5$, —OC(O)—(CH$_2$)$_2$—CH$_3$, —OC(O)—(CH$_2$)$_4$—CH$_3$, —OC(O)—(CH$_2$)$_{10}$—CH$_3$, —OC(O)—(CH$_2$)$_{14}$—CH$_3$, —OC(O)—(CH$_2$)$_{16}$—CH$_3$, —OC(O)(CH$_2$)$_7$CH═CH—(CH$_2$)$_7$CH$_3$, with —OC(O)CH$_3$ and —OC(O)C$_2$H$_5$ usually being most preferred.

"Ether" means an organic moiety as described for ester that comprises 1, 2, 3, 4 or more —O— moieties, usually 1 or 2. In some embodiments, the —O— group is linked to the steroid nucleus at a variable group such as R$^1$, R$^2$, R$^3$, R$^4$ or R$^{11}$, e.g., organic moiety-O-steroid. The organic moiety is as described above for esters. Ethers include —O—(CH$_2$)$_n$—CH$_3$, —O—CH$_2$(CH$_2$)$_n$—O—CH$_3$, —O—CH$_2$(CH$_2$)$_n$—S—CH$_3$ and —O—CH(CH$_3$)—(CH$_2$)$_n$—CH$_3$ where n is 0, 1, 2, 3, 4, 5 or 6.

Formula 1 compounds. In some embodiments, the formula 1 compounds have 3, 4 or 5 hydroxy groups, optionally wherein one, two or more are esterified with ester groups that are the same or different. In preferred embodiments, the 17-position is disubstituted with an oxygen linked moiety such as —OH, ester or ether and either —H or a carbon linked moiety, preferably optionally substituted $C_{2-4}$ alkynyl, preferably —CCH or —CC—Cl. In some of these embodiments the hydroxyl groups or esters are at the 3-, 4-, 16-, and 17-positions wherein the hydroxyl groups or esters at the 3-, 4- and 16-positions respectively are in the β,β,α, β,β,β, α,β,α, α,β, β, β,α,α, β,α,β, α,α,α or α,α,β, configurations. The hydroxyl or ester at the 17-position is typically in the β-configuration, but can be in the α-configuration. R$^{10}$ in these compounds is typically —H or a halogen such as —F and R$^5$ optionally is —CH$_3$ or —C$_2$H$_5$ and R$^6$ optionally is —H or —CH$_3$. For some of these compounds an additional hydroxyl or ester can be present at the 7-position or the 11-position in the β-configuration or the α-configuration.

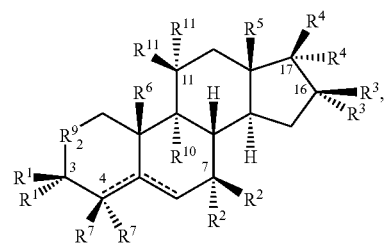

F1C structures include
wherein one R$^1$ is —H or optionally substituted alkyl and the other R$^1$ is —H, —OH, an ester or an ether, or both R$^1$ together are ═O or an oxime such as ═NOH or ═NOCH$_3$; an ester or an ether; one R$^2$ is —H or optionally substituted alkyl and the other R$^2$ is —H, —OH, an ester or an ether or both R$^2$ together are ═O or an oxime such as ═NOH or =NOCH₃; one R³ is —H or optionally substituted alkyl and the other R³ is —H, —OH, an ester or an ether or optionally substituted alkyl or both R³ together are =O or an oxime such as =NOH or =NOCH₃; one R⁴ is —H or optionally substituted alkyl and the other R⁴ is —OH, an ester or an ether or both R⁴ together are or both R⁴ together are =O or an oxime such as =NOH or =NOCH₃; R⁵ is optionally substituted alkyl, optionally selected from —CH₃, —C₂H₅ and —CH₂OH; R⁶ is —H or optionally substituted alkyl, optionally selected from —CH₃, —C₂H₅ and —CH₂OH; one R⁷ is —H or optionally substituted alkyl and the other R⁷ is —H, —OH, an ester or an ether or, when no double bond is present at the 4-position both R⁷ together are =O or an oxime such as =NOH or =NOCH₃; R⁹ is —O— or —C(R¹²)(R¹²)— where one R¹² is —H, —F, —Br or optionally substituted alkyl and the other R¹² is —H, —OH, an ester or an ether or optionally substituted alkyl or both R¹² together are =O or an oxime such as =NOH or =NOCH₃; R¹⁰ is —H or a halogen such as —F or —Cl; and one R¹¹ is —H or optionally substituted alkyl and the other R¹¹ is —H, —OH, an ester or an ether or optionally substituted alkyl or both R¹¹ together are =O or an oxime such as =NOH or =NOCH₃. Embodiments of these compounds include compounds wherein (i) one, two or three of R², R⁷, R¹¹ and R¹² independently are —OH, a C₂₋₈ ester, a C₁₋₈ ether or =O, (ii) one or two of R¹, R⁷, R¹¹ and R¹² are —OH, a C₂₋₈ ester or a C₁₋₈ ether and (iii) one or two of R¹, R², R⁷, R¹¹ and R¹² are =O or =NOH and one, two or three of the others independently are —OH, a C₂₋₈ ester or a C₁₋₈ ether. The hydrogen atom at the 5-position, when present, can be in the α- or β-configuration. When a double bond is present at the 4-position, one R⁷ moiety is absent.

For formula 1 compounds C₁₋₈ substituted alkyl moieties usually include —CH₂F, —CF₃, —CH₂OH and —C₂F₅. C₂₋₄ optionally substituted alkynyl moieties usually include —CCH, —CCCl, —CCCH₃, —CCCH₂OH, —CCCH₂Cl and —CCCH₂Br.

Exemplary formula 1 compounds include 17α-ethynylandrost-5-ene-3β,4β,7β,16α,17β-pentol and epimers of this compound where one or two hydroxyl groups are epimerized, e.g., 17α-ethynylandrost-5-ene-3α,4β,7β,16α,17β-pentol, 17α-ethynylandrost-5-ene-3β,4α,7α,16α,17β-pentol and 17α-ethynylandrost-5-ene-3β,4β,7α,16β,17β-pentol. Other formula 1 compounds include ones where 5 independently selected —OH, ester or ether moieties are present, e.g., 17α-ethynylandrost-5-ene-3β,4β,11β,16α,17β-pentol and epimers of this compound where one or two hydroxyl groups are epimerized, e.g., 17α-ethynylandrost-5-ene-3α,4β,11β,16α,17β-pentol, 17α-ethynylandrost-5-ene-3β,4β,11β,16α,17α-pentol, 17α-ethynylandrost-5-ene-3β,4β,11α,16α,17β-pentol and 17α-ethynylandrost-5-ene-3β,4α,11β,16β,17β-pentol. For such compounds, one, two or more of the 5 hydroxyl groups can be derivatized, e.g., to esters or ethers such as methoxy, ethoxy, acetoxy, propionoxy, —O—C(O)—(CH₂)₃—H, —O—C(O)—(CH₂)₄—H or —O—C(O)—(CH₂)₅—H derivatives. Other esters include —O—C(O)—CH₂—C(O)OH, —O—C(O)—(CH₂)₂—C(O)OH, —O—C(O)—(CH₂)₃—C(O)OH, —O—C(O)—(CH₂)₄—C(O)OH, —O—C(O)—(CH₂)₅—C(O)OH and —O—C(O)—(CH₂)₆—C(O)OH. Exemplary compounds include 3β-acetoxy-17α-ethynylandrost-5-ene-4β,7β,16α,17β-tetrol, 3β-acetoxy-17α-ethynylandrost-5-ene-4β,7α,16α,17β-tetrol, 3α-acetoxy-17α-ethynylandrost-5-ene-4β,7β,16α,17β-tetrol, 7β-acetoxy-17α-ethynylandrost-5-ene-3α,4β,16α,17β-tetrol, 3β,7β-diacetoxy-17α-ethynylandrost-5-ene-4β,16α,17β-triol, 3α,16α-diacetoxy-17α-ethynylandrost-5-ene-4β,7α,17β-triol, 3β,16α-diacetoxy-17α-ethynylandrost-5-ene-4α,7α,17β-triol, 3α,17β-diacetoxy-17α-ethynylandrost-5-ene-4β,7β,16α-triol, 3β-acetoxy-17α-ethynylandrost-4-ene-4β,7β,16α,17β-tetrol, 3β-acetoxy-17α-ethynylandrost-4-ene-4β,7α,16α,17β-tetrol, 3α-acetoxy-17α-ethynylandrost-4-ene-4β,7β,16α,17β-tetrol, 7β-acetoxy-17α-ethynylandrost-4-ene-3α,4β,16α,17β-tetrol, 3β-acetoxy-17α-ethynylandrostane-4β,7β,16α,17β-tetrol, 3β-acetoxy-17α-ethynylandrostane-4β,7α,16α,17β-tetrol, 3α-acetoxy-17α-ethynylandrostane-4β,7β,16α,17β-tetrol and 7β-acetoxy-17α-ethynylandrostane-3α,4β,16α,17β-tetrol.

In some of these embodiments four independently selected hydroxyl, esters or ethers are present in a formula 1 compound at four of the 2-, 3-, 4-, 7-, 11-, 16-, and 17-positions. Such substituents can be bonded to, e.g., the 2-, 3-, 16-, and 17-positions, 2-, 3-, 7-, and 17-positions, 2-, 3-, 11-, and 17-positions, 3-, 4-, 7-, and 17-positions, 3-, 4-, 11-, and 17-positions, 3-, 7-, 16-, and 17-positions, 3-, 4-, 16-, and 17-positions or the 3-, 11-, 16-, and 17-positions. The hydroxyl, esters or ethers respectively can be in the 2- and/or 3-β,β,β-17, 2- and/or 3-β,β,β,α-17, 2- and/or 3-β,β,α,β-17, 2- and/or 3-β,α,β,β-17, 2- and/or 3-α,β,β,β-17, 2- and/or 3-β,β,α,α-17, 2- and/or 3-β,α,β,α-17, or in the 2- and/or 3-α,β,β,α-17 configurations when no double bond is present at the 4-position. The term "2- and/or 3-β,β,β-17" means that the 2-position is optionally substituted and the 3- and 17-positions are substituted with hydroxyl, ester or ether. The hydroxyl, esters or ethers respectively can be in the 2- and/or 3-β,α,α,β-17, 2- and/or 3-α,β,α,β-17, 2- and/or 3-α,α,β,β-17, 2- and/or 3-β,α,α,α-17, 2- and/or 3-α,β,α,α-17, 2- and/or 3-α,α,β,α-17, 2- and/or 3-α,α,α,β-17, 2- and/or 3-β,α,α,α-17, configurations when no double bond is present at the 4-position. R¹⁰ in these compounds is typically —H or —F and R⁵ optionally is —CH₃ or —C₂H₅ and R⁶ optionally is —H, —CH₃, —CH₂OH, —CCH or —CCCH₃. For these compounds, the one, two or more of 2-, 3-, 4-, 7-, 11-, 16- and 17-positions are substituted with —H or optionally substituted alkyl such as —CH₃, —C₂H₅, —CH₂=CH₂, —CCH, —CF₃ or —C₂F₅. Exemplary compounds include 17α-ethynylandrost-5-ene-2β,3β,7β,17β-tetrol, 17α-chloroethynylandrost-5-ene-2β,3β,7β,17β-tetrol, 17α-ethynylandrost-5-ene-2β,3α,7β,17β-tetrol, 17α-chloroethynylandrost-5-ene-2β,3α,7β,17β-tetrol, 3β-acetoxy-17α-ethynylandrost-5-ene-2β,7β,17β-triol, 7β-acetoxy-17α-ethynylandrost-5-ene-2α,3β,17β-triol and 3β-diacetoxy-17α-ethynylandrost-5-ene-2β,7β-diol. Other exemplary compounds include 17α-ethynylandrost-5-ene-2α,3β,11β,17β-tetrol, 17α-chloroethynylandrost-5-ene-2α,3β,11β,17β-tetrol, 17α-ethynylandrost-5-ene-2β,3α,11β,17β-tetrol, 3β-acetoxy-17α-ethynylandrost-5-ene-2α,11β,17β-triol, 3α-acetoxy-17α-ethynylandrost-5-ene-2α,11α,17β-triol, 3β,17β-diacetoxy-17α-ethynylandrost-5-ene-2α,11β-diol, 17α-ethynylandrost-5-ene-2α,3β,16α,17β-tetrol, 17α-chloroethynylandrost-5-ene-2α,3β,16α,17β-tetrol, 17α-ethynylandrost-5-ene-2β,3α,16β,17β-tetrol, 3β-acetoxy-17α-ethynylandrost-5-ene-2α,16α,17β-triol, 3α-acetoxy-17α-ethynylandrost-5-ene-2α,16α,17β-triol and 3β,17β-diacetoxy-17α-ethynylandrost-5-ene-2α,16α-diol.

In some embodiments of the formula 1 compounds, five independently selected hydroxyl, ester and/or ether moieties can be present. For these compounds, hydroxyl, ester and/or ether moieties are usually present at the 3- and 17-positions and at 3 other positions. These substituents can be at the 2-, 3-, 4-, 7- 11-, 17- and 18-positions, e.g., at the 2-, 3-, 7- 16- and 17-positions or 2-, 3-, 11- 16- and 17-positions. Independently selected hydroxyl, ester and/or ether moieties can be present at the 3-, 4-, 7- 11- and 17-positions, 3-, 4-, 11- 16- and 17-positions, 3-, 4-, 7- 16- and 17-positions or the 3-, 7-, 11-, 16-, 17-positions. For these compounds, each moiety can be in the α-configuration or the β-configuration when no double bond is present at the 4-position. Thus, substituents in these compounds can respectively be in the 2- and/or 3-β,β, β,β,β-17, 2- and/or 3-β,β,β,β,α-17, 2- and/or 3-β,β,β,α,β-17, 2- and/or 3-β,β,α,β,β-17, 2- and/or 3-β,α,β,β,β-17, 2- and/or 3-αβ,β,β,β-17, 2- and/or 3-β,β,β,αα-17, 2- and/or 3-β,β,α, β,α-17, 2- and/or 3-β,α,β,β,α-17, 2- and/or 3-α,β,β,β,α-17, 2- and/or 3-β,β,α,α,β-17, 2- and/or 3-β,α,β,α,β-17, 2- and/or 3-α,β,β,α,β-17, 2- and/or 3-β,α,α,β,β-17, 2- and/or 3-α,β,α, β,β-17, 2- and/or 3-α,α,β,β,β-17 or in the 2- and/or 3-β,β,α, α,α-17 configurations respectively. The substituents in these compounds can also respectively be in the 2- and/or 3-β,α,β, α,α-17, 2- and/or 3-β,α,α,β,α-17, 2- and/or 3-β,α,α,α,β-17, 2- and/or 3-α,β,β,α,α-17, 2- and/or 3-α,β,α,β,α-17, 2- and/or 3-β,α,α,α,β-17, 2- and/or 3-αα,β,β,α-17, 2- and/or 3-α, α,β,α,β-17, 2- and/or 3-α,α,α,β,β-17, 2- and/or 3-β,α,α,α, α-17, 2- and/or 3-α,β,α,α,α17, 2- and/or 3-α,β,α,α,α-17, 2- and/or 3-α,α,α,β,α-17, 2- and/or 3-α,α,α,α,β-17 or in the 2- and/or 3-α,α,α,α,α-17 configurations respectively. Exemplary compounds include (1) 17α-ethynylandrost-5-ene-2β, 3β,7β,16α,17β-pentol, 17α-chloroethynylandrost-5-ene-2α, 3β,7β,16α,17β-pentol, 17α-ethynylandrost-5-ene-2β,3α, 7β,16α,17β-pentol, 17α-chloroethynylandrost-5-ene-2β,3α, 7β,16α,17β-pentol, 3β-acetoxy-17α-ethynylandrost-5-ene-2β,7β,16α,17β-tetrol, 17β-acetoxy-17α-ethynylandrost-5-ene-2β,3α,7β,16α-tetrol, 3β,2α-diacetoxy-17α-ethynylandrost-5-ene-7β,16α,17β-triol and isomers of any of these compounds where the moiety at the 3-position or the 7-position is inverted, e.g., 3β-OH or 3β-acetate is inverted to 3α-OH 3α-acetate, (2) 17α-ethynylandrost-5-ene-3β,4α,7β, 17β,18-pentol, 17α-chloroethynylandrost-5-ene-3α,4β,7α, 17β,18-pentol, 17α-ethynylandrost-5-ene-3β,4α,7α,17β,18-pentol, 3β-acetoxy-17α-ethynylandrost-5-ene-4α,7α,17β, 18-tetrol and isomers of any of these compounds where the moiety at the 3-position or the 7-position is inverted and (3) 17α-ethynylandrost-5-ene-3β,4α,16α,17β,18-pentol, 17α-ethynylandrost-5-ene-3β,4α,16β,17β,18-pentol, 17α-chloroethynylandrost-5-ene-3β,4α,16α,17β,18-pentol, 3β-acetoxy-17α-ethynylandrost-5-ene-4α,16α,17β,18-tetrol, 4β-acetoxy-17α-ethynylandrost-5-ene-3α,16α,17β,18-tetrol, 3β,16α-diacetoxy-17α-ethynylandrost-5-ene-4α,17β, 18-triol and isomers of any of these compounds where the moiety at the 3-position or the 4-position, if present, is inverted.

For the formula 1 compounds described herein, the 16-position may be unsubstituted, i.e., one or both $R^3$ are —H, and a second $R^4$ can be present at the 17-position in the α-configuration or the β-configuration when no double bond is present at the 17-position. Such second $R^4$ moieties include $C_{1-8}$ optionally substituted alkyl such as —$CH_3$, —$C_2H_5$, —$CF_3$, —$C_2F_5$, —C=$CH_2$, —CCH, —CCCl—$CCCH_3$ or —$CCCH_2Cl$.

For any of these compounds, the 2-position may be unsubstituted, i.e., $R^9$ is —$CH_2$—. In some embodiments, $R^9$ is substituted, e.g., —O—, —CH(OH)—, —CH(ester)- or —CH(ether)- where the hydroxyl, ester or ether moiety is in the α- or β-configuration. Exemplary $R^9$ moieties are —CH (α-OH)—, —CH(β-OH)—, —C(β-$CH_3$)(α-OH)—, —C(α-$CH_3$)(β-OH)—, —CH(α-$OCH_3$)—, —CH(β-$OCH_3$)—, —CH(α-OC(O)$CH_3$)— and —CH(β-OC(O)$CH_3$)—. Other $R^9$ moieties are —CH(α-OC(O)$CH_2CH_3$)—, —CH(β-OC (O)$CH_2CH_3$)—, —CH(α-$OCH_2CH_3$)—, —CH(β-$OCH_2CH_3$)—, —C(O—$CH_3$)(α-OC(O)$CH_3$)— and —C(α-$CH_3$)(β-OC(O)$CH_3$)—.

Exemplary F1Cs that can be used to treat metabolic diseases, lung conditions, autoimmune, inflammatory or other conditions described herein. These compounds include 4β-fluoro-17α-ethynylandrost-5-ene-3β,7β, 17β-triol, 4α-fluoro-17α-ethynylandrost-5-ene-3β,7β,17β-triol, 4β-fluoro-17α-ethynylandrost-5-ene-3α,7β,17β-triol, 4α-fluoro-17α-ethynylandrost-5-ene-3α,7β,17β-triol, 4β-fluoro-17α-ethynylandrost-5-ene-3β,7α,17β-triol, 4α-fluoro-17α-ethynylandrost-5-ene-3β,7β,17β-triol, 4β-fluoro-17α-ethynylandrost-5-ene-3α,7α,17β-triol, 4α-fluoro-17α-ethynylandrost-5-ene-3α,7α,17β-triol, 17α-ethynylandrost-5-ene-3β,7β,17β-triol, 17β-ethynylandrost-5-ene-3β,7β,17α-triol, 17α-ethynylandrost-5-ene-3β,7β-diol-7-one, 17α-ethynylandrost-5-ene-3α,17β-diol-7-one, 17α-ethynylandrost-5-ene-3β,7β,17β-triol, 17α-ethynylandrost-5-ene-3β,7α,17β-triol and an analog of any of these compounds where (1) an ester such as acetate replaces the hydroxyl group at the 3-position or at the 7-position, e.g., 7β-acetoxy-17α-ethynylandrost-5-ene-3β,17β-diol, 7β-acetoxy-17α-ethynylandrost-5-ene-3α,17β-diol, 3β-acetoxy-4β-fluoro-17α-ethynylandrost-5-ene-7β,17β-diol or 7β-acetoxy-4β-fluoro-17α-ethynylandrost-5-ene-3α,17β-diol or (2) the ethynyl moiety at the 17-position is replaced with an optionally substituted $C_{2-4}$ alkynyl moiety such as chloroethynyl. Other F1Cs include 17α-ethynylandrost-5-ene-3β,4α, 7β,17β-tetrol, 17α-ethynylandrost-5-ene-3α,4α,7β,17β-tetrol, 17α-ethynylandrost-5-ene-3β,4β,7β,17β-tetrol, 17α-ethynylandrost-5-ene-3α,4β,7β,17β-tetrol, 17α-ethynylandrost-5-ene-3β,4α,7α,17β-tetrol and 17α-ethynylandrost-5-ene-3α,4α,7α,17β-tetrol. Other F1C analogs of the foregoing compounds have an optionally substituted C2-4 alkynyl moiety such as —C≡C—Cl, —$CCCH_3$ or —C≡C—$CH_2Cl$ that replaces the ethynyl moiety at the 17-position, e.g., 4α-fluoro-17α-chloroethynylandrost-5-ene-3β,7β,17β-triol, 4α-fluoro-17α-chloroethynylandrost-5-ene-3α,7β,17β-triol, 17α-chloroethynylandrost-5-ene-3β,7β,17β-triol, 17α-chloroethynylandrost-5-ene-3β, 7α,17β-triol and 17α-chloroethynylandrost-5-ene-3α,7β, 17β-triol.

F1Cs also include 4β-fluoro-17α-ethynylandrostane-3β, 7β,17β-triol, 4α-fluoro-17α-ethynylandrostane-3β,7β,17β-triol, 4β-fluoro-17α-ethynylandrostane-3α,7β,17β-triol, 4α-fluoro-17α-ethynylandrostane-3α,7β,17β-triol, 4β-fluoro-17α-ethynylandrostane-3β,7α,17β-triol, 4α-fluoro-17α-ethynylandrostane-3β,7α,17β-triol, 4β-fluoro-17α-ethynylandrostane-3α,7α,17β-triol, 4α-fluoro-17α-ethynylandrostane-3α,7α,17β-triol, 17α-ethynylandrostane-3β,7β,17β-triol, 17α-ethynylandrostane-3β,17β-diol-7-one, 17α-ethynylandrostane-7β,17β-diol-3-one, 17α-ethynylandrostane-3α,7β,17β-triol, 17α-ethynylandrostane-3β,7α,17β-triol and an analog of any of these compounds wherein an ester such as acetate replaces the hydroxyl group at the 3-position or at the 7-position, e.g., 7β-acetoxy-17α-ethynylandrostane-3β,17β-diol, 7β-acetoxy-17α-ethynylandrostane-3α,17β-diol, 3β-acetoxy-4β-fluoro-17α-ethynylandrostane-7β,17β-diol, 7β-acetoxy-4β-fluoro-17α-ethynylandrostane-3α,17β-diol, 17α-ethynylandrostane-3β,4β,7β,17β-tetrol, 17α-ethynylandrostane-3α,4α,7β,17β-tetrol, 17α-ethynylandrostane-3β,4β,7β,17β-tetrol, 17α-ethynylandrostane-3α,4α,7β,17β-tetrol, 17α-ethynylandrostane-3β,4α, 7α,17β-tetrol and 17α-ethynylandrostane-3α, 4α, 7α,17β-tetrol. Other F1C analogs of the foregoing compounds have an optionally substituted C2-4 alkynyl moiety such as —C≡C—Cl, —$CCCH_3$ or —C≡C—$CH_2Cl$ that replaces the ethynyl moiety at the 17-position, e.g., 4α-fluoro-17α-chloroethynylandrostane- 3β, 7β,17β-triol, 4α-fluoro-17α-chloroethynylandrostane-3α,7β,17β-triol, 17α-chloroethynylandrostane-3β,7β,17β-triol, 17α-chloroethynylandrostane-3β,7α,17β-triol and 17α-chloroethynylandrostane-3α,7β,17β-triol.

F1Cs include 4β-fluoro-17α-ethynylandrost-4-ene-3β,7β,17β-triol, 4α-fluoro-17α-ethynylandrost-4-ene-3β,7β,17β-triol, 4β-fluoro-17α-ethynylandrost-4-ene-3α,7β,17β-triol, 4α-fluoro-17α-ethynylandrost-4-ene-3α,7β,17β-triol, 4β-fluoro-17α-ethynylandrost-4-ene-3β,7α,17β-triol, 4α-fluoro-17α-ethynylandrost-4-ene-3β,7α,17β-triol, 4β-fluoro-17α-ethynylandrost-4-ene-3α,7α,17β-triol, 4α-fluoro-17α-ethynylandrost-4-ene-3α,7α,17β-triol, 17α-ethynylandrost-4-ene-3β,7β,17β-triol, 17α-ethynylandrost-4-ene-3β,7β,17β-triol, 17α-ethynylandrost-4-ene-3β,7α,17β-triol, 17α-ethynylandrost-4-ene-3β,17β-diol-7-one, 17α-ethynylandrost-4-ene-7β,17β-diol-3-one, 17α-ethynylandrost-4-ene-3α,17β-diol-7-one and an analog of any of these compounds wherein an ester such as acetate replaces the hydroxyl group at the 3-position or at the 7-position, e.g., 7β-acetoxy-17α-ethynylandrost-4-ene-3β,17β-diol, 7β-acetoxy-17α-ethynylandrost-4-ene-3α,17β-diol, 3β-acetoxy-4β-fluoro-17α-ethynylandrost-4-ene-7β,17β-diol, 7β-acetoxy-4β-fluoro-17α-ethynylandrost-4-ene-3α,17β-diol, 17α-ethynylandrost-4-ene-3β,4α,7β,17β-tetrol, 17α-ethynylandrost-4-ene-3α,4α,7β,17β-tetrol, 17α-ethynylandrost-4-ene-3β,4β,7β,17β-tetrol, 17α-ethynylandrost-4-ene-3α,4β,7β,17β-tetrol, 17α-ethynylandrost-4-ene-3β,4α,7β,17β-tetrol and 17α-ethynylandrost-4-ene-3α,4α,7α,17β-tetrol. Other F1C analogs of the foregoing compounds have an optionally substituted $C_{2-4}$ alkynyl moiety such as —C≡C—Cl, —CCCH₃ or —C≡C—CH₂Cl that replaces the ethynyl moiety at the 17-position, e.g., 4α-fluoro-17α-chloroethynylandrost-4-ene-3β,7β,17β-triol, 4α-fluoro-17α-chloroethynylandrost-4-ene-3α,7β,17β-triol, 17α-chloroethynylandrost-4-ene-3β,7β,17β-triol, 17α-chloroethynylandrost-4-ene-3β,7α,17β-triol and 17α-chloroethynylandrost-4-ene-3α,7β,17β-triol.

Other exemplary F1Cs include 4β-fluoro-17α-ethynylandrost-5-ene-3β,16α,17β-triol, 4α-fluoro-17α-ethynylandrost-5-ene-3β,16α,17β-triol, 4β-fluoro-17α-ethynylandrost-5-ene-3α,16α,17β-triol, 4α-fluoro-17α-ethynylandrost-5-ene-3α,16α,17β-triol, 4β-fluoro-17α-ethynylandrost-5-ene-3β,16β,17β-triol, 4α-fluoro-17α-ethynylandrost-5-ene-3β,16β,17β-triol, 4β-fluoro-17α-ethynylandrost-5-ene-3α,16α,17β-triol, 4α-fluoro-17α-ethynylandrost-5-ene-3α,16α,17β-triol, 17α-ethynylandrost-5-ene-3β,4α,16α,17β-tetrol, 17α-ethynylandrost-5-ene-3α,4α,16α,17β-tetrol, 17α-ethynylandrost-5-ene-3β,4β,16α,17β-tetrol, 17α-ethynylandrost-5-ene-3α,4β,16α,17β-tetrol, 17α-ethynylandrost-5-ene-4α,16α,17β-triol-3-one, and an analog of any of these compounds wherein an ester such as acetate replaces the hydroxyl group at the 3-position or at the 16-position, e.g., 16α-acetoxy-17α-ethynylandrost-5-ene-3β,17β-diol, 16α-acetoxy-17α-ethynylandrost-5-ene-3α,17β-diol, 3β-acetoxy-4β-fluoro-17α-ethynylandrost-5-ene-16α,17β-diol, 16β-acetoxy-4β-fluoro-17α-ethynylandrost-5-ene-3α,17β-diol, 3β-acetoxy-17α-ethynylandrost-5-ene-4β,16α,17β-triol, 3α-acetoxy-17α-ethynylandrost-5-ene-4β,16α,17β-triol, 16α-acetoxy-17α-ethynylandrost-5-ene-3β,4β,17β-triol and 16α-acetoxy-17α-ethynylandrost-5-ene-3α,4β,17β-triol. Other F1C analogs of the foregoing compounds have an optionally substituted C2-4 alkynyl moiety such as —C≡C—Cl, —CCCH₃ or —C≡C—CH₂Cl that replaces the ethynyl moiety at the 17-position, e.g., 4β-fluoro-17α-chloroethynylandrost-5-ene-3β,16α,17β-triol, 4α-fluoro-17α-chloroethynylandrost-5-ene-3β,16α,17β-triol, 17α-chloroethynylandrost-5-ene-3α,4α,16α,17β-tetrol and 17α-chloroethynylandrost-5-ene-3α,4α,16α,17β-tetrol.

Other exemplary F1Cs include 4β-fluoro-17α-ethynylandrost-4-ene-3β,16α,17β-triol, 4α-fluoro-17α-ethynylandrost-4-ene-3β,16α,17β-triol, 4β-fluoro-17α-ethynylandrost-4-ene-3α,16α,17β-triol, 4α-fluoro-17α-ethynylandrost-4-ene-3α,16α,17β-triol, 4β-fluoro-17α-ethynylandrost-4-ene-3β,16β,17β-triol, 4α-fluoro-17α-ethynylandrost-4-ene-3β,16β,17β-triol, 4β-fluoro-17α-ethynylandrost-4-ene-3α,16α,17β-triol, 4α-fluoro-17α-ethynylandrost-4-ene-3α,16α,17β-triol, 17α-ethynylandrost-4-ene-3β,4α,16α,17β-tetrol, 17α-ethynylandrost-4-ene-3α,4α,16α,17β-tetrol, 17α-ethynylandrost-4-ene-3β,4β,16α,17β-tetrol, 17α-ethynylandrost-4-ene-3α,4β,16α,17β-tetrol, 4β-fluoro-17α-ethynylandrost-4-ene-16α,17β-diol-3-one, 17α-ethynylandrost-4-ene-4α,16α,17β-triol-3-one and an analog of any of these compounds wherein an ester such as acetate replaces the hydroxyl group at the 3-position or at the 16-position, e.g., 16α-acetoxy-17α-ethynylandrost-4-ene-3β,17β-diol, 16α-acetoxy-17α-ethynylandrost-4-ene-3α,17β-diol, 3β-acetoxy-4β-fluoro-17α-ethynylandrost-4-ene-16α,17β-diol, 16β-acetoxy-4β-fluoro-17α-ethynylandrost-4-ene-3α,17β-diol, 3β-acetoxy-17α-ethynylandrost-4-ene-4β,16α,17β-tetrol, 3α-acetoxy-17α-ethynylandrost-4-ene-4β,16α,17β-tetrol, 16α-acetoxy-17α-ethynylandrost-4-ene-3β,4β,17β-triol and 16α-acetoxy-17α-ethynylandrost-4-ene-3α,4β,17β-triol. F1C analogs of the foregoing compounds have an optionally substituted C2-4 alkynyl moiety such as —C≡C—Cl, —CCCH₃ or —C≡C—CH₂Cl that replaces the ethynyl moiety at the 17-position, e.g., 4β-fluoro-17α-chloroethynylandrost-4-ene-3α,16α,17β-triol, 4α-fluoro-17α-chloroethynylandrost-4-ene-3β,16α,17β-triol, 17α-chloroethynylandrost-4-ene-3β,4α,16α,17β-tetrol and 17α-chloroethynylandrost-4-ene-3α, 4α,16α,17β-tetrol.

Other exemplary F1Cs include 4β-fluoro-17α-ethynylandrostane-3β,16α,17β-triol, 4α-fluoro-17α-ethynylandrostane-3β,16α,17β-triol, 4β-fluoro-17α-ethynylandrostane-3α,16α,17β-triol, 4α-fluoro-17α-ethynylandrostane-3α,16α,17β-triol, 4β-fluoro-17α-ethynylandrostane-3β,16β,17β-triol, 4α-fluoro-17α-ethynylandrostane-3β,16β,17β-triol, 4β-fluoro-17α-ethynylandrostane-3α,16α,17β-triol, 4α-fluoro-17α-ethynylandrostane-3α,16α,17β-triol, 17α-ethynylandrostane-3β,4α,16α,17β-tetrol, 17α-ethynylandrostane-3α, 4α,16α,17β-tetrol, 17α-ethynylandrostane-3β, 4β,16α,17β-tetrol, 17α-ethynylandrostane-3α,4β,16α,17β-tetrol, 4β-fluoro-17α-ethynylandrostane-16α,17β-diol-3-one, 17α-ethynylandrostane-4β,16α,17β-triol-3-one, and an analog of any of these compounds wherein an ester such as acetate replaces the hydroxyl group at the 3-position (if present), 4-position or at the 16-position, e.g., 16α-acetoxy-17α-ethynylandrostane-3β,4α,17β-triol, 16α-acetoxy-17α-ethynylandrostane-3β,4β,17β-triol, 16α-acetoxy-17α-ethynylandrostane-3α,4α,17β-triol, 4α-acetoxy-17α-ethynylandrostane-3β,16α,17β-triol, 16β-acetoxy-4β-fluoro-17α-ethynylandrostane-3α, 17β-diol, 3β-acetoxy-17α-ethynylandrostane-4β,16α,17β-tetrol, 3α-acetoxy-17α-ethynylandrostane-4β,16α,17β-tetrol, 16α-acetoxy-17α-ethynylandrostane-3β,4β,17β-triol and 16α-acetoxy-17α-ethynylandrostane-3α,4β,17β-triol. F1C analogs of the foregoing compounds have an optionally substituted C2-4 alkynyl moiety such as —C≡C—Cl, —CCCH₃ or —C≡C—CH₂Cl that replaces the ethynyl moiety at the 17-position, e.g., 4α-fluoro-17α-chloroethynylandrostane-3β,16α,17β-triol, 4α-fluoro-17α-chloroethynylandrostane-3α,16α,17β-triol, 17α-chloroethynylandrostane-3β,4α,16α,17β-tetrol and 17α-chloroethynylandrostane-3α,4α,16α,17β-tetrol.

Biodynamic compounds. The method to identify or characterize a biodynamic compound comprising can be accomplished as described above. The method optionally further comprises conducting a protocol to determine if the test compound modulates the activity or level of the mediator of the acute biological response by about 20% or about 25% to about 70% or about 75% in an assay in vitro, optionally wherein the test compound does not activate or antagonize a glucocorticoid receptor by more than about 10%, about 20% or about 30% when compared to a suitable reference activator or antagonist of the glucocorticoid receptor, e.g., dexamethasone or cortisol. In these embodiments, the acute stimulus or biological insult can be exposure of the subject to a sufficient amount of ionizing radiation or a proinflammatory signal, compound or composition, optionally wherein the proinflammatory signal, compound or composition is bacterial LPS or TNFα, and/or optionally wherein the mediator of the acute biological response is NF-κB or IκB.

The acute stimulus or biological insult can be administration of sufficient bacterial LPS to a sufficient number of drug treated mice and a sufficient number vehicle control mice and measurement of the effect of the test compound on the mediator of the acute biological response at a time when (i) the acute response is maximal or nearly maximal, optionally at about 1.5 hours, e.g., at about 70-110 minutes or 75-105 minutes, after administration of bacterial LPS by intraperitoneal injection and (ii) one or two other time points before and/or after the administration of the sufficient bacterial LPS, optionally at one time point before the administration of the sufficient bacterial LPS and at one later time after the acute response is maximal or nearly maximal, optionally at about 2.0 or 2.5 hours after administration of bacterial LPS by intraperitoneal injection, and optionally wherein the mediator of the acute biological response is NF-κB or IκB.

The administration of sufficient bacterial LPS can optionally be accomplished essentially according to the methods described herein or a suitable variation thereof and optionally wherein the capacity of the compound to partially modulate the level or activity of the mediator of the acute biological response is accomplished essentially according to a method described herein or a suitable variation thereof.

Other stimuli or biological insults that can be analyzed include ischemia and reperfusion of one or more ischemic tissues, thermal or chemical burns of relatively low, moderate or high severity.

The capacity of 17α-ethynylandrost-5-ene-3β,7β,17β-triol to exert a transient, but very potent, effect, which fades, and normal function returns is referred to herein as a biodynamic response (see example 9). A biodynamic response elicited by a 'biodynamic agent' such as 17α-ethynylandrost-5-ene-3β,7β,17β-triol contrasts with a 'biostatic response' that a compound such as dexamethasone elicits toward its effector biomolecules such as the glucocorticoid receptor or NF-κB, which it inhibits indirectly through activation of the glucocorticoid receptor. The biostatic response essentially is an 'all on all the time' response with the biological potency of a 'biostatic agent' such as dexamethasone having relatively little variation at a given concentration at target cells or tissues.

The pharmacodynamic effect of a biostatic agent appears to vary primarily with its concentration or pharmacokinetic properties. By contrast, biodynamic agents such as 17α-ethynylandrost-5-ene-3β,7β,17β-triol are characterized by a pharmacodynamic effect that is affected by a combination of its concentration at target cells or tissues and the nature and intensity of the underlying biological stimulus. Thus, a biological stimulus elicited, e.g., by exposure to a potentially lethal amount of ionizing radiation such a γ-rays or X-rays or exposure to bacterial LPS, TNFα or another agent that can activate or inhibit mediators of inflammation such as NF-κB, IκB, IL-6, C reactive protein. In this regard, biodynamic drugs can exhibit a looser statistical correlation, or no significant correlation, between pharmacokinetic and pharmacodynamic effects compared to what is generally observed for biostatic drugs.

One aspect of biodynamic drugs is their potential capacity to decrease systemic toxicity associated with biostatic drugs that may act at least in part through modulating the same or similar target biomolecules. Biostatic dugs such as dexamethasone can be used clinically to treat a wide range of inflammation conditions, but the 'all on all the time' bioactivity can lead to toxicity. In the case of inhibiting NF-κB, constant and relatively complete inhibition of its activity, e.g., inhibition by about 75%, 80%, 85%, 90%, 95% or essentially 100% in most or all tissues, for a prolonged time, e.g., for more than 1, 2 or 4 hours to about 1, 2, 3 days or more, can result in observable unwanted side-effects since some basal level of NF-κB activity is needed for normal biological function in most tissues. Known toxicities associated with the use of glucocorticoids such as dexamethasone are likely to arise at least in part from the relatively complete shut-down of affected biomolecules such as NF-κB. By contrast, biodynamic drugs can exert a more transient response that can lead to an amelioration or decrease in observable toxic side effects.

Another aspect of biodynamic drugs is their capacity to potentially exert a therapeutic effect in a tissue-specific manner. Thus, an animal's response to a challenge such as exposure to a biological insult such as a potentially lethal amount of bacterial LPS or reperfusion of affected tissues after transient ischemia may be manifested by varying degrees of NF-κB activation in varying tissues. A biodynamic drug could act in tissues where the animal's response is relatively great, e.g., mouse spleen or cardiac tissue, while leaving the function of NF-κB relatively unaffected in other tissues, e.g., brain, where the response to the biological insult is relatively lower for the target biomolecule that at least partially mediates the response to the biological insult.

Biodynamic drugs may act in part by their capacity to partially inhibit target biomolecules. As described below in example 7, 17α-ethynylandrost-5-ene-3β,7β,17β-triol and some other compounds described there partially inhibited activation of NF-kB in the cells in vitro, but complete inhibition was not observed at any concentration. For most of these compounds the degree of inhibition of NF-kB was about 25-80%, typically about 30-65% or about 30-70%, an unexpected phenomenon that was not previously described for these compounds. This contrasted with the activity of the biostatic drug dexamethasone, which completely inhibited NF-κB activity at a sufficiently high concentration. This partial inhibition of NF-κB in vitro appears to be partially reflected by its activity described in this example. Thus, in at least some cases, biodynamic drugs are characterized by having a capacity to partially inhibit or activate a target biomolecule in a system such as the in vitro assay described below. The inhibition of NF-κB appears to be indirect, since it is not believed at present that 17α-ethynylandrost-5-ene-3β,7β,17β-triol and the other compounds described here bind directly to NF-κB in the cytoplasm or the nucleus.

The protocol described in example 7 below, or suitable variations of it, can be used to characterize other compounds for their potential to act as biodynamic or biostatic agents by modulating (detectably activating or detectably antagonizing or inhibiting) molecules such as NF-κB in vivo, where such modulation is typically partial inhibition or partial activation.

The compounds can also be analyzed in in vitro assays such as the assay described in example 7 to further characterize their mechanism of action. Suitable variations of the in vivo protocols described herein include using various dosages of test compounds and various routes of administration, e.g., a dose range of about 0.1 mg/kg to about 350 mg/kg administered orally, buccally, sublingually or parenterally such as intradermal, subcutaneous, intravenous or intramuscular injection or by intranasal or inhalation to the nasal passages, vomeronasal organ or lung alveoli or airway passages leading to the alveoli, e.g., bronchi or bronchioli. Suitable test dosages will typically be about 1-150 mg/kg. Biomolecules that can be measured in vivo such as IκB, kinases such as src kinase, a map kinase or other signal mediators described herein. Such characterization methods can be conducted in one or more of a range of subjects such as rodents, e.g., rats, dogs, non-human primates such as rhesus or cynomolgus monkeys. Groups of animals consisting of about 3-12 animals per group, e.g., 4-8 animals per group, can be used with suitable vehicle or placebo controls, test compounds that are potential biodynamic drugs, positive biodynamic drug controls such as 17α-ethynylandrost-5-ene-3β,7β,17β-triol, positive biostatic drug controls such as dexamethasone and groups where the response of the test compound in different cell populations or tissues are compared against one or more control groups, e.g., vehicle controls, positive or negative biodynamic drug controls or positive or negative biostatic drug controls. Other compounds that can be used in these methods as control or reference compounds include 17α-ethynylandrost-5-ene-3α, 7β,17β-triol, 17α-ethynylandrost-5-ene-3β,7α,17β-triol, 17α-ethynylandrost-5-ene-3β, 17β-diol-7-one, 17α-ethynylandrost-5-ene-3β,7β,16α,17β-tetrol and 17α-ethynylandrost-5-ene-3α,7β,16α,17β-tetrol.

When such analyses are applied to humans, the range of experimental options will naturally differ compared to other animals. Human tissues or samples such as blood, bone marrow or lung lavage fluid will be more readily accessible for analyses than other tissue types such as spleen or liver, which need to be obtained by invasive techniques. Thus, in general, animal studies will be conducted before human response assessment.

Inflammation treatments. An aspect of some claimed embodiments is that the formula 1 compounds can decrease inflammation by affecting mediators of inflammation such as NF-κB, IL-6 or TNFα. The NF-κB molecule often is an important mediator of inflammation. Increased activation of NF-κB is associated with a range of inflammatory diseases and autoimmune conditions. Anti-inflammatory activity from compounds in vivo could arise, e.g., from eliciting prostaglandin synthesis and other activity in liver, leading to a systemic anti-inflammation response. Alternatively, anti-inflammation activity for compounds could arise from the capacity of the compounds to inhibit stimulation of NF-κB activity that arises from sources other than LPS. A number of different materials can activate NF-κB activity, including LPS, TNF-α, IL-1, the presence of certain viral or bacterial gene products, activation of B-cells or T-cells, or exposure of cells to ultraviolet radiation. Not all cell types can respond to all of these stimuli since not all cells express the signaling machinery that is needed to respond to each of these stimuli. Most cell types can respond to one or a few of these signals, but rarely can a given cell type respond to all.

The formula 1 compounds can be used to treat or ameliorate conditions or symptoms associated with conditions. Conditions and symptoms include inflammation such as pain, fever or fatigue; endometriosis; fever; fibromyalgia; a myelitis condition such as acute transverse myelitis; glomerulonephritis; graft versus host disease, organ or tissue transplant rejection, e.g., kidney, lung, bone marrow or liver transplant; hemorrhagic shock; fibromyalgia; hyperalgesia; inflammatory bowel disease; gastritis; irritable bowel syndrome; ulcerative colitis; a peptic ulcer; a stress ulcer; a bleeding ulcer; gastric hyperacidity; dyspepsia; gastroparesis; gastroesophageal reflux disease; inflammatory conditions of a joint, including osteoarthritis, psoriatic arthritis and rheumatoid arthritis; inflammatory eye disease, as may be associated with, e.g., corneal transplant; ischemia, including cerebral ischemia (e.g., brain injury as a result of trauma, epilepsy, hemorrhage or stroke, each of which may lead to neurodegeneration); Kawasaki's disease; learning impairment; lung diseases (e.g., ARDS); a demyelinating condition such as multiple sclerosis or progressive multifocal leukoencephalopathy, which may be remitting or relapsing; myopathies (e.g., muscle protein metabolism, especially in sepsis); neurotoxicity (e.g., as induced by HIV); osteoporosis; pain, including cancer-related pain; Parkinson's disease; Alzheimer's disease; periodontal disease; pre-term labor; psoriasis; reperfusion injury; septic shock; side effects from radiation therapy; temporal mandibular joint disease; alcohol-induced liver injury including alcoholic cirrhosis; rheumatic fever; sarcoidosis; scleroderma; chronic fatigue syndrome; coronary conditions and indications, including congestive heart failure, coronary restenosis, myocardial infarction, myocardial dysfunction (e.g., related to sepsis), and coronary artery bypass graft; sleep disturbance; uveitis; seronegative polyarthritis; ankylosing spondylitis; Reiter's syndrome and reactive arthritis; Still's disease; psoriatic arthritis; enteropathic arthritis; polymyositis; dermatomyositis; scleroderma; systemic sclerosis; vasculitis (e.g., Kawasaki's disease); inflammation resulting from, e.g., strain, sprain or cartilage damage; wound healing; thin or fragile skin; petechiae or ecchymoses; erythema; and trauma. Trauma includes wounds, chemical burns, thermal burns, radiation burns and tissue or organ damage associated with a surgery such as an orthopedic surgery or an abdominal surgery. Inflammation conditions can include inflammation associated with reperfusion injury, restenosis after angioplasty, myocardial or cerebral infarction.

Unwanted inflammation conditions or symptoms, include lung inflammation conditions, e.g., cystic fibrosis, acute asthma, chronic asthma, steroid resistant asthma, acute bronchitis, chronic bronchitis, emphysema, psoriasis, eczema, adult respiratory distress syndrome (ARDS) or chronic obstructive pulmonary disease (COPD).

Autoimmune and pulmonary conditions. In some claimed embodiments, the formula 1 compounds (F1Cs) or compositions described herein can be used to treat, prevent or slow the progression of autoimmune or related conditions such as type 1 diabetes, Crohn's disease, arthritis, contact dermatitis, lupus and multiple sclerosis (MS) conditions. MS conditions include relapsing-remitting MS and secondary progressive MS. The lupus conditions include systemic lupus erythematosus, lupus erythematosus-related arthritis, lupus erythematosus-related skin changes, lupus erythematosus-related hematologic abnormalities, lupus erythematosus-related kidney impairment, lupus erythematosus-related heart or lung disease, lupus erythematosus-related neuropsychiatric changes, lupus erythematosus-related tissue inflammation, discoid lupus erythematosus, subacute cutaneous lupus erythematosus and drug-induced lupus erythematosus. Arthritis and related conditions include rheumatoid arthritis, osteoarthritis, fibromyalgia, primary osteoarthritis, secondary osteoarthritis, psoriatic arthritis, lupus erythematosus-related arthritis, arthritis associated with acute or chronic inflammatory bowel disease or colitis, arthritis associated with ankylosing spondylitis, arthritis-related tissue inflammation, joint pain, joint stiffness, impaired joint movement, joint swelling, joint inflammation and synovium inflammation.

In these claimed embodiments, the F1Cs or compositions containing a F1C and one or more excipients can be used to treat, prevent, delay the onset of or slow the progression of conditions such as ankylosing spondylitis, psoriasis, eczema, a dermatitis such as contact dermatitis, a colitis such as ulcerative colitis, Crohn's disease, acute or chronic inflammatory bowel disease, autoimmune renal injury and liver injury.

Experimental autoimmune encephalomyelitis (EAE) is an experimental condition in animals that has clinical, histopathological and immunological characteristics similar to human MS and, as with MS, exhibits infiltration into the CNS of T-cells and monocytes. EAE can be induced in susceptible mice by immunization with proteolipid lipoprotein (PLP) in suitable adjuvants. The EAE animal model is an in vivo model of human MS used to study pathogenic mechanisms of MS and to characterize new agents for treating MS.

The F1Cs can be used in treating lung and airway conditions including asthma conditions such as steroid independent asthma, severe asthma, atopic asthma, acute asthma or chronic asthma, allergic rhinitis, chronic bronchitis, acute bronchitis, cystic fibrosis, emphysema, lung fibrosis, lung airway hyperresponsiveness, chronic obstructive pulmonary disease, pulmonary edema, pulmonary hypertension and acute respiratory distress syndrome.

Exemplary compounds in the treatments include 17α-ethynylandrost-5-ene-3β,7β,11β,17β-tetrol, 17α-ethynylandrost-5-ene-3α,7β,11β,17β-tetrol, 17α-ethynylandrost-5-ene-3β,7β,17β-triol, 17α-ethynylandrost-5-ene-3β,7β, 11β, 17β-tetrol, 17β-ethynylandrost-5-ene-3β,7β,17α-triol, 17α-ethynylandrost-5-ene-3α,7β,17β-triol, 17α-ethynylandrost-5-ene-3β,7α,17β-triol, 17α-ethynylandrost-5-ene-3β,17β-diol-7-one and analogs of these compounds where acetate ester or propionate ester is present at the 3-position. Other analogs of these compounds include ones where $R^7$ is —$C_2H_5$, e.g., 18-nor-18-ethyl-17α-ethynylandrost-5-ene-3β,7β, 11β, 17β-tetrol, 18-nor-18-ethyl-17α-ethynylandrost-5-ene-3α,7β, 11β, 17β-tetrol, 18-nor-18-ethyl-17α-ethynylandrost-5-ene-3β,7β,17β-triol, 18-nor-18-ethyl-17α-ethynylandrost-5-ene-3α,7β,17β-triol, 18-nor-18-ethyl-17α-ethynylandrost-5-ene-3β,7α,17β-triol and analogs of any of these compounds wherein an ester such as acetate ester or propionate ester is present at the 3-position. Other analogs of any of these compounds include ones wherein an ester such as acetate ester or propionate ester is present at the 7-position or at both the 3- and 7-positions, e.g., 3β-acetoxy-17α-ethynylandrost-5-ene-7β,17β-diol, 3β-acetoxy-17α-ethynylandrost-5-ene-7β, 11β,17β-triol or 7β-acetoxy-17α-ethynylandrost-5-ene-3β, 11β,17β-triol. Other compounds are described herein.

Treatment of metabolic disorders. In some claimed embodiments, the formula 1 compounds are used to treat, prevent or slow the progression of metabolic disorders such as type 1 diabetes, type 2 diabetes, Syndrome X, hypercholesterolemia, hyperglycemia, insulin resistance (e.g., associated with obesity or pre-diabetes), glucose intolerance, hypertriglyceridemia, hyperlipoproteinemia, a lipodystrophy condition, Syndrome X, arteriosclerosis, atherosclerosis and obesity. Syndrome X (including metabolic syndrome) is defined as a collection of two or more abnormalities including hyperinsulemia, obesity, elevated levels of triglycerides, uric acid, fibrinogen, small dense LDL particles and plasminogen activator inhibitor 1(PAI-1), and decreased levels of HDL-c.

Many patients who have insulin resistance but have not yet developed type 2 diabetes are also at a risk of developing metabolic syndrome, also referred to as syndrome X, insulin resistance syndrome or plurimetabolic syndrome. Syndrome-X typically occurs where a patient has two or more of hyperlipidemia, hyperinsulinemia, obesity, insulin resistance, insulin resistance leading to type-2 diabetes and diabetic complications thereof, i.e., diseases in which insulin resistance is the part of the pathophysiology.

Independent risk factors have been associated with cardiovascular disease associated with metabolic disorders can be treated with the F1Cs. These risk factors include hypertension, increased fibrinogen levels, high levels of triglycerides, elevated LDL cholesterol, elevated total cholesterol and low levels of HDL cholesterol. The treatment can result in stimulation of pancreatic β-cells to secrete more insulin and/or a slowed rate of loss of pancreatic β-cells that can occur over time in patients that have diabetes or that are obese.

In these claimed embodiments, treatment of metabolic disorders with a formula 1 compound can be combined with other treatments. Diabetes can be treated with a formula 1 compound and one or more of a variety of therapeutic agents including insulin sensitizers, such as PPAR-γ agonists such as glitazones; biguanides; protein tyrosine phosphatase-1B inhibitors; dipeptidyl peptidase IV inhibitors; insulin; insulin mimetics; sulfonylureas; meglitinides; α-glucoside hydrolase inhibitors; and α-amylase inhibitors. Metformin, phenformin, acarbose and rosiglitazone are agents that have been used to treat some type of diabetes.

As noted above, claimed embodiments may recite compositions containing a F1C to treat, prevent or slow the progression of insulin resistance or its symptoms. Insulin resistance is the diminished ability of insulin to exert its biological action across a broad range of concentrations producing less than expected biologic effect. Insulin resistant persons have a diminished ability to properly metabolize glucose and respond poorly, if at all, to insulin therapy. Symptoms of insulin resistance include insufficient insulin activation of glucose uptake, oxidation and storage in muscle and inadequate insulin repression of lipolysis in adipose tissue and of glucose production and secretion in cells. Insulin resistance can cause or contribute to polycystic ovarian syndrome, impaired glucose tolerance, gestational diabetes, hypertension, obesity and atherosclerosis. These F1C compositions can be used to reduce triglyceride levels in patients who are insulin resistant.

As described above, the invention embodiments include a method to identify a compound (or "test compound") with a potential to treat, slow the progression of, slow the onset of or ameliorate a metabolic disorder or a symptom thereof in a human or another mammal. The compounds identified by certain of the methods can be described as nonactivators of PPARs in vitro and incomplete NF-κB inhibitors in vitro that have one or more of the described activities, which are typically obtained from in vivo observations, e.g., delayed onset of hyperglycemia or slowed progression of an existing diabetes condition. Compounds with these characteristics are a new class of compounds that can be evaluated as agents to treat these disorders.

In these embodiments, the method comprises selecting a test compound that (i) does not activate one, two or three of PPAR-α, PPAR-γ and PPAR-δ in human or mammalian cells in vitro by more than about 10%, about 20%, about 30% or about 40% when compared to suitable negative control human or mammalian cells in vitro; (ii) inhibits or decreases the transcriptional activity or level of NF-κB by about 20-80% or about 25-75% or about 30-70% or about 35-65% in human or mammalian cells in vitro when compared to suitable negative control human or mammalian cells in vitro; (iii) when compared to a suitable negative control or normal control, decreases hyperglycemia, slows the progression or delays the onset of hyperglycemia, increases insulin sensitivity, decreases glucose intolerance, slows the progression or rate of loss of pancreatic β-islet cell numbers or their capacity to secrete insulin, increases pancreatic β-islet cell numbers or their capacity to secrete insulin, slows the rate of weight increase in db/db mice or mice with diet induced obesity, decreases elevated levels of triglycerides, decreases elevated levels total blood or serum cholesterol, decreases normal or elevated levels of LDL, VLDL, apoB-100 or apoB-48 in blood or serum or increases normal or low levels of HDL or apoA1 in blood or serum or decreases an elevated level of fibrinogen in blood or serum; and (iv) optionally, does not activate one or more of a glucocorticoid receptor, an androgen receptor an estrogen receptor-α, an estrogen receptor-β, a mineralcorticoid receptor, a progesterone receptor or a biologically active variant or isoform of any of these biomolecules in human or mammalian cells in vitro by more than about 5%, about 10%, about 20% or about 30% when compared to suitable negative control human or mammalian cells in vitro. This permits identification or at least partial characterization of compounds with a potential to treat or ameliorate the metabolic disorder in the mammal.

In some embodiments, the activity of the test compound can be compared to a suitable reference compound such as a formula 1 compound. The formula 1 compound can be used in the method as a positive control or a positive reference standard that conforms to the characteristics the method provides. Such compounds include 17α-ethynylandrost-5-ene-3β,7β,17β-triol, 17α-ethynylandrost-5-ene-3α,7β,17β-triol, 17α-ethynylandrost-5-ene-7β,17β-diol-3-one and androst-5-ene-3β,7β,16α,17β-tetrol. Other formula 1 compounds can be used as negative controls or reference standards that may exhibit none, one or two of the three required characteristics. Such compounds include 16α-bromoepiandrosterone, 16α-bromo-3β,17β-dihydroxyandrost-5-ene and 16α-hydroxyepiandrosterone.

Invention embodiments include determination of the effect of a test compound on one or more conditions or symptoms associated with a metabolic disorder or disease. Typically such determinations are compared to a suitable negative control or normal control or to a suitable positive control and the determination is conducted in a human or an animal in vivo, although the determination can sometimes be conducted in vitro in whole cells or cell lysates. Drug products, described below, can incorporate or include information from such determinations.

Decreases in hyperglycemia can be observed as a decrease in the level of blood or serum glucose to a normal fasting range, which for humans at least 2 years of age is about 70 mg/dL to 105 mg/dL or 115 mg/dL, with hyperglycemia being present at fasting glucose levels of about 135 mg/dL or about 140 mg/dL to 200 mg/dL, 300 mg/dL or 350 mg/dL. Glucose levels above about 400 mg/dL are life threatening. Postprandial glucose in blood or serum typically is measured at 2 hours after ingestion of carbohydrates, at least 75 g for humans, followed by a blood draw to measure glucose. Human glucose levels of 140 mg/dL to 200 mg/dL in postprandial blood or serum indicate a hyperglycemia condition and a glucose level above 200 mg/dL identifies human diabetes mellitus. For humans, typically in patients having a normal fasting glucose level of 70-115 mg/dL, an oral glucose tolerance test (OGTT) using blood can be conducted. In the OGTT for humans, if the peak glucose level (typically at 30 min or 1 hour after feeding) and 2 hour post carbohydrate values are above 200 mg/dL on two or more occasions, indicates that the patient has diabetes mellitus.

A surrogate for blood glucose in humans is measurement of glycosylated hemoglobin or Hb A1c, which is used, e.g., to monitor a diabetes treatment. Measurement of Hb A1c allows assessment of blood glucose or sugar levels over 100 to 120 days before the test and it is insensitive to short term variations such as a recent meal or fasting state. Hb A1c levels of 2.2-48% are normal in adults, while levels of 2.5-5.9% indicate good control of diabetes, levels of 6-8% indicate fair diabetes control and levels above 8% Hb A1c indicate poor control of a diabetes condition. Procedures to conduct and interpret these and related protocols have been described, e.g., K. D. Pagana and T. J. Pagana, Mosby's Diagnostic and Laboratory Test Reference, 5th edition, 2001, Mosby Inc., pages 441-448, 451-458, 507-509. Treatments with a formula 1 compound in some embodiments can be monitored by observing decreased Hb A1c, which correlates with improved diabetes treatment or improved glucose control.

Practice of the claimed methods or other methods described herein can result in normalization, e.g., return to levels within normal limits or ranges or near normal limits or ranges of glucose, glucose surrogate or other values such as levels of phase reactive proteins or lipid components such as total cholesterol, e.g., reduced LDL-cholesterol or increased HDL-cholesterol. Normalization of glucose or surrogate values is typically observed as an elevated glucose or surrogate level dropping to within about 1%, about 2%, about 3% or about 5% of a normal glucose level or within about 5% or about 8% of a normal glucose surrogate value. Glucose values for other species have been described and similar measurements or assays can be used in the invention methods for those species. Normalization of other values is typically observed as a return of an abnormally high or low level to within about 2% or about 4% to about 6%, about 10% or about 12% of the upper or lower end of the value's normal range for the subject species.

The compounds identified by the invention methods can be used to slow the progression or delay the onset of hyperglycemia or to increase insulin sensitivity in insulin resistance where these exist or are reasonably expected to develop. Other effects of the compounds include a decreased glucose intolerance, slowed progression or rate of loss of pancreatic β-islet cell numbers or their capacity to secrete insulin or increased pancreatic β-islet cell numbers or capacity to secrete insulin.

In some embodiments, the methods can be conducted in obese subjects. Obesity or "overweight" for humans as used herein generally refers to (1) an adult human male having a body mass index of about 26 kg/m$^2$, 27 kg/m$^2$, 28 kg/m$^2$, 29 kg/m$^2$, 30 kg/m$^2$, 31 kg/m$^2$, 32 kg/m$^2$ or greater and adult human females having a body mass index of at least about 26 kg/m$^2$, 27 kg/m$^2$, 28 kg/m$^2$, 29 kg/m$^2$, 30 kg/m$^2$, 31 kg/m$^2$, 32 kg/m$^2$ or greater or (2) an obese or overweight condition as assessed by a health care provider such as a physician or nurse. The determination of obesity for, e.g., a human, can take body fat content and distribution into account, since some persons with a high body mass index may not technically be obese due to a high amount of muscle tissue instead of fat or adipose tissue or due to a significant mounts of body fat or adipose in body areas other than the abdomen, e.g., hips or pelvis. Obesity and body mass index has been described, e.g., G. A. Colditz, Med. Sci. Sports Exerc., 31 (11), Suppl., pp. S663-S667, 1999, F. J. Nieto-Garcia et al., Epidemiology, 1(2):146-152, 1990, R. H. Eckel, Circulation, 96:3248-3250, 1999.

In some embodiments, the compounds identified by the invention methods do not significantly activate one or more of a mineralcorticoid receptor, a progesterone receptor, a glucocorticoid receptor, an androgen receptor an estrogen receptor-α, estrogen receptor-β or a biologically active variant of any of these biomolecules in human or mammalian cells in vitro by more than about 10%, about 20% or about 30% when compared to suitable negative control human or mammalian cells, typically as determined in and in vitro assay. Methods to measure these activities have been described, e.g., U.S. Pat. No. 5,298,429. In one exemplary method, an assay for evaluating whether a test compound is a functional ligand for a hormone receptor protein, or a functional engineered or modified form thereof comprising: (a) culturing cells which contain: non-endogenous DNA which expresses the hormone receptor protein, or functional engineered or modified form thereof, and DNA which encodes an operative hormone response element linked to a reporter gene, wherein the culturing is conducted in the presence of at least one test compound whose ability to function as a ligand or modulator for the hormone receptor protein, or functional engineered or modified form thereof, is sought to be determined, and (b) assaying for evidence of transcription of said reporter gene in said cells. This assay will typically be conducted using mammalian cells, e.g., CV-1 or COS cells. The reporter gene can be contained in a reporter plasmid where the non-endogenous DNA expresses the hormone receptor protein or functional modified form thereof is contained in an expression plasmid, wherein said reporter and expression plasmids also contain the origin of replication of SV-40. Also, the reporter gene can be contained in a reporter plasmid, wherein the non-endogenous DNA, which expresses the hormone receptor protein or functional modified form thereof, is contained in an expression plasmid, where the reporter and expression plasmids also contain a selectable marker. Related assays can use stably transfected cells with detectable reporter genes, e.g., as described for estrogen receptor-β (ERβ-UAS-bla GripTite™ cell-based Assay, Catalog Number K1091, Invitrogen Corp.), estrogen receptor-α (ERα-UAS-bla GripTite™ 293 cell-based Assay Catalog Number K1090, Invitrogen Corp.), androgen receptor (AR-UAS-bla GripTite™ 293 MSR cell-based Assay, Catalog Number K1082, Invitrogen Corp.) or progesterone receptor (Progesterone Receptor-UAS-bla HEK293T Assay, Catalog Number K1103, Invitrogen Corp.).

Claimed invention embodiments may include a method to identify or characterize a biological activity of a compound with a potential to treat or ameliorate a metabolic disorder in a mammal, comprising selecting a compound that (i) does not activate one, two or three of PPAR-α, PPAR-γ and PPAR-δ in human or mammalian cells in vitro by more than about 30% when compared to suitable negative control human or mammalian cells in vitro; (ii) inhibits or decreases the transcriptional activity or level of NF-κB by about 20-80% in human or mammalian cells in vitro when compared to suitable negative control human or mammalian cells in vitro; (iii) when compared to a suitable negative control or normal control, decreases hyperglycemia, slows the progression or delays the onset of hyperglycemia, increases insulin sensitivity, decreases glucose intolerance, slows the progression or rate of loss of pancreatic β-islet cell numbers or their capacity to secrete insulin, increases pancreatic β-islet cell numbers or their capacity to secrete insulin, slows the rate of weight increase in db/db mice or in subjects with diet induced or diet related obesity, decreases elevated levels of triglycerides, decreases elevated levels total blood or serum cholesterol, decreases normal or elevated levels of LDL, VLDL, apoB-100 or apoB-48 in blood or serum or increases normal or low levels of HDL or apoA1 in blood or serum or decreases an elevated level of fibrinogen in blood or serum; (iv) optionally, does not activate one or more of a glucocorticoid receptor, a mineralcorticoid receptor, a progesterone receptor, an androgen receptor an estrogen receptor-α, estrogen receptor-β or a biologically active variant of any of these biomolecules in human or mammalian cells in vitro by more than about 30% when compared to suitable negative control human or mammalian cells in vitro; and (v) optionally inhibits the level or activity of a phosphoenolpyruvate carboxykinase (PEPCK) or a 11β-hydroxysteroid dehydrogenase (11β-HSD), optionally 11β-HSD type 1 or 11β-HSD type 2 or the level of a mRNA that encodes PEPCK or a 11β-HSD, in hepatocytes or liver-derived cells in vitro or in liver cells or tissue obtained from liver cells or tissue in vivo; The method allows identification or characterization of the compound as having a potential to treat or ameliorate the metabolic disorder in human or another mammal. The PEPCK enzyme can be cytosolic or mitochondrial in origin.

In some embodiments, the formula 1 compounds that are used are characterized by having a lack of appreciable androgenicity. In these embodiments, the formula 1 compounds are characterized by having about 30% or less, about 20% or less, about 10% or less or about 5% or less of the androgenicity of an androgen such as testosterone, testosterone proprionate, dihydrotestosterone or dihydrotestosterone proprionate as measured in a suitable assay using suitable positive and/or negative controls. Suitable assays for androgenicity of various compounds have been described, e.g., J. R. Brooks, et al., *Prostate* 1991, 18:215-227, M. Gerrity et al., *Int. J. Androl.* 1981 4:494-504, S. S. Rao et al., *Indian J. Exp. Biol.* 1969 7:20-22, O. Sunami et al., *J. Toxicol. Sci.* 2000 25:403-415, G. H. Deckers et al., *J. Steroid Biochem. Mol. Biol.* 2000 74:83-92. The androgenicity of the formula 1 compounds are optionally determined as described or essentially as described in one or more of these assays or any suitable assay.

Thus, one such embodiment comprises a method to treat a condition described herein comprising administering to a subject in need thereof an effective amount of a formula 1 compound, or delivering to the subject's tissues an effective amount of a formula 1 compound, wherein the formula 1 compound has about 30% or less, about 20% or less, about 10% or less or about 5% or less of the androgenicity of an androgen such as testosterone, testosterone proprionate, dihydrotestosterone or dihydrotestosterone proprionate as measured in a suitable assay, e.g., as described in the citations above. In conducting such methods, the subjects or mammals, e.g., rodents, humans or primates, are optionally monitored for e.g., amelioration, prevention or a reduced severity of a disease, condition or symptom. Such monitoring can optionally include measuring one or more of cytokines (e.g., TNFα, IL-13, IL-1β), WBCs, platelets, granulocytes, neutrophils, RBCs, NK cells, macrophages or other immune cell types, e.g., as described herein or in the cited references, in circulation at suitable times, e.g., at baseline before treatment is started and at various times after treatment with a formula 1 compound such as at about 2-45 days after treatment with a formula 1 compound has ended.

Bone loss and repair conditions. Claimed embodiments may recite the use of a F1C or compositions containing a F1C and one or more excipients to treat, prevent, delay the onset of or slow the progression of bone loss, bone fracture or osteopenia disorders, e.g., an osteoporosis condition such as primary osteoporosis, postmenopausal or type 1 osteoporosis, involutional or type 2 osteoporosis, idiopathic osteoporosis, a secondary osteoporosis such as a glucocorticoid associated bone loss condition and bone loss associated with a trauma such as a first, second or third degree thermal, chemical or radiation burn. These treatments can improve bone mass, bone density and/or bone strength over time.

Drug products. In some embodiments, the invention provides a drug product for treating an inflammation, autoimmune or other condition described herein. The drug product typically comprises (a) the drug in a dosage form such as a solid or liquid formulation suitable for, e.g., oral or parenteral administration. Packaging for the drug and/or a package insert or label will have information about the drug's efficacy, mechanism of action, the intended patient population, dosage, dose regimen, route of administration, toxicity of the biological insult or the severity of insult that the drug can be used to treat, if this is known. When the biological insult is radiation exposure, the package insert or label can contain information about the radiation dose or dose range for which the drug product can be used or is approved. The drug product can optionally contain a diary or use instructions for the patient to record when or how the drug is used or what symptoms or drug effects the drug user experiences during or after use of the drug. This can be used to aid in phase IV or post marketing analyses of the drug's efficacy or side effects. Other embodiments of drug products are as described in other embodiments described herein.

A drug product as used herein means a product that has been reviewed and approved for marketing or sale by a regulatory agency or entity with authority to review or approve applications for sale or medical use, e.g., the U.S. Food and Drug Administration or the European Medicines Agency or European Medicines Evaluation Agency. Uses of drug products include its marketing or sales and offers to sell or buy it for consideration. These activities will typically adhere to terms of the regulatory approval that may affect or govern marketing, sales, purchases or product handling. The drug in a drug product can be a new drug, a generic drug, a biological, a medical device or a protocol for the use of any of these. The drug product usually results from marketing approval by the U.S. Food and Drug Administration or by the European Medicines Evaluation Agency of a U.S. or non-U.S. new drug application, an abbreviated new drug application, a biological license application or an application to market a medical device. Uses for the drug product include its sale to public or private buyers such as the U.S. Department of Defense, the U.S. Department of Energy, U.S. Department of Health and Human Services or a private drug buyer or distributor entity. Other uses include use of the drug to treat indicated or approved medical conditions and physician approved uses or off label uses. Pre-approval drug products are other aspects of the invention, which may be essentially the same as drug products described herein, but it can be used to prepare a drug or regulatory submission for marketing or for regulatory review before marketing approval.

The intended patient population identified by the drug product can also specify excluded populations, if any that may apply such as pediatric patients or elderly patients. Information about dosage will typically specify daily doses of the drug, while the dose regimen will describe how often and how long the drug is to be administered or taken. The route of administration will identify one or more routes that are suitable for use of the drug, although a given formulation will typically be approved for only one route of administration. Dosages, dose regimens and routes of administration that the package or label may identify are described elsewhere herein.

In one embodiment, the drug product is for treatment, prevention or amelioration of an inflammation condition or another condition described herein and it comprises or includes a formulation that contains a compound such as a formula 1 compound formulated with 1, 2, 3, 4 or more excipient(s) for oral or parenteral administration, e.g., intramuscular, subcutaneous or subdermal injection, with a package insert or label describing administration of a daily dose of, e.g., about 0.01 mg, 0.05 mg, 0.1 mg, 0.5 mg, 1 mg, 4 mg, 5 mg, 10 mg, 20 mg, 25 mg, 40 mg, 50 mg, 80 mg, 100 mg, 150 mg, 175 mg, 200 mg, 225 mg, 250 mg, 300 mg, 350 mg, 400 mg, 450 mg or 500 mg of a formula 1 compound for 1, 2, 3, 4, 5, 6, 7, 8, 9, 10 or more consecutive days beginning after the disease or condition is diagnosed or otherwise observed. Information that the package insert or label can contain includes information about biological responses to the drug or the treatment regimen. The information can include a description of one or more of (a) one or more side-effects or toxicities associated with use of the drug in humans or mammals such as non-human primates, (b) its effect on the inflammation or other condition, e.g., in a protocol or suitable variation described herein, (c) protocols or instructions for the use of additional therapeutic agents such as dexamethasone or other glucocorticoids with the drug and (d) the time or time period when administration of the drug should begin for best or known therapeutic benefit.

T cell subset regulation. In some aspects, the invention provides a method to identify a compound with a potential to detectably modulate the numbers or activity of $CD4^+CD25^+$ regulatory T cells, $CD4^+CD25^+CD103^+$ regulatory T cells, $CD4^+CD25^{high}CD103^+$ regulatory T cells or $CD4^+CD25^{high}$ regulatory T cells in a mammal, comprising selecting a compound that (i) does not activate or inhibit one or more of a glucocorticoid receptor, an androgen receptor an estrogen receptor-$\alpha$, estrogen receptor-$\beta$ or a biologically active variant of any of these biomolecules in human or mammalian cells in vitro by more than about 20% or about 30% when compared to suitable control human or mammalian cells in vitro; (ii) has a molecular weight of about 100-1000 Daltons, optionally a molecular weight of about 250-850 Daltons; (iii) when compared to a suitable negative control or normal control, increases or decreases the numbers or activity of $CD4^+CD25^+$ regulatory T cells, $CD4^+CD25+CD103^+$ regulatory T cells, $CD4^+CD25^{high}CD103^+$ regulatory T cells or $CD4^+CD25^{high}$ regulatory T cells by more than 20% in a suitable assay; and (iv) optionally inhibits or decreases the transcriptional activity or level of NF-κB by about 20-80% in human or mammalian cells in vitro when compared to suitable negative control human or mammalian cells in vitro. The formula 1 compounds and other compounds can be used in these embodiments essentially as described in examples 20 or 21 below.

Compounds in vitro or in vivo that increase or decrease the activity or numbers of certain T cell subsets such as $CD4^+CD25^+$ T cells and $CD4^+CD25^{high}$T cells are candidates for treating or slowing the onset or progression of autoimmune conditions, cancer, neurological trauma or disorders such as neuron loss after a trauma such as ischemia and metabolic diseases such as type I diabetes, atherosclerosis, cell, organ or tissue rejection in autologous transplantations and graft versus host disease in situations there these conditions exist or may occur. The treatments can be used for improving wound healing, treating reperfusion injury, stenosis, restenosis after angioplasty, myocardial or cerebral infarction. Embodiments include compounds having a molecular weight of less than about 2,000 Daltons, less than about 1,000 Daltons or less than about 500 Daltons. One group of compounds has a molecular weight of about 285 or 290 to about 500 or 650 Daltons. Treg cell responses can be observed as an increase or decrease of about 5%, about 10%, about 15%, about 20%, about 25%, about 30%, about 35%, about 40%, about 45%, about 50%, about 60%, about 70%, about 80%, about 100%, about 200%, about 400%, about 600%, about 1000%, about 2000%, about 5000%, about 10000% or more in the numbers of Treg cells, typically $CD4^+CD25^+$ T cells or $CD4^+CD25^{high}$ T cells, in subjects or in in vitro assays treated with compound compared to suitable negative controls. These changes can be observes as increases or decreases in Treg cell numbers or their activity in circulating blood or in cells in vitro or in vivo.

Methods to analyze subset cell profiles such as T cell profiles can be obtained by any of a variety of methods including flow cytometry (FACS), for example, Levy et al., *Clin. Immunol. Immunopathol.* 35:328, 1985. In FACS analysis, monoclonal antibodies to a variety of subset cells bind to and identify phenotypic surface antigens that are present on the cells. Commercially available antibodies exist that can detect the presence of these markers, so that preparation of the antibodies is generally not required. Antibodies that identify the same or a closely linked antigenic marker would be expected to give similar diagnostic results. Thus, where a marker antigen is designated in the specification or claims by reference to a particular monoclonal antibody with which it binds, e.g., CD4 or CD25, such a designation includes that marker even if different monoclonal antibodies are used in the identification. Phenotypic markers of interest include general markers for various subset cell types including CD3 for total T cells, CD4 for T helper/inducer cells, CD8 for T suppressor/cytotoxic cells, and CD16/56 for NK cells; CD8-expressing subset markers such as CD11b for T suppressor cells, CD38 for activated T suppressor/cytotoxic cells, HLA-DR for activated T suppressor/cytotoxic cells, and CD57; and CD4 expressing markers such as CD25 and HLA-DR for activated T helper/inducer cells, including Treg cells.

Dosing protocols or methods. In treating any of the conditions or symptoms disclosed herein, one can continuously (daily) or intermittently administer the formula 1 compound (s) to a subject suffering from or susceptible to the condition or symptom. In treating a condition such as an inflammation condition or another condition disclosed herein with a formula 1 compound intermittent dosing could avoid or ameliorate some of the undesired aspects normally associated with discontinuous dosing. Such undesired aspects include failure of the patient or subject to adhere to a daily dosing regimen or reduction of the dosages of other therapeutic agents such as glucocorticoids and/or their associated unwanted side effects or toxicities such as bone loss or resorption.

In some embodiments, daily dosing will continue as long as the disease or symptoms are apparent, typically for chronic conditions. In other embodiments, daily dosing will continue for 1, 2, 3, 4, 5, 6, 7, 8, 9 or 10 consecutive days and then be followed by a period of no dosing until or if dosing is again needed. These embodiments will typically involve treating acute conditions that may or may not recur from time to time. Treatment of chronic conditions will typically involve continuous daily dosing for extended periods of time.

In any of continuous (daily) or intermittent dosing regimen, or in treating any of the diseases, conditions or symptoms described herein, the formula 1 compound(s) can be administered by one or more suitable routes, e.g., oral, buccal, sublingual, topical, intramuscular, subcutaneous, subdermal, intravenous, intradermal or by an aerosol.

The daily dose is usually about 0.001 mg/kg/day to about 200 mg/kg/day. Typical dose ranges are about 0.1 to about 100 mg/kg/day, including about 0.2 mg/kg/day, 0.5 mg/kg/day, about 1 mg/kg/day, about 2 mg/kg/day, about 4 mg/kg/day, about 5 mg/kg/day or about 6 mg/kg/day. One can administer the formula 1 compound(s) orally or by parenteral administration using about 2 to about 50 mg/kg/day or about 2-40 mg/kg/day. Such dosing will typically give a serum level of the formula 1 compound of about 1 mg/mL, about 4 mg/mL or about 8 mg/mL to about 125 mg/mL or about 250 mg/mL, e.g., about 15 mg/mL to about 120 mg/mL or about 20 mg/mL to about 100 mg/mL. Such a serum level can be transient, e.g., lasting about 30 minutes or about 60 minutes to about 2 hours or about 8 hours, which will may occur on days when the compound is administered or at later time for depot formulations. For humans or other mammals an oral or parenteral daily dose will typically be about 0.01 mg, 0.05 mg, 0.1 mg, 0.5 mg, 1 mg, 4 mg, 5 mg, 10 mg, 20 mg, 25 mg, 40 mg, 50 mg, 80 mg, 100 mg, 150 mg, 175 mg, 200 mg, 225 mg, 250 mg, 300 mg, 350 mg, 400 mg, 450 mg or 500 mg of a formula 1 compound, which can be present as a unit dosage, e.g., tablets, capsules, or other forms for oral administration. Such daily doses can often be about 5 mg/day to about 250 mg/day.

Continuous daily dosing is usually used to treat the chronic conditions described herein. Daily doses are usually given as a single dose, but daily doses can be subdivided into 2 or 3 subdoses. Intermittent dosing protocols include administration of a formula 1 compound every other day or every third day for a suitable time period. When treating blood cell deficiencies dosing will usually begin on the same day that the subject experiences a short-lived myeloablative event such as a radiation exposure. For longer lasting events, e.g., cancer chemotherapy, dosing with the formula 1 compound can begin at about 12 hours, about 1 day, about 2 days or 3 about days after a chemotherapy agent has been administered to the subject. Daily dosing can continue for defined periods followed by no dosing for a fixed or variable period of time. In these embodiments, a disease flare such as a multiple sclerosis, optic neuritis, arthritis, asthma, a colitis condition such as ulcerative colitis or Crohn's disease flare can be treated by daily dosing for about 3, 5, 7, 14 or 28 consecutive days, followed by no further treatment until another flare occurs or begins.

Clinical conditions and symptoms. Claimed embodiments may recite the compounds and methods described herein to treat, ameliorate, prevent or slow the progression of conditions described herein and/or one or more of their symptoms. Such uses include inhibiting bone resorption, decreasing unwanted side effects associate with or caused by a chemotherapy, e.g., antiinflammatory glucocorticoids. Unwanted inflammation conditions include lung inflammation conditions, e.g., lung fibrosis, emphysema, cystic fibrosis, acute or chronic asthma, bronchial asthma, atopic asthma, ARDS or COPD, or autoimmune disorders such as osteoarthritis, rheumatoid arthritis, a pancreatitis such as autoimmune pancreatitis, systemic lupus erythematosis, lupus erythematosus-related tissue inflammation, lupus erythematosus-related arthritis, lupus erythematosus-related skin changes, lupus erythematosus-related hematologic abnormalities, lupus erythematosus-related kidney impairment, lupus erythematosus-related heart or lung disease, and unwanted lupus erythematosus-related neuropsychiatric or neurological changes.

Symptoms of conditions that can be treated include fever, joint pain (arthralgias), arthritis, and serositis (pleurisy or pericarditis). Administration of other agents can also be used in the present treatments. Thus, pain can be treated using nonsteroidal, anti-inflammatory drugs, such as aspirin, salisylates, ibuprofen, naproxen, clinoril, oxaprozin and tolmetin. Cutaneous features of systemic lupus can be treated with antimalarial drugs, such as hydroxychloroquine, chloroquine and quinacrine. Retinoids such as istretinoin and etretinate can also be used to treat skin symptoms in combination with the compounds described herein. Organ damage can be treated with corticosteroids, usually given orally or intravenously. Corticosteroids that can be used include hydrocortisone (cortisol), corticosterone, aldosterone, ACTH, triamcinolone and derivatives such as triamcinolone diacetate, triamcinolone hexacetonide, and triamcinolone acetonide, betamethasone and derivatives such as betamethasone dipropionate, betamethasone benzoate, betamethasone sodium phosphate, betamethasone acetate, and betamethasone valerate, flunisolide, prednisone and its derivatives, fluocinolone and derivatives such as fluocinolone acetonide, diflorasone and derivatives such as diflorasone diacetate, halcinonide, dexamethasone and derivatives such as dexamethasone dipropionate and dexamethasone valerate, desoximetasone (desoxymethasone), diflucortolone and derivatives such as diflucortolone valerate), fluclorolone acetonide, fluocinonide, fluocortolone, fluprednidene, flurandrenolide, clobetasol, clobetasone and derivatives such as clobetasone butyrate, alclometasone, flumethasone, and fluocortolone.

When oral administration of corticosteroids is insufficient, intravenous methyl prednisolone pulse therapy (high dose) can be used to treat lupus nephritis and other serious non-renal manifestations, such as hemolytic anemia, central nervous system inflammation (cerebritis), low-platelet counts, and severe pleuropericarditis.

The formula 1 compounds can be used to treat, prevent or slow the progression of osteoporosis or bone fractures. The treatment of subjects can lead to strengthening of bones and/or reduced loss of bone mass or minerals, resulting in increased resistance to fractures. As used herein, "treating" conditions such as those described herein means that the treatment can result in amelioration, prevention or slowed progression of the conditions, and/or amelioration, prevention or slowed progression of one or more symptoms of such conditions.

Formulations and compositions for preparing formulations. Claimed invention embodiments may include formulations described here and elsewhere in this disclosure. While it is possible for the formula 1 compound(s) to be administered alone it is usual to present them as formulations. The formulations, both for veterinary and for human use, comprise at least one formula 1 compound, together with one or more excipients and optionally one or more additional therapeutic ingredients. Usually only one F1C is present in the composition, with only low, trace or essentially undetectable levels (less than about 3% by weight or less than about 2% of total F1C) of other F1Cs, e.g., one or more epimers of the primary F1C.

Formulations include compositions comprising 1, 2, 3, 4 or more pharmaceutically acceptable excipients or carriers. The compositions are used to prepare formulations suitable for human or animal use. Suitable administration routes for formulations include oral, rectal, nasal, topical (including buccal and sublingual), vaginal, rectal and parenteral (including subcutaneous, intramuscular, intravenous, intradermal, intrathecal, intraocular and epidural). In general, aqueous and non-aqueous liquid or cream formulations are delivered by a parenteral, oral or topical route. In other embodiments, such as the invention intermittent dosing methods, the formula 1 compound(s) may be present as an aqueous or a non-aqueous liquid formulation or a solid formulation suitable for administration by any of the routes disclosed herein, e.g., oral, topical, buccal, sublingual, parenteral, inhaled aerosol or a depot such as a subcutaneous depot or an intraperitoneal or intramuscular depot. It will be appreciated that the preferred route may vary with, for example, the subject's pathological condition or weight or the subject's response to therapy with a formula 1 compound or other therapy that is used or that is appropriate to the circumstances.

The formulations include those suitable for the foregoing administration routes. The formulations may conveniently be presented in unit dosage form and may be prepared by any of the methods known in the art of pharmacy. Techniques, excipients and formulations generally are found in, e.g., *Remington's Pharmaceutical Sciences*, Mack Publishing Co., Easton, Pa. 1985, 17$^{th}$ edition, Nema et al., *PDA J. Pharm. Sci. Tech.* 1997 51:166-171, G. Cole, et al., editors, *Pharmaceutical Coating Technology,* 1995, Taylor & Francis, ISBN 0 136628915, H. A. Lieberman, et al., editors, *Pharmaceutical Dosage Forms,* 1992 2$^{nd}$ revised edition, volumes 1 and 2, Marcel Dekker, ISBN 0824793870, J. T. Carstensen. *Pharmaceutical Preformulation,* 1998, pages 1-306, Technomic Publishing Co. ISBN 1566766907. Exemplary excipients for formulations include emulsifying wax, propyl gallate, citric acid, lactic acid, polysorbate 80, sodium chloride, isopropyl palmitate, glycerin, white petrolatum and other excipients disclosed herein.

Formulations, or compositions disclosed herein for use to make formulations suitable for administration by the routes disclosed herein optionally comprise an average particle size in the range of about 0.01 to about 500 microns, about 0.1 to about 100 microns or about 0.5 to about 75 microns. Average particle sizes include a range between 0.01 and 500 microns in 0.05 micron or in 0.1 micron or other increments, e.g., an average particle size of about 0.05, 0.1, 0.5, 1, 1.5, 2.0, 2.5, 3.0, 3.5, 4.0, 4.5, 5.0, 5.5, 6, 7, 8, 9, 10, 15, 20, 25, 30, 35, 40, 50, 60, 75, 85, 100, 120, etc. microns). When formula 1 compounds or compositions that comprise a formula 1 compound are used as intermediates to make a formulation, they may comprise one, two, three or more of these average particle sizes, or size ranges. In preparing any of the compositions or formulations that are disclosed herein and that comprise a formula 1 compound (and optionally one or more excipients), one may optionally mill, sieve or otherwise granulate the compound or composition to obtain a desired particle size.

Thus, one such embodiment comprises a method to treat a condition described herein comprising administering to a subject in need thereof an effective amount of a formula 1 compound, or delivering to the subject's tissues an effective amount of a formula 1 compound, wherein the formula 1 compound has about 30% or less, about 20% or less, about 10% or less or about 5% or less of the androgenicity of an androgen such as testosterone, testosterone proprionate, dihydrotestosterone or dihydrotestosterone proprionate as measured in a suitable assay, e.g., as described in the citations above. In conducting such methods, the subjects or mammals, e.g., rodents, humans or primates, are optionally monitored for e.g., amelioration, prevention or a reduced severity of a disease, condition or symptom. Such monitoring can optionally include measuring one or more of cytokines (e.g., TNFα, IL-13, IL-1β), WBCs, platelets, granulocytes, neutrophils, RBCs, NK cells, macrophages or other immune cell types, e.g., as described herein or in the cited references, in circulation at suitable times, e.g., at baseline before treatment is started and at various times after treatment with a formula 1 compound such as at about 2-45 days after treatment with a formula 1 compound has ended.

As noted above, in some embodiments a treatment with a formula 1 compound is combined with a corticosteroid or glucocorticoid. Corticosteroids are used in a number of clinical situations to, e.g., decrease the intensity or frequency of flares or episodes of inflammation or autoimmune reactions in conditions such as acute or chronic rheumatoid arthritis, acute or chronic osteoarthritis, a colitis condition such as ulcerative colitis, acute or chronic asthma, bronchial asthma, psoriasis, systemic lupus erythematosus, hepatitis, pulmonary fibrosis, type I diabetes, type II diabetes or cachexia. However, many corticosteroids have significant side effects or toxicities that can limit their use or efficacy. The formula 1 compounds are useful to counteract such side effects or toxicities without negating all of the desired therapeutic capacity of the corticosteroid. This allows the continued use, or a modified dosage of the corticosteroid, e.g., an increased dosage, without an intensification of the side effects or toxicities or a decreased corticosteroid dosage. The side-effects or toxicities that can be treated, prevented, ameliorated or reduced include one or more of bone loss, reduced bone growth, enhanced bone resorption, osteoporosis, immunosuppression, increased susceptibility to infection, mood or personality changes, depression, headache, vertigo, high blood pressure or hypertension, muscle weakness, fatigue, nausea, malaise, peptic ulcers, pancreatitis, thin or fragile skin, growth suppression in children or preadult subjects, thromboembolism, cataracts, and edema. Dosages, routes of administration and dosing protocols for the formula 1 compound would be essentially as described herein. An exemplary dose of formula 1 compound of about 0.5 to about 20 mg/kg/day is administered during the period during which a corticosteroid is administered and optionally over a period of about 1 week to about 6 months or more after dosing with the corticosteroid has ended. The corticosteroids are administered essentially using known dosages, routes of administration and dosing protocols, see, e.g., *Physicians Desk Reference* 54$^{th}$ edition, 2000, pages 323-2781, ISBN 1-56363-330-2, Medical Economics Co., Inc., Montvale, N.J. However, the dosage of the corticosteroid may optionally be adjusted, e.g., increased about 10% to about 300% above the normal dosage, without a corresponding increase in all of the side effects or toxicities associated with the corticosteroid. Such increases would be made incrementally over a sufficient time period and as appropriate for the subject's clinical condition, e.g., daily corticosteroid dose increases of about 10% to about 20% to a maximum of about 300% over about 2 weeks to about 1 year.

The treatment method can be used to, treat, prevent or ameliorate an acute trauma such as a myocardial infarction, a hemorrhage such as a cerebral hemorrhage or stroke or a bone fracture, osteoporosis or excess or unwanted bone resorption or loss. The treatments can be used to facilitate repair of damage or injury to skin, mucosa, cartilage, liver, heart tissue, bone or CNS or neural tissue in situations where there is damage, e.g., chemical or heat burns, osteoarthritis, rheumatoid arthritis, liver cirrhosis, osteoporosis, bone fracture, myocardial infarction, stroke or head trauma. The treatments can also be used to reduce bone loss due to a therapy, e.g., a glucocorticoid therapy in a lupus condition or in patients having an inflammatory bowel disease, Crohn's disease, acute or chronic colitis or a renal disorder such as acute or chronic renal failure or autoimmune renal injury.

The following embodiments describe one or more aspects of the invention.

1. A method to identify or characterize a biodynamic compound comprising, measuring a biological response of a test compound in vivo in a subject after exposure of the subject to an acute stimulus or biological insult that elicits a detectable response to the acute stimulus or biological insult, wherein the test compound elicits a favorable treatment response on a mediator of the acute biological response to the stimulus or biological insult at a time or time period when (i) the acute response is maximal or nearly maximal or (ii) the acute response is increasing in a period of a prolonged acute biological response and wherein the favorable treatment response differs at time (i) or (ii) from its effect on the mediator of the acute biological response at one, two, three or more earlier or later times or time periods and such effect at the earlier or later times or time periods is an increase or decrease of less than about 50% in the level or activity of the mediator of the acute biological response when compared to suitable vehicle or placebo controls at the same or essentially the same earlier or later times or time period, whereby a compound that elicits a favorable treatment response on the mediator of the acute biological response and the favorable treatment response differs at time (i) or (ii) from its effect on the mediator of the acute biological response at one, two, three or more earlier or later times or time periods is identified as a biodynamic compound.

2. The method of embodiment 1 further comprising conducting a protocol to determine if the test compound modulates the activity or level of the mediator of the acute biological response by about 25% to about 75% in an assay in vitro, optionally wherein the test compound does not activate or antagonize a glucocorticoid receptor by more than about 20% when compared to a suitable reference activator or antagonist of the glucocorticoid receptor.

3. The method of embodiment 1 or 2 wherein the acute stimulus or biological insult is exposure of the subject to a sufficient amount of ionizing radiation or a proinflammatory signal, compound or composition, optionally wherein the proinflammatory signal, compound or composition is bacterial LPS or TNFα, and/or optionally wherein the mediator of the acute biological response is NF-κB or IκB.

4. The method of embodiment 1, 2 or 3 wherein the acute stimulus or biological insult is administration of sufficient bacterial LPS to a sufficient number of drug treated mice and a sufficient number vehicle control mice and measurement of the effect of the test compound on the mediator of the acute biological response at a time when (i) the acute response is maximal or nearly maximal, optionally at about 1.5 hours after administration of bacterial LPS by intraperitoneal injection and (ii) one or two other time points before and/or after the administration of the sufficient bacterial LPS, optionally at one time point before the administration of the sufficient bacterial LPS and at one later time after the acute response is maximal or nearly maximal, optionally at about 2.0 or 2.5 hours after administration of bacterial LPS by intraperitoneal injection, and optionally wherein the mediator of the acute biological response is NF-κB or IκB.

5. The method of embodiment 4 wherein the administration of sufficient bacterial LPS is accomplished essentially according to the method described at example 9 or a suitable variation thereof and optionally wherein the capacity of the compound to partially modulate the level or activity of the mediator of the acute biological response is accomplished essentially according to the method described at example 7 or a suitable variation thereof.

6. The method of embodiment 1, 2, 3, 4 or 5 comprising inclusion of a positive biodynamic drug control, optionally 17α-ethynylandrost-5-ene-3β,7β,17β-triol, to assess the relative potency or efficacy of the test compound and optionally including biostatic drug control to assess the relative potency or efficacy of the test compound.

7. A drug product or pre-approval drug product comprising a drug in a dosage form and packaging for the drug together with a package insert or label that includes information about the drug's efficacy, mechanism of action or clinical use, wherein the efficacy, mechanism of action or clinical use information was obtained at least in part from a characterization method that comprises the method of embodiment 1, 2, 3, 4 or 5.

8. A drug product or pre-approval drug product comprising a drug in a dosage form and packaging for the drug together with a package insert or label that includes information about the drug's efficacy, mechanism of action or clinical use, wherein the efficacy, mechanism of action or clinical use information was obtained at least in part from a characterization method that comprises (a) contacting a cell or cells in vitro for a sufficient time with a sufficient amount of an activator of NF-κB activity wherein the cell(s) can respond to the activator of NF-κB by detectably increasing the level or activity of NF-kB in the cell(s); (b) contacting the cell(s) in vitro for a sufficient time with a sufficient amount of the drug, wherein the drug detectably inhibits the activation of NF-κB activity compared to suitable control; and (c) optionally comparing the drug's capacity to inhibit activation of NF-kB with a reference compound, wherein the reference compound is a formula 1 compound described herein that has the capacity to detectably inhibit activation of NF-κB in the characterization method by about 25% to about 75%, wherein the drug inhibits activation of NF-kB by about 25% to about 75% in the characterization method and optionally wherein the reference compound or the drug does not detectably or significantly bind directly to a glucocorticoid receptor or optionally wherein the reference compound or the drug does not detectably or significantly agonize a glucocorticoid receptor, optionally the drug does not agonize a glucocorticoid receptor by more than about 20% compared to a suitable agonist control.

9. The drug product of embodiment 7 or 8 wherein the dosage form comprises an oral, parenteral, topical or inhalation formulation.

10. The drug product of embodiment 8 or 9 wherein the reference compound or the drug inhibits activation of NF-kB by about 35% to about 70% or by about 40% to about 65% in the characterization method.

11. The drug product of embodiment 8, 9 or 10 wherein the NF-κB in the cells is activated by one, two, three or more of TNF-α, TNF-β, TGF-β, IL-1, epidermal growth factor, bacterial LPS, bacterial peptidoglycan, yeast zymosan, bacterial lipoprotein, a bacterial or viral antigen or gene product, ultraviolet irradiation, heat or a temperature increase, a lymphokine or an oxidant free radical, or $H_2O_2$.

12. The drug product of embodiment 8, 9, 10 or 11 wherein the reference compound or the drug binds directly to a glucocorticoid receptor with a $k_d$ of >10 μM in a suitable binding assay or wherein the reference compound or the drug does not detectably agonize a glucocorticoid receptor at a concentration of equal to or greater than about 10 μM in an assay suitable to detect activation or an increase of glucocorticoid receptor-mediated gene expression.

13. The drug product of embodiment 8, 9, 10, 11 or 12 wherein the cell(s) in vitro are mammalian, rodent or human cell(s) optionally selected from the group consisting of human THP-1 cells, rat RAW cells, macrophages, monocytes, T-lymphocytes, B-lymphocytes, dendritic cells, glial cells, Kupfer cells, hepatocytes, neutrophils, white blood cells and cells from whole blood.

14. The drug product of embodiment 7 or 8 wherein the information about the drug's efficacy, mechanism of action or clinical use is included in a submission to a regulatory agency or a review entity with authority to review or approve the commercial use or marketing of the drug product.

15. A method to treat an inflammation condition or autoimmune disease in a mammal, comprising administering to the subject, or delivering to the subject's tissues, an effective amount of a biodynamic compound identified by the method of embodiment 1, 2, 3, 4, 5 or 6, wherein a positive biodynamic compound is used as a reference standard or wherein the biodynamic compound partially inhibits the mediator of the acute biological response in a suitable assay in vitro, wherein the suitable assay in vitro optionally is essentially according to the method of example 7 or a suitable variation thereof.

16. A compound having the structure

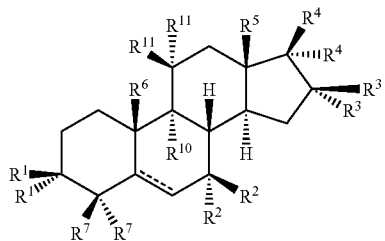

wherein one $R^1$ is —H or $C_{1-8}$ optionally substituted alkyl and the other $R^1$ is —OH, a $C_{2-8}$ ester or a $C_{1-8}$ ether or both $R^1$ together are =O; one $R^2$ is —H or $C_{1-8}$ optionally substituted alkyl and the other $R^2$ is —H, —OH, a $C_{2-8}$ ester or a $C_{1-8}$ ether or both $R^2$ together are =O; one $R^3$ is —H or $C_{1-8}$ optionally substituted alkyl and the other $R^3$ is —OH, a $C_{2-8}$ ester, a $C_{1-8}$ ether or $C_{1-8}$ optionally substituted alkyl; one $R^4$ is —H or $C_{1-8}$ optionally substituted alkyl, preferably —$CH_3$, —C≡CH or —C≡C—Cl, and the other $R^4$ is —OH, a $C_{2-8}$ ester or a $C_{1-8}$ ether; $R^5$ is —$CH_3$, —$C_2H_5$ or —$CH_2OH$; $R^5$ is —H, —$CH_3$, —$C_2H_5$ or —$CH_2OH$; one $R^7$ is —H or $C_{1-8}$ optionally substituted alkyl and the other $R^7$ is —H, —OH, a $C_{2-8}$ ester or a $C_{1-8}$ ether; $R^{10}$ is —H or a halogen; and one $R^{11}$ is —H or $C_{1-8}$ optionally substituted alkyl and the other $R^{11}$ is —H, —OH, a $C_{2-8}$ ester, a $C_{1-8}$ ether or $C_{1-8}$ optionally substituted alkyl. The compound(s) in this embodiment and those below can be partially purified, e.g., ≧ about 70% or ≧ about 80% pure by weight compared to other F1Cs, or more highly purified, ≧ about 90% or ≧ about 95% or ≧ about 97% pure by weight compared to other F1Cs. These compounds can be used in one or more of the embodiments described herein.

17. The compound according to embodiment 16 wherein one, two or three of $R^2$, $R^7$ or $R^{11}$ is —OH, a $C_{2-8}$ ester, a $C_{1-8}$ ether, =O or =NOH.

18. The compound according to embodiment 16 or 17 selected from 17α-ethynylandrost-5-ene-3β,7β,17β-triol, 17α-ethynylandrost-5-ene-3α,7β,17β-triol, 17α-ethynylandrost-5-ene-3β,17β-diol-7-one, 17α-ethynylandrost-5-ene-7β,17β-diol-3-one, 17α-ethynylandrost-5-ene-3β,7β,16α,17β-tetrol, 17α-ethynylandrost-5-ene-3α,7β,16α,17β-tetrol, 17α-ethynylandrost-5-ene-3β,7α,16α,17β-tetrol, 17α-ethynylandrost-5-ene-3β,4β,16α,17β-tetrol, 17α-ethynylandrost-5-ene-3α,4β,16α,17β-tetrol, 17α-ethynylandrost-5-ene-3β,11β,16α,17β-tetrol, 17β-ethynylandrost-5-ene-3α,11β,16α,17α-tetrol, 17β-ethynylandrost-5-ene-3α,11β,16β,17α-tetrol, androst-5-ene-3α,11β,16β,17β-tetrol or a $C_{2-4}$ monoester or $C_{2-4}$ diester analog of any of these compounds, optionally wherein (1) the $C_{2-4}$ monoester is acetate or propionate at the 3- or 17-position or (2) the $C_{2-4}$ diester is acetate or propionate at the 3- and 17-positions. Other analogs include compounds wherein the ethynyl moiety at the 17-position is replaced with chloroethynyl, e.g., 17α-chloroethynylandrost-5-ene-3β,7β,17β-triol, 17α-chloroethynylandrost-5-ene-3α,7β,17β-triol and 17α-chloroethynylandrost-5-ene-7β,17β-diol-3-one.

19. The compound according to embodiment 17 or 18 wherein the compound is (a) a powder or granule that is at least 80% pure, at least 95% pure or at least 98% pure or (b) a solution or suspension that is at least 80% pure, at least 95% pure or at least 98% pure. These compounds include 17α-ethynylandrost-5-ene-3β,7β,17β-triol, androst-5-ene-3β,4β,16α,17β-tetrol, 17α-ethynylandrost-5-ene-3β,4β,16α,17β-tetrol, androst-5-ene-3β,11β,16α,17β-tetrol, androst-5-ene-3β,7β,16α,17β-tetrol and epimers of these compounds wherein the configuration of one or two hydroxyl groups is changed from α- to β- or from β- to α-, e.g., 17β-ethynylandrost-5-ene-3β,7β,17α-triol, 17β-ethynylandrost-5-ene-3β,4β,16α,17α-tetrol, 17α-ethynylandrost-5-ene-3α,7β,17β-triol or 17α-ethynylandrost-5-ene-3α,4β,16α,17β-tetrol.

20. The compound according to embodiment 17, 18 or 19 wherein the compound is about 80%, about 85%, about 90%, about 95%, about 97% or about 98% to about 99.5% or about 99.9% pure, optionally wherein the compound is in the form of a powder or granules, optionally wherein the powder has an average particle size of about 50 nm or about 100 nm to about 5 μm, about 10 μm or about 25 μm as measured in a suitable assay such as light scattering.

21. A method to identify a compound with a potential to detectably modulate the numbers or activity of CD4$^+$CD25$^+$ regulatory T cells, CD4$^+$CD25$^+$CD103$^+$ regulatory T cells, CD4$^+$CD25$^{high}$CD103$^+$ regulatory T cells or CD4$^+$CD25$^{high}$ regulatory T cells in a mammal, comprising selecting a compound that (i) does not activate or inhibit one or more of a glucocorticoid receptor, an androgen receptor an estrogen receptor-α, estrogen receptor-β or a biologically active variant of any of these biomolecules in human or mammalian cells in vitro by more than about 30% when compared to suitable control human or mammalian cells in vitro; (ii) has a molecular weight of about 100-1000 Daltons, optionally a molecular weight of about 250-850 Daltons; (iii) when compared to a suitable negative control or normal control, increases or decreases the numbers or activity of CD4$^+$CD25$^+$ regulatory T cells, CD4$^+$CD25$^+$CD103$^+$ regulatory T cells, CD4$^+$CD25$^{high}$CD103$^+$ regulatory T cells or CD4$^+$CD25$^{high}$ regulatory T cells by more than 20% in a suitable assay; and (iv) optionally inhibits or decreases the transcriptional activity or level of NF-κB by about 20-80% in human or mammalian cells in vitro when compared to suitable negative control human or mammalian cells in vitro; whereby the compound is identified. This method is optionally conducted using one or more reference compounds such as a compound of embodiment 16, 17, 18, 19 or elsewhere, e.g., at paragraph 40, 41 or 42, as (1) a reference standard or control or (2) the compound to be tested itself, optionally as compared to a different compound of embodiment 16, 17, 18, 19 or elsewhere, e.g., at paragraph 40, 41 or 42.

22. The method of embodiment 21 wherein the mammal is a rodent or a human.

23. The method of embodiment 21 or 22 wherein the numbers or activity of CD4$^+$CD25$^+$ regulatory T cells, CD4$^+$CD25$^+$CD103$^+$ regulatory T cells, CD4$^+$CD25$^{high}$CD103$^+$ regulatory T cells or CD4$^+$CD25$^{high}$ regulatory T cells are determined by a protocol comprising one, two or three of (a) the method of example 20 or a suitable variation thereof; (b) the method of example 21 or a suitable variation thereof; or (c) a method in a reference cited herein or a suitable variation thereof, wherein the or suitable variation permits assessment of numbers or activity of the CD4$^+$CD25$^+$ regulatory T cells, CD4$^+$CD25$^+$CD103$^+$ regulatory T cells, CD4$^+$CD25$^{high}$CD103$^+$ regulatory T cells or CD4$^+$CD25$^{high}$ regulatory T cells.

The method embodiment 21, 22 or 23 wherein the compound is for the treatment or prophylaxis of autoimmune disease or unwanted inflammation condition, which optionally is an arthritis condition such as an osteoarthritis (primary or secondary osteoarthritis), rheumatoid arthritis, an arthritis associated with spondylitis such as ankylosing spondylitis, multiple sclerosis, Alzheimer's disease, tenosynovitis, a lupus condition such as systemic lupus erythematosis or discoid lupus erythematosis, tendinitis, bursitis, a lung inflammation condition such as asthma, emphysema, chronic obstructive pulmonary disease, lung fibrosis, cystic fibrosis, acute or adult respiratory distress syndrome, chronic bronchitis, acute bronchitis, bronchiolitis, bronchiolitis fibrosa obliterans, bronchiolitis obliterans with organizing pneumonia. The compound can be a formula 1 compound as described herein.

25. A method to treat a metabolic disease in a human or a rodent having the metabolic disease, or subject to developing the metabolic disease comprising administering to the human or the rodent a treatment effective amount of a compound, optionally wherein the compound is a partial inhibitor of NF-κB in an in vitro assay or the compound is identified by the method of claim 1 in this application as originally filed or as described elsewhere herein. Such treatments include treatment with about 0.1 mg/day, about 1 mg/day or about 5 mg/day to about 40 mg/day or about 80 mg/day of a F1C described herein such as 17α-ethynylandrost-5-ene-3β,7β,17β-triol. Other F1C that can be used in this embodiment include 17α-ethynylandrost-5-ene-3α,7α,17α-triol, 17α-ethynylandrost-5-ene-7β,17β-diol-3-one, 17α-ethynylandrost-5-ene-3β,17β-diol-7-one, 17α-ethynylandrost-5-ene-3α,17β-diol-7-one, 17α-chloroethynylandrost-5-ene-3β,7β,17β-triol, 17α-chloroethynylandrost-5-ene-3α,7β,17β-triol, androst-5-ene-3β,4β,16α,17β-tetrol, 17α-ethynylandrost-5-ene-3β,4β,16α,17β-tetrol, androst-5-ene-3β,4β,7β,17β-tetrol, 17α-ethynylandrost-5-ene-3β,4β,7β,17β-tetrol, 3β,4β-diacetoxyandrost-5-ene-7β,17β-diol, 3β,4β-diacetoxy-17α-ethynylandrost-5-ene-7β,17β-diol, 3α,4β-diacetoxyandrost-5-ene-7β,17β-diol, 3α,4β-diacetoxy-17α-ethynylandrost-5-ene-7β,17β-diol, androst-5-ene-2β,3α,7β,17β-tetrol, 17α-ethynylandrost-5-ene-2β,3α,7β,17β-tetrol and androst-5-ene-2α,3β,7β,17β-tetrol, 17α-ethynylandrost-5-ene-2α,3β,7β,17β-tetrol and analogs of these compounds where a —OH moiety replaces a hydrogen atom at the 18- or 19-position. These compounds include 17α-ethynylandrost-5-ene-3β,7β,17β,18-tetrol, 17α-ethynylandrost-5-ene-3α,7β,17β,18-tetrol, androst-5-ene-3β,4β,7β,17β,18-pentol, 17α-ethynylandrost-5-ene-3β,4β,7β,17β,18-pentol, 17α-ethynylandrost-5-ene-3β,7β,17β,19-tetrol, 17α-ethynylandrost-5-ene-3α, 7β,17β,19-tetrol, androst-5-ene-3β,4β,7β,17β,19-pentol, 17α-ethynylandrost-5-ene-3β,4β,7β,17β,19-pentol and compound described elsewhere. Human subject to developing diabetes are ones that are prediabetic and often obese.

26. The method of embodiment 25 wherein the F1C has the structure

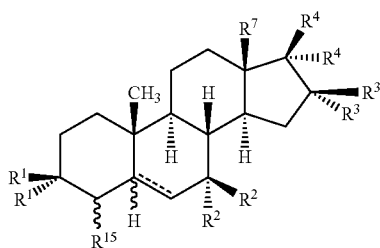

wherein one $R^1$ is —H or $C_{1-8}$ optionally substituted alkyl and the other $R^1$ is —OH, an ester or an ether; one $R^2$ is —H or $C_{1-8}$ optionally substituted alkyl and the other $R^2$ is —OH or an ester, or both $R^2$ together are =O; one $R^3$ is —H and the other $R^3$ is —H, —OH, an ester or an ether; one $R^4$ is optionally substituted $C_{2-4}$ alkynyl; one $R^4$, e.g., $R^4$ in the β-configuration, is —OH, an ester or an ether; $R^7$ is —CH$_3$, —CH$_2$OH or —C$_2$H$_5$; and $R^{15}$ is —H, a halogen, e.g., —F, —OH, =O, an ester or an ether.

27. The method of embodiment 25 or 26 wherein the metabolic disorder is type 2 diabetes, hyperglycemia, elevated nonesterified fatty acids, insulin resistance or another metabolic condition described herein or wherein the compound has the structure

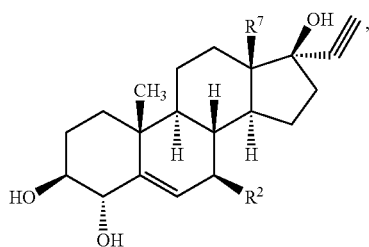

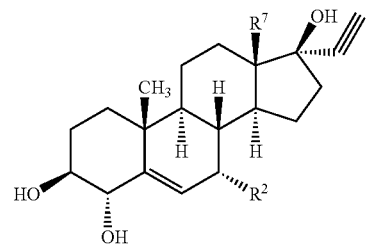

or

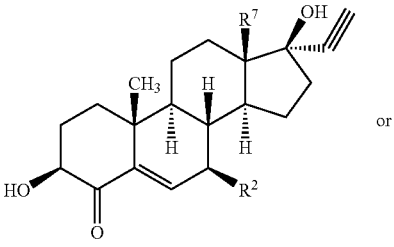

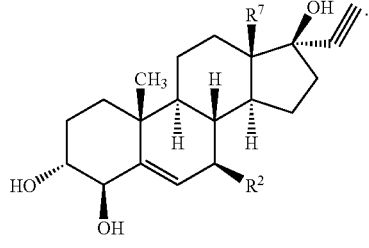

For some of these structures $R^2$ is —OH. For other structures, $R^2$ is —OC(O)CH$_3$. For other structures, $R^2$ is —OCH$_3$. For other structures, $R^2$ is an ether such as —OC$_2$H$_5$ or —OC$_3$H$_7$. For other structures, the hydroxyl at the 17 is esterified with an ester such as —OC(O)CH$_3$ (acetate), —OC(O)C$_2$H$_5$, —OC(O)—(CH$_2$)$_{10}$—CH$_3$, —OC(O)—(CH$_2$)$_{14}$—CH$_3$, —OC(O)—(CH$_2$)$_{16}$—CH$_3$.

28. A compound having the structure

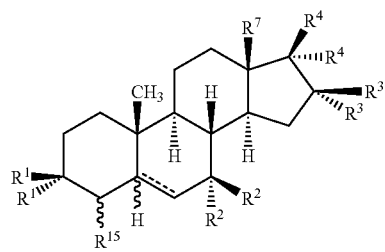

wherein the dotted line is an optional double bond and if no double bond is present at the 5-6 position, hydrogen is present at the 5-position in the α- or β-configuration; one $R^1$ is —H or $C_{1-8}$ optionally substituted alkyl and the other $R^1$ is —OH, an ester or an ether; one $R^2$ is —H or $C_{1-8}$ optionally substituted alkyl and the other $R^2$ is —OH, an ester, an ether, or both $R^2$ together are =O; one $R^3$ is —H and the other $R^3$ is —H, —OH, an ester or an ether; $R^4$ in the α-configuration is optionally substituted alkynyl or optionally substituted $C_{2-4}$ alkynyl; $R^4$ in the β-configuration is —OH, an ester or an ether; $R^7$ is $C_{1-4}$ optionally substituted alkyl such as —CH$_2$OH; and $R^{15}$ is —OH, an ester or an ether in the α- or β-configuration.

29. The compound of embodiment 28 wherein the compound has the structure

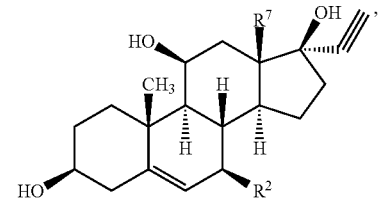

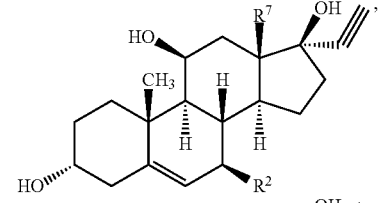

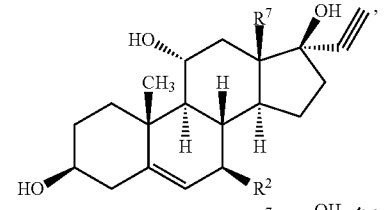

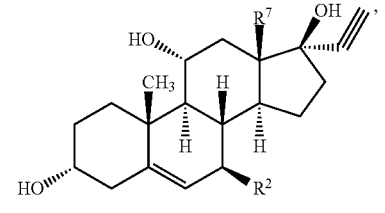

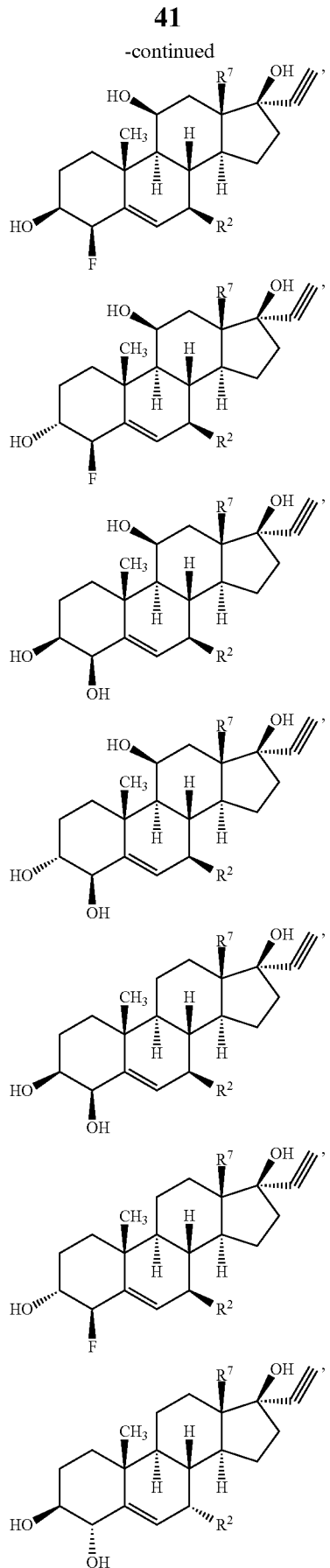

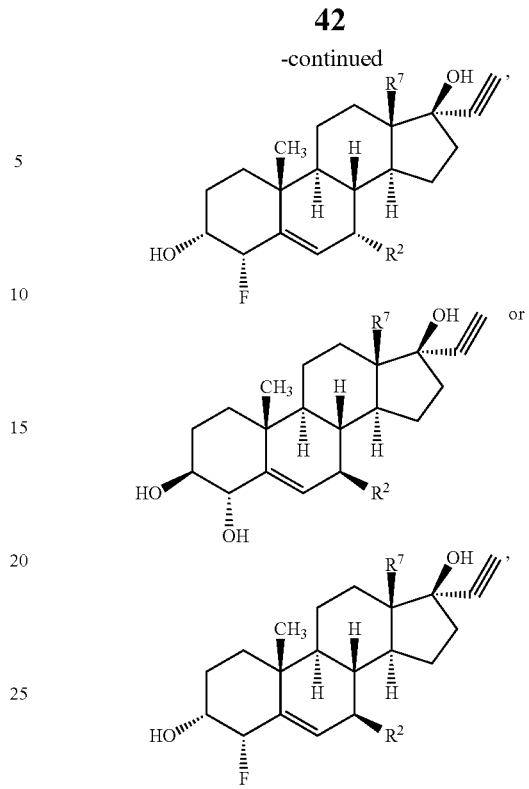

wherein R[7] is —CH$_3$ or —CH$_2$OH, and R[2] is —OH or an ester or ether such as —OCH$_3$. In some embodiments, (A) R[2] is —OC(O)CH$_3$ and R[7] is —CH$_2$OH (B), R[2] is —OC(O)CH$_3$ and R[7] is —CH$_3$, (C) R[2] is —OH and R[7] is —CH$_3$, (D) R[2] is —OH and R[7] is —C$_2$H$_5$. In other embodiments, hydroxyl at the 11-position, if present, is replaced with acetate. In other embodiments, the double bond at the 5-6 position is absent at hydrogen is present in the α-configuration, e.g., 17α-ethynylandrostane-3β,7β, 11β, 17β-tetrol or 17α-ethynylandrostane-3α,7β,11β,17β-tetrol. In other embodiments, the double bond at the 5-6 position is absent at hydrogen is present in the β-configuration, e.g., 17α-ethynyl-5β-androstane-3β,7β, 11β,17β-tetrol or 17α-ethynyl-5β-androstane-3α,7β,11β, 17β-tetrol.

Variations and modifications of these embodiments and other portions of this disclosure will be apparent to the skilled artisan after a reading thereof. Such variations and modifications are within the scope of this invention. The claims in this application or in applications that claim priority from this application will more particularly describe or define the invention. All citations or references cited herein are incorporated herein by reference in their entirety at this location or in additional paragraphs that follow this paragraph. Other descriptions are found in pending U.S. application Ser. No. 11/941,934, filed Nov. 17, 2007, U.S. provisional application Ser. No. 60/866,395, filed Nov. 17, 2006, U.S. provisional application Ser. No. 60/866,700, filed Nov. 21, 2006, U.S. provisional application Ser. No. 60/868,042, filed Nov. 30, 2006, U.S. provisional application Ser. No. 60/885,003, filed Jan. 15, 2007, U.S. provisional application Ser. No. 60/888,058, filed Feb. 2, 2007, all of which are incorporated herein by reference.

EXAMPLES

The following examples further illustrate the invention and they are not intended to limit it in any way.

Example 1

Treatment of lung inflammation. Three compounds, 3β,16α-dihydroxy-17-oxoandrostane, 3α,16α,17β-trihydroxyandrostane and 3α,16α,17α-trihydroxyandrostane were used to treat inflammation in mice essentially as described (D. Auci et al., *Ann. New York Acad. Sci.* 1051:730-742 2005). Five to 8 week old CD1 male mice (Charles River, Calco, Italy) were used for the study. The animals were housed in a controlled environment and provided with standard rodent chow and water. Animal care was in compliance with applicable regulations on protection of animals. Mice were allocated into one of the following groups: (1) mice treated with 2% carrageenan-λ in saline (carrageenan-λ treated control group), (2) mice treated with 0.1 mg, 0.01 mg or 0.001 mg 3β,16α-dihydroxy-17-oxoandrostane by subcutaneous (s.c.) injection 24 h and 1 h before carrageenan-λ administration, (3) mice treated with 0.1 mg, 0.01 mg or 0.001 mg of 3α,16α,17α-trihydroxyandrostane by s.c. injection 24 and 1 h before carrageenan; (4) mice treated with 0.1 mg, 0.01 mg or 0.001 mg 3α,16β,17β-trihydroxyandrostane by s.c. injection 24 h and 1 h before carrageenan-λ administration; (5) mice treated with vehicle (0.1% carboxymethylcellulose, 0.9% saline, 2% tween 80, 0.05% phenol) s.c. 24 h and 1 h before carrageenan-λ administration; (6) mice treated with rabbit anti-mouse polyclonal anti-TNF-α antibody (200 μg) given as an intraperitoneal bolus 24 h and 1 h before carrageenan-λ administration (positive control group); and (7) sham-operated mice that were not treated with carrageenan-λ. Each group consisted of 10 mice. All treatments were given in a final volume of 100 μL. Lung (pleural cavity) inflammation was induced as follows. The mice were anaesthetised with isoflurane and a skin incision was made at the level of the left sixth intercostal space. The underlying muscle was dissected and either 0.1 mL saline (control) or 0.1 mL saline containing 2% λ-carrageenan was injected into the pleural cavity. The carrageenan-λ is a potent inducer of inflammation, which is manifested in this protocol by accumulation of fluid and neutrophils in the pleural cavity. The incision was closed with a suture and the animals were allowed to recover.

At 4 h after the injection of carrageenan-λ, the animals were euthanized by exposure to $CO_2$. The chest was carefully opened and the pleural cavity rinsed with 1 mL of saline solution containing heparin (5 U/mL) and indomethacin (10 μg/mL). The exudate and washing solution were removed by aspiration and the total volume measured. Any exudate contaminated with blood was discarded. The amount of exudate was calculated by subtracting the injected 1 mL volume from the total pleural cavity volume that was recovered. The neutrophils in the exudate were suspended in phosphate-buffer saline and counted with an optical microscope in a Burker's chamber after Trypan Blue staining. The results were analysed by one-way ANOVA followed by a Bonferroni post-hoc test for multiple comparisons. A p-value less than 0.05 was considered significant. For statistical analysis each group was compared to the control group of mice that were challenged with carrageenan-λ and received no other treatment.

All of the mice that were challenged with carrageenan-λ and were left untreated developed an acute pleurisy, producing turbid exudate and increased pleural numbers of neutrophils. The increase in volume exudates and numbers of leukocytes in the pleura of the mice treated with the vehicle was similar to that observed in the control mice that were challenged with carrageenan-λ and received no treatment. Relative to these two groups of control mice, animals treated with 3β,16α-dihydroxy-17-oxoandrostane showed a significant reduction in the number of neutrophils in the pleura the volume of pleural exudates at the 0.1 mg 0.01 mg doses, while the lower 0.001 mg dose was inactive. The volume of pleural exudate at the 0.1 mg dose in the treated with 3β,16α-dihydroxy-17-oxoandrostane was significantly reduced, but not at the lower 0.01 mg and 0.001 mg doses. Animals treated with 3α,16α,17α-trihydroxyandrostane showed a significant reduction in the number of neutrophils in the pleura at the 0.1 mg and 0.01 mg doses. Treatment with 3α,16α,17α-trihydroxyandrostane also showed a significant reduction in the number of neutrophils in the pleura at the 0.1 mg and 0.01 mg doses. The potency of 3α,16α,17α-trihydroxyandrostane and 3α,16β,17α-trihydroxyandrostane were similar to that observed with the polyclonal anti-TNF-α antibody control, while 3β,16α-dihydroxy-17-oxoandrostane was less potent.

The table below describes the number of neutrophils from the treated animal groups relative to untreated control animals that were exposed to carrageenan-λ, but not treated with anything else (negative control group). The neutrophil number for the negative control group was set at 100% and other groups were compared to this. The group of animals that were treated with anti-TNF-α antibody (positive control group) had 29% of the number of neutrophils the negative control group had, which indicates that the antibody had an antiinflammatory effect against the carrageenan-λ exposure. The vehicle control group did not have a significantly reduced number of neutrophils (91%) compared to the negative control group, which shows no significant antiinflammatory effect due to the vehicle alone.

| 3β,16α-dihydroxy-17-oxoandrostane | | 3α,16α,17α-trihydroxyandrostane | | 3α,16β,17β-trihydroxyandrostane | |
|---|---|---|---|---|---|
| 0.001 mg | 97% | 0.001 mg | 103% | 0.001 mg | 95% |
| 0.01 mg | 73% | 0.01 mg | 45% | 0.01 mg | 50% |
| 0.1 mg | 73% | 0.1 mg | 30% | 0.1 mg | 42% |

Other compounds that had statistically significant anti-inflammation activity in this model were 17α-ethynylandrost-5-ene-3β,7β,17β-triol (1 mg and 0.1 mg administered by oral gavage) and 17β-aminoandrost-5-ene-3β-ol (40 mg/kg administered by oral gavage, about 0.5 mg/mouse). These compounds were active as compared to groups of mice that were used as vehicle controls.

Other formula 1 compounds described herein can be used in this manner to characterize their relative capacity to treat or ameliorate inflammation. These compounds include 3β,16β,17β-trihydroxyandrostane, 3β,16α,17α-trihydroxyandrostane, 3β,16β,17α-trihydroxyandrostane, 3β,16β-dihydroxyandrost-5-ene-17-oxime, 3β,16α-dihydroxyandrost-5-ene-17-oxime, 3α,16α-dihydroxyandrost-5-ene-17-oxime, 3β,16α-dihydroxyandrostane-17-oxime and analogs of these compounds that (1) contain a hydroxyl group at the 7-position in the α-configuration or the β-configuration and/or (2) a double bond at the 5-position or the 4-position, and/or (3) an ester, ether, amino acid, carbamate or oxime (=NOH) derivative, conjugate or analog of any of these.

Example 2

Analysis of the immune response. The compound 3α,16α,17α-trihydroxyandrostane was found to have biological properties that make the compound superior as an agent to treat an inflammation condition such as asthma. Specifically, the use of the compound was not accompanied by a rebound in IL-13, which is a known side effect of antiinflammatory glucocorticoid compounds such as dexamethasone. The IL-13 rebound after glucocorticoid makes an asthma patient more prone to have subsequent acute flare, so an antiinflammatory agent that does not do this would be advantageous. This lack of an IL-13 rebound was unexpected.

The capacity of 3α,16α,17α-trihydroxyandrostane to limit eosinophil burden and to reduce key inflammatory mediators (IL-5, IL-13, cysteinyl leukotrienes) was observed in the ovalbumin (OVA) sensitized mouse model of asthma. BALB/c mice were sensitized by intraperitoneal injection with OVA (in alum adjuvant) on days 1, and 12. Airways were challenged with OVA on days 28 and 30 by delivery of OVA to the lung, or with saline. On day 31, six mice were with saline and 6 mice challenged with OVA were sacrificed and lung tissue was analyzed. The remaining animals were divided into 6 groups (6 mice per group). Groups of the mice were treated once daily by subcutaneous injection as follows. Group 1 vehicle control (0.1% carboxymethyl cellulose, 0.9% saline, 2% tween 80, 0.05% phenol). Group 2 dexamethazone (5 mg/kg). Group 3 3α,16α,17α-trihydroxyandrostane (1 mg/mouse). Three animals in groups 1-3 were sacrificed on day 35 at 1 hr after final treatment and the remaining 3 animals in groups 1-3 were sacrificed on day 38.

As shown in the table below, the 3α,16α, 17α-trihydroxyandrostane did not generate an IL-13 increase that was observed with animals that had been treated with dexamethasone.

| Treatment | IL-13 (pg/mL) |
|---|---|
| saline control | 220 |
| ovalbumin | 230 |
| vehicle (day 35) | 220 |
| dexamethasone (day 35) | 340 |
| 3α,16α,17α-trihydroxyandrostane (day 35) | 195 |
| vehicle (day 38) | 190 |
| dexamethasone (day 38) | 390 |
| 3α,16α,17α-trihydroxyandrostane (day 38) | 210 |

In addition to a reduction in the day 38 IL-13 rebound after challenge, the animals treated with 3α,16α,17α-trihydroxyandrostane had a reduced level of IL-5 in lung tissue (90 pg/mL) compared to the dexamethasone treated group (145 pg/mL). The IL-5 level in the vehicle control group was 75 pg/mL at day 38. Other formula 1 compounds described herein were used in this manner to identify their capacity to treat or ameliorate inflammation without an IL-13 and/or IL-5 rebound effect, including 3β,16β,17β-trihydroxyandrostane, 3β,16α,17α-trihydroxyandrostane, 3β,16β,17β-trihydroxyandrostane, androst-5-ene-2α,3β,16α,17β-tetrol androst-5-ene-3β,7β,16α,17β-tetrol and 17α-ethynylandrost-5-ene-3β,7β,17β-triol. These results show that the F1Cs can be used to treat lung inflammation or asthma in vivo.

In another protocol, a population of mast cells was cultivated from murine bone marrow as follows. Briefly, bone marrows from Balb/C mice were flushed from the femur using PBS and a 27 g needle. The cells were cultured in a mixture of ⅔ RPMI-1640 with 19% FBS and cells that secreted IL-3. The bone marrow cells were allowed to differentiate for 18-25 days in the IL-3-containing mixture before being used for experiments. Bone marrow cells cultured in this manner have a phenotype similar to mucosal mast cells and are referred to as bone marrow-derived mast cells (BMMC).

The homogeneity of the in vitro propagated mast cells was checked by conventional flow cytometry techniques and staining for cell-type specific markers. Between days 14 and 21 of propagation, mature mast cells were harvested and prepared for the test cultures. The objective was to assess of the effect of compounds such as dehydroepiandrosterone on mast cell stimulus-coupled degranulation. Prepared mast cells were dispensed into test culture wells at a density of $1 \times 10^7$ cells/mL. In control cultures, mast cells were induced to degranulate after cross linking of IgE receptors with IgE antigen-antibody complexes. In parallel groups of cultures mast cells were preincubated dehydroepiandrosterone at various doses followed by activation using anti-IgE antibody. There was no detectable degranulation of mast cells as measured by release of β-glucuronidase from cytosolic storage granules of the cells in the absence of the stimulus. Introduction of anti-Ig-E receptor antibody to the cultures caused a significant release of β-glucuronidase. When mast cells were exposed to dehydroepiandrosterone alone, there was no measurable degranulation. However, mast cells pre-exposed to doses of 100 μM dehydroepiandrosterone for 5 to 10 minutes before activation with anti-IgE antigen-antibody complexes, exhibited approximately 70% inhibition of degranulation. Lower levels of dehydroepiandrosterone showed proportionately less capacity to inhibit degranulation. In similar protocols, F1Cs such as 17α-ethynylandrost-5-ene-3β,7β,17β-triol, androst-5-ene-3β,7β,16α,17β-tetrol or androst-5-ene-3α,7β,16α,17β-tetrol were 10-1000 fold more potent than dehydroepiandrosterone.

Example 3

Treatment of lethal inflammation/shock. Two compounds, 16α-bromoepiandrosterone (3β-hydroxy-16α-bromoandrostane-17-one) and 3β,16α-dihydroxy-17-oxoandrostane, were used in a lethal shock protocol. In one protocol, 3 mg of 16α-bromoepiandrosterone was administered to one group of animals by oral gavage, while another group received 3 mg of 16α-bromoepiandrosterone by subcutaneous injection. A group of control animals received a placebo control. In this protocol, the 16α-bromoepiandrosterone was administered to mice at 24 hours before and at 1 hour after administration of a lethal amount of bacterial lipopolysaccharide (LPS). By the end of the observation period, 72 hours after LPS administration, none of the vehicle treated placebo control animals had survived, while 65% of animals that received 16α-bromoepiandrosterone by oral administration survived. 50% of the animals that received 16α-bromoepiandrosterone by subcutaneous injection survived. Animals that survived for 72 hours all recovered from the LPS exposure.

In a second assay, 16α-bromoepiandrosterone or 3β,16α-dihydroxy-17-oxoandrostane was administered to mice by oral gavage at 24 hours before and 1 hour after administration of a lethal amount of LPS. A vehicle treated group of animals was used as the placebo control. At 72 hours, 25% of the placebo control mice survived, 50% of the mice treated with 3β,16α-dihydroxy-17-oxoandrostane survived and 80% of the mice treated with 16α-bromoepiandrosterone survived.

In another assay, the capacity of 16α-bromoepiandrosterone and 3β,16α-dihydroxy-17-oxoandrostane to protect against lung injury induced by exposure to a sublethal amount of LPS in mice was shown. In this assay, the compounds, sterile saline (negative control) or vehicle (vehicle control) were administered to groups of 5 mice by oral gavage at 24 hours before and 1 hour after administration of 100 μg of LPS to the trachea and lungs of animals under light anesthesia. At 48 hours the animals were sacrificed and samples were obtained from the lungs of the animals by bronchiolar alveolar lavage (BAL). The numbers of cells in the BAL fluid were counted, with high numbers of cells showing lung inflammation and damage. In this assay, cells that mediate inflammation and lung damage infiltrate into the lungs in response to the presence of the LPS. In the negative control and vehicle control groups, the BAL fluid contained about $6 \times 10^7$ cells/mL. The numbers of cells in the groups of animals that were treated with 16α-bromoepiandrosterone (p=0.02) or 3β,16α-dihydroxy-17-oxoandrostane (p=0.04) had significantly reduced cell counts in the BAL fluid (about $4.4 \times 10^7$ cells/mL). This result shows the compounds may have activity in clinical conditions such as asthma or COPD where lung injury or damage is associated with uncontrolled or excess inflammation. Other compounds, e.g., 17α-ethynylandrost-5-ene-3β,7β,17β-triol or 17β-aminoandrost-5-ene-3β-ol, can be characterized in a similar manner.

Example 4

Clearance of bacteria from lung tissue. The capacity of 16α-bromoepiandrosterone to clear a *Pseudomonas aeruginosa* infection from lung tissue was shown using a previously published protocol, A. van Heeckeren et al., *J. Clin. Invest.*, 100(11):2810-2815 1977; A. van Heeckeren et al., *Am. J. Respir. Crit. Care Med.*, 161:271-279 2000. The protocol was conducted in CFTR mice, which are used as an animal model for human cystic fibrosis, S. D. Freedman et al., *Proc. Natl. Acad. Sci. USA*, 96(24):13995-14000 1999; W. Zeng et al., *Am. J. Physiol. Cell. Physiol.* 273:C442-C455 1997. Establishment of chronic *P. aeruginosa* infection using agarose beads containing bacteria (50 μL containing about $6.1 \times 10^4$ CFU/animal) was published earlier, J. R. Starke et al., *Pediatr. Res.*, 22:698-702 1987. Two groups of mice (n=9 for each group) were treated with 40 mg/kg of 16α-bromoepiandrosterone or vehicle (control) and the bacterial burden in the lungs of the animals was determined at 10 days after introduction of the agarose beads into the lung. At day 10, the bacterial burden in the lungs of the vehicle control animals was about $6 \times 10^6$ CFU/animal, while the animals treated with 16α-bromoepiandrosterone had a reduced (p=<0.04) bacteria burden. This result shows that 16α-bromoepiandrosterone can be used to treat or reduce lung infection, which is a desirable attribute for agents that are used to treat conditions such as cystic fibrosis.

Example 5

Anti-inflammation activity in human cells in vitro. The capacity of 16α-bromoepiandrosterone and 3β,16α-dihydroxy-17-oxoandrostane to reduce inflammation in human cells in vitro was demonstrated using human whole blood that was exposed to LPS. Reduced production of γ-interferon by the cells was observed in the presence of 16α-bromoepiandrosterone (100 mg/mL) and 3β,16α-dihydroxy-17-oxoandrostane compared to cells exposed to LPS alone (positive control) or vehicle (dimethylsulfoxide) without compound (vehicle control). The amount of γ-interferon was measured in the growth medium when the cells had been incubated in the presence of LPS for 24 hours.

Example 6

Treatment of autoimmune neurodegeneration. Three compounds, 17β-aminoandrost-5-ene-3β-ol, 17β-dimethylaminoandrost-5-ene-3β-ol and 17β-methylaminoandrost-5-ene-3β-ol were characterized for their capacity to ameliorate experimental allergic encephalomyelitis (EAE) in mice. This demyelinating condition is extensively used as a model for multiple sclerosis in humans and for testing of new therapies for treating multiple sclerosis, e.g., B. F. Bebo Jr. et al., *J. Neurosci. Res.* 52:420-426 1998; R. R. Voskuhl et al., *Neuroscientist*, 7:258-270 2001; H. Offner et al., *J. Neuroimmunol.*, 130:128-139 2002. Activity in this model shows the capacity of test compounds to prevent or slow the rate of neuron death that is associated with progression of the EAE disease.

In this protocol, the compounds were administered to female SJL/J mice by oral gavage at the onset of disease symptoms. An antigen was used to initiate the EAE condition in the mice. The antigen that was used for the active immunization was mouse proteolipid protein (PLP) residues 139-151. Immunization with this peptide antigen initiates an autoimmune Th1 mediated demyelinating disease of the central nervous system. The antigen was prepared by solid phase synthesis and purified by high-performance liquid chromatography. The EAE condition was initiated in the female SJL/J mice by immunization with 150 μg of the PLP 139-151 peptide in complete Freund's adjuvant containing 200 μg of *Mycobacterium tuberculosis*. The immunization protocol was subcutaneous injection over four sites on the hind flank on day 0. After immunization. the mice were assessed daily for clinical signs of EAE using the following scale: 0=no clinical signs or symptoms; 1=limp tail; 2=mild hind limb weakness and limp tail; 3=moderate hind limb weakness and limp tail or mild ataxia; 4=severe hind limb weakness and mild forearm weakness with moderate ataxia; 5=paraplegia with no more than moderate forelimb weakness; 6=paraplegia with severe forelimb weakness or severe ataxia or moribund condition.

Mice in the vehicle control group began to show observable symptoms of EAE at about 10-11 days after immunization with the PLP antigen, which is typical for the EAE disease model. The animals were dosed daily with 17β-aminoandrost-5-ene-3β-ol, 17β-dimethylaminoandrost-5-ene-3β-ol or 17β-methylaminoandrost-5-ene-3β-ol by oral gavage beginning at day 1, which was 1 day after immunization. All three of the compounds were active at a dose of 5 mg/kg and they reduced the clinical severity of the symptoms that were observed through day 26, when the observation period ended. The therapeutic activity for the compounds was observed at blood levels of about 10 mg/mL in the mice. These results showed that the compounds were biologically active in treating this chronic autoimmune neurodegeneration disease.

Example 7

Inhibition of NF-κB in vitro. A number of compounds were used to inhibit activation of NF-κB by TNF-α or LPS in human cells in vitro. Activation of NF-κB increases expression of a number of genes that mediate inflammation. This protocol used human THP-1 cells, which are human mononuclear blood cells with a monocyte phenotype. The cell line, referred to as NF-κB-bla THP-1, contained a β-lactamase reporter gene under the control of the NF-kB response element (Invitrogen, CellSensor™, product No. K1176). In this cell line, the β-lactamase reporter gene is stably integrated in the THP-1 cells. This cell line was used to detect agonists or antagonists of the NF-κB signaling pathway. These NF-κB-bla THP-1 cells respond to the presence of tumor necrosis factor alpha (TNFα) or bacterial lipopolysaccharide (LPS) by increased expression of the β-lactamase reporter gene. The level of β-lactamase enzyme activity was measured by fluorescence resonance energy transfer ratiometric detection. TNFα and LPS are both potent inflammation-inducing agents that activate NF-κB in THP1 cells. In this assay, compounds that decrease NF-κB activity, and thus β-lactamase, in the presence of TNFα or LPS are exerting an anti-inflammation activity.

The NF-κB-bla THP-1 cells were maintained by passaging or feeding as needed. The cells, which grow in suspension, were maintained at a density between $2 \times 10^5$ cells per mL and $2 \times 10^6$ cells/mL. The cells were plated at 20,000 cells/well in a 384-well Black-wall, clear bottom assay plates (Costar#3712-TC low fluorescence background plates) approximately 24 hours before adding either TNFα at 10 mg/mL or LPS at 0.2 mg/mL to activate NF-κB. In positive control assays for activation of NF-κB, the $EC_{50}$ concentration for TNFα was 0.20 mg/mL after a 1 hour β-lactamase substrate incubation. The $EC_{50}$ dose for LPS was 0.15 mg/mL. The $EC_{50}$ concentration for TNF-α or LPS in this assay refers to 50% of the concentration of TNF-α or LPS that causes a maximum activation of NF-κB. The synthetic glucocorticoid dexamethasone (a potent anti-inflammatory drug) decreased the effect of TNFα by with an $EC_{50}$ of 0.47 nM (average of 5 assays) in this assay. Similar biological activity for dexamethasone has been reported in other in vitro cell assays, with complete inhibition of NF-kB activation observed at an $IC_{50}$ of about 1 nM (M. K. A. Bauer et al., Eur. J. Biochem. 243:726-731, 1977).

Using this assay, the $IC_{50}$ of compounds for inhibition of NF-κB activation in NF-κB-bla THP-1 cells after LPS stimulation is shown below. The $IC_{50}$ concentration for the compounds used in this assay refers to the concentration of compound that causes a 50% of the maximum inhibition of NF-κB activation that the compound can induce. The assays were usually conducted 2-4 times for each compound and the values shown below are averages for each compound. The data in Table 1 below shows that very low levels of many of these compounds can inhibit NF-κB in these human macrophage cells.

TABLE 1

| $IC_{50}$* | compound |
|---|---|
| 0.47 nM ± 0.11 | dexamethasone (positive anti-inflammation control) |
| >10 μM | estradiol (negative anti-inflammation control) |
| 8.2 fM ± 7.4 | 3β,7β,16α,17β-tetrahydroxyandrost-5-ene |
| 84.5 fM ± 65 | 3α,7β,16α,17β-tetrahydroxyandrost-5-ene |
| >10 μM | 3β,7α,16α,17β-tetrahydroxyandrost-5-ene |
| >10 μM | 16α-acetoxy-3β,7β,17β-trihydroxyandrost-5-ene |
| 0.4 fM | 3β,4β,16α,17β-tetrahydroxyandrost-5-ene |
| 0.01 fM | 4β-acetoxy-3β,16β,17β-trihydroxyandrost-5-ene |
| 2.0 fM | 3β-acetoxy-7β,11β,17β-trihydroxyandrost-5-ene |
| >10 μM | 3β,7β,11β,17β-tetrahydroxyandrost-5-ene |
| 10 fM | 3β,7β,17β-trihydroxy-11-oxoandrost-5-ene |
| 0.1 pM | 17α-methyl-3β,11α,17β-trihydroxyandrost-5-ene |
| >10 μM | 3β,11α-dihydroxy-17-oxoandrost-5-ene |
| 2.0 fM | 2α,3β,17β-trihydroxyandrostane |
| 14 pM ± 12 | 3β,17β-dihydroxyandrost-5-ene |
| 1.2 fM ± 0.28 | 3β,7β,17β-trihydroxyandrost-5-ene |
| >10 μM | 3β,7α,17β-trihydroxyandrost-5-ene |
| 19 fM ± 11 | 3β,7β,17β-trihydroxy-17α-ethynylandrost-5-ene |
| >10 μM | 3β,7β,17β-trihydroxy-17α-trifluoromethylandrost-5-ene |
| 6.8 fM ± 5.6 | 3β,7α,17β-trihydroxy-17α-ethynylandrost-5-ene |
| 12 fM ± 9.8 | 3β,7β,17β-trihydroxy-17α-vinylandrost-5-ene |
| 50.3 fM ± 13.9 | 3β,7β,17β-trihydroxy-17α-methylandrost-5-ene |
| 64 fM ± 36 | 3β,7α,17β-trihydroxy-17α-methylandrost-5-ene |
| 30 pM ± 29 | 16α-fluoroandrost-5-ene-17-one |
| 1.9 nM ± 0.8 | 16α-iodoepiandrosterone |
| 8.8 μM ± 1.3 | 16α-bromoepiandrosterone |
| 0.6 μM ± 0.2 | 16β-bromoepiandrosterone |
| >10 μM | 16α-hydroxyepiandrosterone |
| 7.2 fM ± 4.7 | 3β,17β-dihydroxy-17α-methylandrost-5-ene |
| 11.5 fM ± 3.5 | 3β,17β-dihydroxy-7-oxo-17α-ethynylandrost-5-ene |
| >10 μM | 3β,17β-dihydroxy-7-oxo-17α-methylandrost-5-ene |

*μM = $10^{-6}$ M; nM = $10^{-9}$ M; pM = $10^{-12}$ M; fM = $10^{-15}$ M

Other compounds that showed anti-inflammatory activity in this protocol were 3α-pentafluoroethylandrost-4-ene-3β,17β-diol ($IC_{50}$ 3.1 nM), 3α-pentafluoroethylandrost-5-ene-3β,17β-diol ($IC_{50}$ 17 nM; maximum NF-κB inhibition was 50%), 3α/β, 17α-ethynylandrostane-3α/β, 17β-diol ($IC_{50}$ 200 pM), 17α-trifluoromethylandrostane-3α,17β-diol ($IC_{50}$ 190 nM), 17β-glycylandrostane-3β-ol ($IC_{50}$ 0.42 pM), 3β-glycylandrostane-17β-ol ($IC_{50}$ 1 nM), androstane-3β,16β-diol-17-oxime ($IC_{50}$ 1.9 fM) 17α-ethynylandrost-4-ene-3-one-17β-ol ($IC_{50}$ 2.9 fM; maximum NF-κB inhibition was 80%), 16α-fluoroandrost-5-ene-17-one ($IC_{50}$ 30 pM), 16β-fluoroandrost-5-ene-7β-ol-17-one ($IC_{50}$ 1.5 nM), androstane-3α,16α,17β-triol ($IC_{50}$ 6.9 fM), androstane-3α,16β,17β-triol ($IC_{50}$ 19 fM), androst-5-ene-3β-ol-17β-succinyl ester ($IC_{50}$ 0.2 nM), 3β-acetoxy-7β,17β-dihydroxy-11-oxoandrost-5-ene ($IC_{50}$ 1 fM; maximum NF-κB inhibition was 65%). Maximum inhibition of NF-κB by these compounds was about 25% to 80%, which differed from 100% inhibition of NF-κB activation by the synthetic glucocorticoid dexamethasone in this protocol.

Two compounds increased NF-κB activity in this protocol, androst-5-ene-3β,7α,16α-triol-17-one ($IC_{50}$ 1.3 nM; 140% NF-κB activity compared to control cells) and 3β,17α-dimethylandrostane-3α,17β-diol ($IC_{50}$ 40 nM).

Compounds that did not exhibit anti-inflammation activity in this protocol were 3β,17α-methylandrostane-3β,17β-diol, 3β-acetoxyandrost-5-ene-3β,17β-diol, 17α-methylandrost-5-ene-3β,17β-diol-7-one, 16α-fluoroandrost-5-ene-7β-ol-17-one, 16α-fluoroandrost-5-ene-7α-ol-17-one, 17α-methylandrostane-3β,7α,17β-triol, androst-5-ene-3β, 11β,17β-triol, 16α-fluoroandrostane-17-one, androst-5-ene-3α,17β-diol, androstane-2β,3α,16α, 17β-tetrol and androstane-3α,16α,17α-triol, all of which had an $IC_{50}$>10 μM.

The capacity of the compounds to decrease the activity of NF-κB at low levels indicates that they can be used to treat inflammation, particularly in conditions where excess levels or nuclear transcription activity mediated by NF-kB plays a significant role in the pathology of the disease or condition.

In the assay described above, maximum inhibition of NF-κB by dexamethasone, 16α-bromoepiandrosterone and 16β-bromoepiandrosterone was 100% and there was no detectable NF-κB activation at concentrations of these compounds above the $IC_{50}$ for these compounds. By contrast, maximum inhibition of NF-κB by the other compounds e.g., 3β,7β,16α, 17β-tetrahydroxyandrost-5-ene, 3α, 7β,16α,17β-tetrahydroxyandrost-5-ene or 3β,7β,17β-trihydroxy-17α-methylandrost-5-ene was less than about 80%, with increasing amounts of the compounds above their $IC_{50}$ levels not providing significant additional inhibitory activity against NK-κB activation.

Several compounds in Table 1 had no detectable capacity to exert an anti-inflammation activity in the in vitro cell assay. Other compounds that were tested and had no activity in the assay ($IC_{50}$>10 μM) included 3β,17α-dihydroxyandrost-5-ene, dehydroepiandrosterone (3β-hydroxyandrost-5-ene-17-one), 3β-hydroxyandrostane-7,17-dione, 16α-bromo-3β,17β-dihydroxyandrost-5-ene and 16β-bromo-3β-hydroxyandrost-5-ene-17-one. Nonetheless, some of those compounds that were inactive in this in vitro cell assay, e.g., 16α-hydroxyepiandrosterone, were found nonetheless to be anti-inflammatory in animals in vivo. This result shows that the compounds may act through different mechanisms or that their activity requires more than cells from a single cell line.

Methods to modulate NF-κB that have been described and that can be incorporated into or used in the practice of the present invention include those described in the following publications. U.S. Pat. Nos. 5,989,835, 6,410,516, 6,545,027, 6,831,065 and 6,998,383. Other aspects of NF-κB activity have been described and can also be incorporated into the invention methods, e.g., A. S. Baldwin, *Annual Rev. Immunol.* 14:649-683 1996; M. Muller et al., *Mol. Cell. Biol.* 22((4) 1060-1072 2002; P. A. Baeuerle, *Cell* 195:729-731 1998.

Example 8

The capacity of selected compounds to treat LPS induced shock/inflammation in mice was examined by a protocol similar to the protocol described above. Five groups of three ICR mice weighing about 30 g were each treated by intraperitoneal injection with 120 μL vehicle (30% sulfobutylether-cyclodextrin in water), androst-5-ene-3α,7β,16α,17β-tetrol in vehicle, androst-5-ene-3β,4β,16α,17β-tetrol in vehicle or 4β-acetoxyandrost-5-ene-3β,16α,17β-triol in vehicle. All drug and vehicle formulations were solutions, not suspensions. The sulfobutylether-cyclodextrin was obtained commercially (Captisol™, www.cyclexinc.com). There were two vehicle control groups one group received vehicle alone and the other received vehicle plus LPS. The vehicle or drug was administered 24 hours before and at 1 hour after LPS (about an $LD_{50/24}$ dose, i.e., 50% lethal at 24 hours after LPS administration) was administered to the mice by intraperitoneal injection. Drug was administered at about 40 mg/kg (1.2 mg drug/animal for each administration of the drugs). Spleens were harvested from the animals at 1.5 hours after injection of LPS and spleen cells were lysed and assayed for activated NF-κB by isolating nuclei from spleen cells and measuring NF-κB from the lysed nuclei. The results indicated that all three compounds decreased the level of NF-κB activation compared to the LPS+vehicle control group by about 50%. The level of activated NF-κB in spleen cells from the animals that were treated with vehicle and no LPS, was essentially the same as the activated NF-κB in spleen cells from drug treated animals. These results indicated a potent anti-inflammation effect in the animals as shown by a decrease in activated NF-κB in drug treated animals compared to control animals.

Example 9

Kinetic analysis of NF-kB inhibition in vivo. The kinetics of NF-kB inhibition after injection of bacterial LPS in mice was examined to further probe the mechanism of action of compounds such as 17α-ethynylandrost-5-ene-3β,7β,17β-triol, which will only partially inhibit activation of NF-κB that is induced by LPS or TNFα in immune cells (macrophages or monocytes) in vitro as described in example 7. In this study, mice were treated with 17α-ethynylandrost-5-ene-3β,7β,17β-triol (about 40 mg/kg, about 1.2 mg/animal) by intraperitoneal injection of a solution (not a suspension) of the compound in the vehicle described in example 8. The drug was injected 24 hours before intraperitoneal injection of bacterial LPS (about an $LD_{50/24}$). The study used two groups of 12 animals, vehicle control or drug administered 24 hours before LPS challenge. Spleens were harvested from 3 animals from both groups just before LPS challenge and at 1.5, 2.0 and 2.5 hours after administration of LPS. Spleen cells were harvested and the level of activated NF-κB was measured by assay of NF-κB in nuclei essentially as described in example 8.

Maximum NF-κB activation after LPS administration occurred at 1.5 hours in the vehicle controls, which was 4-fold increased over the pre-LPS level of activated NF-κB. The results are shown below. The values for the vehicle control and drug treated animals are relative optical density units from ELISA measurement of NF-κB in nuclei from spleen cells.

| Time (hours) | vehicle control | drug treated |
|---|---|---|
| 0 | 18 | 22 |
| 1.5 | 72 | 2 |
| 2.0 | 10 | 7 |
| 2.5 | 10 | 9 |

The profound inhibition of NF-κB at the 1.5 hour time point and relatively normal levels of NF-κB activity at the other time points indicated that the compound exerted a transient but potent inhibition of LPS induced trauma at a critical period after LPS exposure. Similar assays in other studies showed that the level of activated NF-κB at 30 minutes and 60 minutes after injection of LPS in vehicle control mice was similar to the pre-LPS time point in this study. This result indicates that in this model, the effect of LPS on the activation of NF-κB in spleen cells is maximal at about 1.5 hours post LPS challenge. This time point reveals a convenient time or window at which the activity of drug candidates can be assessed in vivo, i.e., at about 75 minutes to about 105 minutes after LPS challenge. A component of the beneficial biological activity of such drug candidates can include moderation or reduction of inflammation that is at least transient, e.g., lasting for about 15 minutes or 30 minutes 45 minutes or more. The window can vary, depending on the route of administration of the biological insult, e.g., LPS or TNFα, administered by intraperitoneal injection versus LPS or TNFα administered by subcutaneous or intramuscular injection.

Analysis of LPS induced TNFα expression in mice showed that TNFα levels peaked at 1.5 hours after LPS challenge (500 μg of LPS administered by intraperitoneal injection) with highest levels of TNFα observed at 1-2 hours after LPS challenge. TNFα levels at 30 minutes after LPS and at 2.5 hours were lower.

Other compounds that can be analyzed for their capacity to act as biodynamic drugs include androst-5-ene-3β,7β,16α,17β-tetrol, androst-5-ene-3α,7β,16α,17β-tetrol, androst-5-ene-3β,7α,16α,17β-tetrol, androst-5-ene-3β,4β,16α,17β-tetrol, androst-5-ene-3β,4α,16α,17β-tetrol, androst-5-ene-3α,4β,16α,17β-tetrol, 17α-ethynylandrost-5-ene-3β,7α,17β-triol, 17α-ethynylandrost-5-ene-3β,7α,17β-triol, 17α-ethynylandrost-5-ene-3β,17β-triol-7-one and pharmaceutically acceptable analogs of any of these compounds, e.g., analogs that are hydroxyl ester or ether derivatives at 1, 2 or more hydroxyl groups. Suitable esters and ethers include acetate, n-propionate, i-propionate, succinate, —O—C(O)—$(CH_2)_n$—$CH_2R$, —O—C(O)—O—$(CH_2)_n$—$CH_2R$, —O—C(O)—NH—$(CH_2)_n$—$CH_2R$, amino acid such as glycine and alanine (—O—C(O)—$CHCH_3$—COOH), hydroxy esters and methyl, ethyl, n-propyl, i-propyl —O—$(CH_2)_n$—$CH_2R$, —O—$(CH_2)_n$—O—$CH_2R$ (e.g., —O—$CH_2CH_2$—O—$CH_3$) ethers, wherein n is 1, 2, 3, 4, 5 or 6 and R is —H, —F, —Cl, —Br, —I, —OH, —C(O)OH (or an acceptable salt, e.g., sodium or potassium salt), —C(O)$OCH_3$, —C(O)$OC_2H_5$.

Example 10

The capacity of formula 1 compounds to affect the course of arthritis in a passive collagen induced arthritis model of arthritis was examined essentially as previously described (E.

Simelyte et al., *Arthritis & Rheumatism,* 52(6):1876-1884, 2005; Z. Han et al. *Arthritis & Rheumatism* 46(3):818-823, 2002; H. Miyahara et al. *Clin. Immunol. Immunopathol.,* 69(1):69-76, 1993). In this protocol, passive collagen-induced arthritis was induced in DBA/1 mice by administering anti-type II collagen antibodies, which induced an immune response against joint tissue in the animals. Efficacy in this model of arthritis shows efficacy primarily against inflammation, which is assessed in isolation from cellular effects that operate in arthritis. The severity of arthritis was assessed using a semiquantitative clinical scoring system. Groups of 8 animals per group were treated with 17α-ethynylandrost-5-ene-3β,7β,17β-triol at 40 mg/kg/day for 14 days or vehicle for 14 days by oral gavage. The vehicle was 30% cyclodextrin-sulfobutylether in water and the drug solution was vehicle with drug at 20 mg/mL.

The animals were examined by measuring ankle thickness and arthritis score (4-point/paw) with a higher score indicating a more severe arthritis. The experiment was terminated after about 14 days, and histology and gene expression measurements were performed. For histology, the left hind paw was harvested, fixed in 10% formalin for 24 h, decalcified, and embedded in paraffin. Tissue sections were stained with hematoxylin and eosin for safranin O-fast green to determine proteoglycan content. A semi-quantitative scoring system was used to access synovial inflammation, extraarticular inflammation, erosion and proteogylcan loss.

Treatment with the compound began following administration of the antibodies. The protocol allowed observation of the effects of treatment on the progression of arthritis. The results showed that collagen induced arthritis in group 1 was reduced in group 1 animals compared to group 4 animals and at days 7-14. The maximum clinical score in vehicle treated animals was 10.2 at day 8 compared to a maximum clinical score of 5.1 in group 1 animals at day 7. At the end of the protocol at day 14, the vehicle treated group clinical score was 7.8 compared to the control group score, which was 4.1. Differences in clinical score at days 7-14 were apparent in the treated animals, which showed a reduced level of inflammation was present in the treated animals compared to the vehicle control animal group. The effect of treatment with 17α-ethynylandrost-5-ene-3β,7β,17β-triol was similar to treatment with dexamethasone, which also inhibits inflammation and reduces the severity of arthritis in this animal model. The capacity of 17α-ethynylandrost-5-ene-3β,7β,17β-triol to reduce the severity of arthritis contrasts with suppressors of cell mediated immunity such as methotrexate or anti-TNFα agents, which have little efficacy in this arthritis model.

Example 11

The capacity of formula 1 compounds to affect LPS-induced lung injury in the mouse was investigated. LPS-induced lung injury models previously have been used to evaluate treatments for acute lung injury (ALI), acute adult respiratory distress syndrome (ARDS) and endotoxin shock or sepsis (Metz et al., C., *Chest* 100(4): 1110-9,1991; Windsor, A. C. et al., *Ann. J. Med. Sci.* 306(2): 111-6, 1993; Brigham K. L. et al., *Am. Rev. Respir. Dis.* 133(5): 913-27, 1986).

The protocol conducted was essentially as described in Su, X. et al., *Intenstive Care Med.* 30:133-140, 2004. Female mice 6-8 week old C57/BL6 mice (average body weight of 25 g) obtained from Jackson Laboratory (Bar Harbor, Me.) were randomized into groups of seven animals and were maintained under standard housing and food. The groups were (1) mice treated with saline and LPS, (2) mice treated with vehicle and LPS (3) mice treated with 125 μg dexamethasone, (4) mice treated with 40 mg/Kg androst-5-ene-3β,7β,16α,17β-tetrol and LPS, (5) mice treated with 40 mg/Kg 5α-androstane-3β,16α-diol-17-one and LPS, (6) mice treated with 40 mg/Kg 5α-androstane-3β,17β-dihydroxy-16-oxime and (7) mice treated with 40 mg/Kg androst-5-ene-3α, 7β,16α, 17β-tetrol.

On day −1 mice were pre-treated with compound or vehicle. On day 0 mice were treated with a second dose of compound or vehicle. On day 0+60 minutes, mice were challenged with 100 μg of *E. Coli* LPS (Sigma) under direct visualization of the trachea under light anesthesia. On day 2 (i.e. 48 hour time point after LPS challenge) mice were sacrificed mice and BAL obtained (where cell counts and TNFα/IL6 levels were measured). The lungs were taken, minced and used for myeloperoxidase (MPO) studies. LPS-induced acute lung inflammation was preformed by instilling 50 mg LPS (*E. Coli* 0111:B4, Sigma-Aldrich) in 100 mL PBS into the tracheas of lightly anesthetized (isoflurane) under direct visualization. At 48 h time point, the mice were sacrificed. After this, a tracheotomy is established after exposing the trachea in the lower neck. A blunt ended 20 gauge needle is inserted into the exposed trachea, which is then tied off and used to obtain the bronchoalveolar lavage (BAL). To minimize airway bleeding and trauma, BAL is performed using 0.5 mL of sterile PBS X 3. A total of 1300 mL are typically recovered from this process. Cell differential leukocyte counts are determined in BAL fluid (BALF) using a hemacytometer. Differentials are performed on 80-100 cells. After obtaining the BAL, the chest cavity is opened and the heart/lungs are perfused with 3 mL of sterile saline through a R ventricular puncture. All of the lung tissue is then harvested and prepared for the MPO assay. For this assay, lungs are individually homogenized in potassium phosphate buffer (pH 6.0 containing 0.5% hexadecyltrimethylammonium bromide). Following centrifugation (14,000×g, 10 min 4° C.) 50 μL of supernatant was added to 950 μL potassium phosphate buffer containing 0.2 mg/mL o-dianisidine dihydrochloride (Sigma-Aldrich) and 0.00002% hydrogen peroxide. Changes in absorbance are measured at 460 ηm. Cytokine levels are determined in BALF cell-free supernatant (200×g, 10 min, 4° C.) by ELISAs for TNFα, IL-6 (R&D Systems) using commercially available ELISAs. Particularly striking are the results for andrsost-5-ene-3β,7β,16α,17β-tetrol for which it was found that animals treated orally with this compound had reduced levels of MPO, TNFα and IL-6 in BAL as compared to vehicle treated animals. The effect on MPO, which is a measure of neutrophil burden in the lung, and the pro-inflammatory cytokine TNFα was particularly profound. This suggests the ability of the compound to block the migration of pro-inflammatory cells into inflamed tissue as well as to reduce the pro-inflammatory cytokine signaling. In this model, acute inflammation is presumably driven by LPS stimulation of elements of innate immunity. Many of these same mediators are increased and thought to be involved in lung inflammation associated with several disorders, including cystic fibrosis, chronic obstructive pulmonary diseases, acute and chronic bronchitis, and even certain infectious diseases like tuberculosis. The observation that treatment with andrsost-5-ene-3β,7β,16α,17β-tetrol dramatically reduced MPO and pro-inflammatory cytokine levels in BALF at 48 h is in keeping with the anti-inflammatory activities reported herein for andrsost-5-ene-3β,7β,16α,17β-tetrol in disease specific models of chronic inflammation, including EAE.

Example 12

Human mixed lymphocyte reaction (MLR). The capacity of 3β,16α-dihydroxy-17-oxoandrostane, 3β,17β-dihydroxy- 16-oxoandrostane, 17α-ethynylandrost-5-ene-3β,7β,17β-triol, and 17β-aminoandrost-5-ene-3β-ol to affect antigen specific stimulation in which human T lymphocytes respond to a specific foreign antigen (major histocompatibility complex). The MLR is used as an in vitro model of delayed type hypersensitivity responses and shows the effect that a compound can have on human antigen-specific T cell responses in vivo. Inhibition of the MLR by a compound shows an immune suppression effect of the compound on lymphocytes. Compounds that do not inhibit the MLR are not immune suppressive for the antigen specific activation of responding lymphocytes.

Blood samples were obtained from 3 (2 males, 1 female) fasting, healthy human volunteers of 23-31 years old. The subjects did not use immunomodulatory, anti-allergic drugs or antibiotics in the three months before the study. The subjects were bled between 9 and 10 AM to limit possible fluctuations in the circulating levels of hormones or cytokines that could have influenced the in vitro responses of their lymphocytes. Peripheral blood mononuclear cells (PBMC) were isolated by centrifugation on Ficoll-Hypaque (density 1.077, Biochrom AG, Berlin, Germany) gradients and resuspended in culture medium (RPMI 1640 supplemented with 2 mM L-glutamine, penicillin (100 U/mL) and streptomycin (100 mg/mL) (Invitrogen s.rl., Milan, Italy). Autologous (responder) inactivated plasma was used at 10%. Five hundred thousand responder PBMC (PBMCr) and 500,000 allogeneic irradiated (30 Gy) stimulator PBMC (PBMCs) were mixed at a ratio of 1:1 in 200 µL medium and cultured for 6 days in flat bottom 96 well plates (Nunc, Roskilde, Denmark) at a concentration of 300 nM or 30 nM for each of the 4 compounds. The compounds were dissolved in ethanol and then diluted to the desired concentration with culture medium leading to a final solution containing 0.01% of ethanol. This vehicle was used as control. Controls also included PBMCr and PBMCs cultured separately. During the last 8 hours of the culture period the PBMC were pulsed with 1 µCi/well [$^3$H] thymidine (Amersham, Milan, Italy). The cells were then harvested and radioactivity incorporation measured with a beta cell counter. The mean cpm of quadruplicate wells was calculated. Proliferation of T cells was expressed as a stimulation index: SI=cpm (PMBCs×PBMCr)/cpm (PBMCr)+cpm (PBMCs). Statistical analysis was performed using the Student's t test. The cpm obtained from quadruplicate of each test compound were compared to proliferative responses obtained in control PBMCr and PBMCs cultured in the presence of the vehicle. Differences were considered significant at p<0.05.

The results showed no inhibition of the MLR by any of the 4 compounds except 17β-aminoandrost-5-ene-3β-ol at 300 nM. This indicated that 3β,16α-dihydroxy-17-oxoandrostane, 3β,17β-dihydroxy-16-oxoandrostane and 17α-ethynylandrost-5-ene-3β,7β,17β-triol were not appreciably immune suppressive in this assay at either 300 nM or 30 nM (p>0.05), while 17β-aminoandrost-5-ene-3β-ol at 300 nM was moderately immune suppressive (p<0.05) compared to the control reactions. These results show that 3β,16α-dihydroxy-17-oxoandrostane, 3β,17β-dihydroxy-16-oxoandrostane and 17α-ethynylandrost-5-ene-3β,7β,17β-triol would not be immune suppressive for lymphocytes in humans in vivo. These results are consistent with the capacity of the compounds to be anti-inflammatory agents (see, e.g., example 7) without being immune suppressive.

Example 13

Analysis of immune suppression. Glucocorticoid steroids such as dexamethasone or hydrocortisone are typically immune suppressive and have significant toxicities associated with their use. Immune suppression was examined in a reporter antigen popliteal lymph node assay in mice essentially as previously described (C. Goebel et al., *Inflamm. Res.*, 45(Suppl. 2):S85-S90, 1996; R. Pieters et al., *Environmental Health Perspectives* 107(Suppl. 5):673-677, 1999). This protocol was used to analyze the activity of 17α-ethynylandrost-5-ene-3β,7β,17β-triol in the popliteal lymph node (PLN) assay to show that the compound does not have appreciable immune suppression activity in vivo. In this protocol, the vehicle was 0.1% carboxymethylcellulose, 0.9% saline, 2% tween 80 and 0.05% phenol, which contained 17α-ethynylandrost-5-ene-3β,7β,17β-triol in suspension in drug treated animals. Assessment of activity included (1) measuring suppression of numbers of total lymphocytes, antigen specific IgM, IgG1 and IgG2a antibody secreting cells (ASC) (ELISPOT assay) in popliteal lymph node cells; (2) analysis of cell surface marker (CD4, CD8, CD19, F480, CD80, CD86) expression by flow cytometry of living cells in suspension; and (3) IL-4, TNFα and IFNγ production by lymphocytes in vitro (ELISA).

Groups (n=5 per group) of specific pathogen free BALB/C mice were used. The Positive control group was treated with vehicle (oral gavage) and 5 µg/day dexamethasone by subcutaneous injection to induce immune suppression. Vehicle control animals (negative control) were treated with vehicle alone (oral gavage). One group of animals was treated with 17α-ethynylandrost-5-ene-3β,7β,17β-triol at 0.1 mg/day by oral gavage. Another group was treated with 1 mg/day of 17α-ethynylandrost-5-ene-3β,7β,17β-triol was administered to the animals oral gavage. The results were analyzed by two-tailed Student's t-test with equal variance. The animals were injected in the right hind footpad with 50 µL of freshly prepared sensitizing dose of TNP-OVA. Dexamethasone (decadron phosphate injection; dexamethasone sodium phosphate) was administered by subcutaneous injection into the nape of the neck daily, immediately following sensitization with TNP-OVA. 17α-Ethynylandrost-5-ene-3β,7β,17β-triol was given immediately afterwards by gavage. Five days after injection of TNP-OVA, blood was drawn by orbital puncture, and the mice were euthanized by cervical dislocation and popliteal lymph nodes were removed and separated from adherent fatty tissue. Single cell suspensions were prepared, resuspended in 1 mL PBS-BSA (1%) and counted. Cell numbers, IL-4, IL-5 and IFNγ were measured.

The average number of lymphocytes in PLNs from the vehicle control group was $7.8 \times 10^6$ per lymph node compared to $2.9 \times 10^6$ per lymph node in the dexamethasone treated animal group. This reduced lymphocyte count clearly showed the marked immune suppression that is typically seen with the use of dexamethasone or other glucocorticoid compounds. By contrast, the group treated with 1 mg/day of 17α-ethynylandrost-5-ene-3β,7β,17β-triol had $8.2 \times 10^6$ lymphocytes per lymph node and the group treated with 0.1 mg/day of 17α-ethynylandrost-5-ene-3β,7β,17β-triol had $11.1 \times 10^6$ lymphocytes per lymph node. The results showed that 17α-ethynylandrost-5-ene-3β,7β,17β-triol was not immune suppressive, but was immune enhancing. 17α-Ethynylandrost-5-ene-3β,7β,17β-triol treatment at 1.0 mg/day and at 0.1 mg/day increased IFNγ, IL-4 and IL-5 levels compared to the vehicle control group, also indicating immune enhancement. The effect of 17α-ethynylandrost-5-ene-3β,7β,17β-triol at 0.1 mg/day on IFNγ, IL-4 and IL-5 levels was greater than in the group that was treated with 1.0 mg/day. By contrast, IFNγ, IL-4 and IL-5 levels were reduced in the dexamethasone treated group compared to the vehicle control group or to either drug treated group.

Example 14

Analysis of immune suppression. Several compounds were characterized for their capacity to affect immune responses. This protocol examined the immune effects of compounds in a standard immune assay. The ovalbumin (OVA) specific immune response assay is a well-established system to measure anamnestic (both cell-mediated and antibody-mediated) immune responses. BALB/c mice were immunized by intraperitoneal injection (total volume 200 µL) on days 0 and 7 with 100 µg OVA precipitated with alum (25 mg/mL) in saline. Mice (n=5 per group) were treated daily (oral gavage 40 mg/kg, about 1 mg/animal) for 20 days with compound. On day 20, blood was drawn and tested in ELISA for antibody titers to OVA. The compounds that were tested were 3β,16α-dihydroxy-17-oxoandrostane, 16α-bromoepiandrosterone, 17α-ethynylandrost-5-ene-3β,7β,17β-triol, 3β,16α-dihydroxyandrostane-17-oxime, 17β-aminoandrost-5-ene-3β-ol and 3α,16α,17β-trihydroxyandrostane. None of these compounds were profoundly immune suppressive, with OVA antibody titers similar to those in the vehicle control group.

Example 15

Glucose lowering and amelioration of insulin resistance. Glucose lowering effects and amelioration of insulin resistance was assessed in the diabetic db/db mouse model of human diabetes and insulin resistance. In these studies, db/db C57BL/Ks mice of approximately 8 to 10 weeks of age were divided into groups of 10 each and then treated with a vehicle control (no drug) or 17α-ethynylandrost-5-ene-3β,7β,17β-triol by oral gavage. The compound was administered twice a day at 20 mg/kg/day (10 mg/kg dose administered twice per day), 40 mg/kg/day (20 mg/kg dose administered twice per day) or 80 mg/kg/day (40 mg/kg dose administered twice per day) for up to 28 days. Blood glucose levels were monitored twice a week during the dosing period, using a minute amount of blood (nick tail bleeds) to measure the concentration of glucose by glucometer strips. At specific times during the dosing period (day 14 and day 28), an oral glucose tolerance test (OGTT) was also performed by administering a standard oral dose of 1 g/kg glucose (approximately 40 mg in a 40 mg mouse) and then the fluctuation of blood glucose levels was monitored quickly thereafter after at 15, 30, 60 and 120 minutes after the glucose dose. In the drug treated group, an approximately 40% decrease in hyperglycemic blood glucose levels was observed in the db/db mice. Blood glucose approached 380 mg/dL in the vehicle control group and was <230 mg/dL after at least 10 days of dosing in the drug treated group. Treatment with drug at 80 mg/kg b.i.d. for 28 days markedly reduced the peak glycemic excursion from approximately 400 mg/dL 30-min post-oral glucose dosing seen in vehicle-treated animals down to <200 mg/dL in the drug-treated group.

Example 16

Diet induced obesity (DIO) mouse hyperglycemia treatment. The effect of a drug to enhance peripheral sensitivity to insulin can be studied in a mouse model in which a state of insulin resistance is attained by feeding the animals a fat-enriched diet (60% of total caloric intake) for at least 6 weeks. This model has been described, e.g., J. N. Thupari et al., *Proc. Natl. Acad. Sci. USA*, 99(14):9498-9502, 2002, H. Xu et al., *J. Clin. Invest.*, 112:1821-1830, 2003, H. Takahashi et al., *J. Biol. Chem.*, 278(47):46654-46660, 2003. Under these diet conditions, the mice exhibit increased body weight (+35 g) and a state of glucose intolerance, which is manifested as a significant delay in the clearance time of orally-administered glucose during a standard OGTT (oral glucose tolerance test).

For these studies, animals of approximately 4 weeks of age were divided into groups of 10 animals each and then treated with a vehicle control (no drug) or 17α-ethynylandrost-5-ene-3β,7β,17β-triol by oral gavage. The 17α-ethynylandrost-5-ene-3β,7β,17β-triol was administered at 20 mg/kg, 40 mg/kg or 80 mg/kg twice a day for up to 28 days. At day 14 and day 28 during the dosing period an OGTT was performed. In this DIO-model of insulin resistance, 17α-ethynylandrost-5-ene-3β,7β,17β-triol notably reduced glucose intolerance compared to vehicle control animals as indicated by significant improvement in the OGTT glycemic excursion. These findings showed that treatment with 17α-ethynylandrost-5-ene-3β,7β,17β-triol enhanced peripheral insulin sensitivity or uptake, which improved glucose intolerance in these animals.

Example 17

A treatment protocol similar to that described in example 15 was performed with db/db mice that were younger than the animals described in example 15. The animals (n=8 to 10 per group) were treated with 17α-ethynylandrost-5-ene-3β,7β,17β-triol or vehicle by oral gavage twice per day at 40 mg/kg/day (20 mg/kg dose given twice per day) and 80 mg/kg/day (40 mg/kg dose given twice per day). At the start of dosing, the animals were 6 weeks of age, before the onset of elevated glucose levels or hyperglycemia. Dosing with vehicle or drug was maintained for 32 days to determine the effect of the treatments on the onset and rate of progression of hyperglycemia in the animals. In the control group, the onset of hyperglycemia was observed after 25 days of dosing and it continued to worsen, i.e., blood glucose levels rose from normal to frank hyperglycemia, through the end of the 32 day dosing period. By contrast, levels of glucose in both drug treatment groups did not rise above normal levels by the end of the 32 day dosing period, showing that drug treatment delayed the onset of hyperglycemia through the course of the protocol.

Administration of 17α-ethynylandrost-5-ene-3β,7β,17β-triol to 8 week old male diabetic db/db mice markedly suppressed basal blood glucose hyperglycemic levels, an effect that became apparent after 10 days of dosing and was sustained for 18 additional days of continuous, twice-a-day treatment in the 40 mg/kg dose group. In younger, 6 week old male db/db mice, treatment with the 17α-ethynylandrost-5-ene-3β,7β,17β-triol at 40 mg/kg completely blocked progression of the animals into the hyperglycemic state that was observed in the vehicle-treated group after 25 days of dosing. The treated animals maintained blood glucose levels that were comparable to those from lean db/+ littermates. Furthermore, results from OGTTs performed in treated animals model showed significant amelioration of glucose intolerance compared to vehicle control animals.

Example 18

Glucose lowering in 8 week old db/db diabetic mice. The hyperinsulinemic-euglycemic clamp protocol was conducted to measure insulin sensitivity in vivo. In this procedure, insulin was administered to raise the insulin concentration while glucose was infused to maintain euglycemia or a fixed, normal blood glucose level (about 180 mg/dL). The glucose infusion rate (GIR) needed to maintain euglycemia showed insulin action in these animals. The objective of this protocol was to investigate characterize the capacity of 17α-ethynylandrost-5-ene-3β,7β,17β-triol and androst-5-ene-3β,7β,16α,17β-tetrol to ameliorate systemic insulin resistance and improve whole body glucose disposal in the hyperinsulinemic-euglycemic clamp model. The degree of skeletal muscle and hepatic insulin sensitivity and tissue specific glucose uptake were also assessed. The animals were dosed daily by oral gavage for 14 days. On Day 10 of treatment catheters were implanted in the carotid artery and jugular vein. On the day of the clamp (day 14) the compound was administered at 7:30 am.

Body weight and glucose concentration were assessed on day 0, 7 and day 14 of treatment. On day 14 a euglycemic hyperinsulinemic clamp was performed. Food was removed at 7:30 am at 10:30 a primed continuous infusion of [3-$^3$H]-glucose (0.05 μCi/min). A baseline blood sample was taken at 12:50 (−10 min) and at 1:00 (0 min) a euglycemic hyperinsulinemic clamp was initiated by administering 10 mU/kg/min of insulin. Glucose was infused at a variable rate to clamp the glucose concentration at ~180 mg/dl. A bolus of [$^{14}$C]-2deoxyglucose was given at the end of the study to assess tissue specific glucose uptake. Plasma $^{14}$C2-deoxyglucose was assessed at 122, 125, 130, 135, 145 min. The animals were then anesthetized with an intravenous infusion of sodium pentobarbital and selected tissues were removed, immediately frozen in liquid nitrogen and stored at −70° C. until analysis.

Analysis was conducted as follows. Plasma samples were deproteinized with Ba(OH)$_2$ (0.3 N) and ZnSO$_4$ (0.3 N), dried and radioactivity was assessed on scintillation counter (Packard TRICARB 2900 TR, Meriden, Conn.). Frozen tissue samples were homogenized in 0.5% perchloric acid, centrifuged and neutralized. One supernatant was directly counted to determine radioactivity from both [$_{14}$C] DG and [$^{14}$C] DGP. A second aliquot was treated with Ba(OH)$_2$ and ZnSO$_4$ to remove $^{14}$C DGP and any tracer incorporated into glycogen and then counted to determine radioactivity from free [$^{14}$C] DG(2). [$^{14}$C]DGP was calculated as the difference between the two aliquots. The accumulation of [$^{14}$C]DGP was normalized to tissue weight and tracer bolus. Rg, an index of tissue specific glucose uptake was calculated as previously described (E. W. Kraegen et al., *Am. J. Physiol.*, 248:E353-E362, 1985). Whole body glucose turnover was calculated as the ratio of the $^3$H glucose infusion rate (dpm/kg/min) and arterial plasma glucose specific activity (dpm/mg). Endogenous glucose production was calculated as the difference between the whole body glucose turnover and the exogenous glucose infusion rate (R. N. Bergman et al., *Endocr. Rev.*, 6:45-86, 1985). Treatment groups are summarized in the table shown below.

| Group | Treatment | Dosing volume and dosing solution concentration | N |
|---|---|---|---|
| A - vehicle control* | vehicle 8 mL/kg, po, bid for 13 days, qd on day 14 | 8 mL/kg | 10 |
| B - compound 1** | 40 mg/kg, po, bid for 13 days, qd on day 14 | 4 mL/kg of 10 mg/mL stock in vehicle | 10 |
| C - compound 1** | 80 mg/kg, po, bid for 13 days, qd on day 14 | 8 ml/kg of 10 mg/ml stock in vehicle | 10 |
| D - compound 2** | 40 mg/kg, po, bid for 13 days, qd on day 14 | 4 mL/kg of 10 mg/mL in vehicle | 10 |
| E - positive*** control | 25 mg/kg, po, bid for 13 days, qd on day 14 | 5 mL/kg of 5 mg/mL in water + 1% CMC | 10 |

*vehicle: 30% sulfobutylether in water (20 mg/mL of drug in solution for groups B-D)
**compound 1: 17α-ethynylandrost-5-ene-3β,7β,17β-triol
compound 2: androst-5-ene-3β,7β,16α,17β-tetrol
***rosiglitazone maleate (31493r, AApin Chemicals Limited (UK), CMC—Carboxymethyl cellulose (medium grade, C4888, Sigma)

The insulin dose was 10 mU/kg/min. In a normal animal, this dose of insulin would require infusion of ~90 mg/kg/min of glucose to keep the glucose level clamped at ~150 mg/dl. The average glucose requirement in all treatment groups was ~50% of normal. The results showed that both 17α-ethynylandrost-5-ene-3β,7β,17β-triol and androst-5-ene-3β,7β,16α,17β-tetrol increased the glucose infusion rate compared to the vehicle control, which means insulin action was improved in the groups B, C, D and E.

Using the 3-$^3$H glucose tracer, the rate of liver glucose production was calculated during the basal period and the ability of insulin to suppress liver glucose production during the clamp. In severe insulin resistant animals endogenous glucose production would decrease by about 50% with the insulin dose that was used. In groups C, D and E, insulin completely suppressed endogenous glucose production ($p<0.05$), which showed an improvement in hepatic insulin action.

To assess peripheral insulin action, tissue specific glucose uptake during the euglycemic hyperinsulinemic clamp was assessed using $^{14}$C-2-deoxyglucose. A bolus of $^{14}$C-2-deoxyglucose was given at 120 min. Tissues were collected 25 minutes later. Tissues were analyzed for total accumulation of $^{14}$C-2-deoxyglucose phosphate. In this protocol, brain glucose uptake is unaffected by most treatment regimens and it thus serves as an internal control. The results showed that brain glucose uptake was comparable between all of the groups. In the heart and diaphragm, glucose uptake was higher in the treated groups compared to the vehicle control group. Both androst-5-ene-3β,7β,16α,17β-tetrol and rosiglitazone were more effective ($p<0.05$) in augmenting muscle glucose uptake in the gastrocnemius muscle. In white vastus muscle, which is a non oxidative muscle group, differences were not detected except between androst-5-ene-3β,7β,16α,17β-tetrol and rosiglitazone.

Example 19

Rats were fed ad libum with a standard laboratory chow that contained 0.45% wt/wt of androst-5-ene-3β,7β,17β-triol for 6 days, followed by analysis of liver tissue on day 6 for levels of phosphoenolpyruvate carboxykinase ("PEPCK") and 11β-hydroxysteroid dehydrogenase ("11β-HSD") in the liver. Control animals were fed normal chow and livers were examined on day 6 for PEPCK and 11β-HSD levels by measurement of messenger RNAs (mRNAs) by RT-PCR. Both control and treated animals had free access to water. Administration of the compound in chow for 6 days was found to decrease levels of 11β-HSD type 1 ("11β-HSD1") and PEPCK in liver tissue as shown below. Levels of PPARα mRNA in these animals were not affected by feeding with androst-5-ene-3β,7β, 17β-triol.

|  | 11β-HSD1 mRNA | PEPCK mRNA | PPARα mRNA |
|---|---|---|---|
| control (no compound) | 100% | 100% | 100% |
| androst-5-ene-3β,7β,17β-triol | 45% | 30% | 105% |

In another study, administration of the compound 17α-ethynylandrost-5-ene-3β,7β,17β-triol to mice was found to decrease expression of 11β-HSD1 in osteoblasts by about 50%, which is consistent with the observation that the compound possesses bone-sparing effects in mice treated with dexamethasone, a glucocorticoid that induces bone loss in vivo.

In another study, total RNA from perigonadal fat tissue from lean db/+ or diabetic db/db mice treated with 20 mg/kg of 17α-ethynylandrost-5-ene-3β,7β,17β-triol was isolated and processed for quantitative RT/PCR using primers specific for monocyte chemoattractant protein-1 (MCP-1) using an iCycler iQ multicolor real time-detection system (Bio-Rad). RNA expression levels were normalized with respect to the vehicle control. The compound was found to decrease levels of monocyte chemoattractant protein-1 (MCP-1) by about 50%. For this study, vehicle was also administered to a control group of age matched lean heterozygous db/+ mice (n=7).

Other compounds such as 17α-ethynylandrost-5-ene-3β, 7β,17β-triol, androst-5-ene-3β,7β,16α,17β-tetrol, androst-5-ene-3β,7α,16α,17β-tetrol, androst-5-ene-3α,7β,16α,17β-tetrol, androst-5-ene-3β,4β,16α,17β-tetrol, androst-5-ene-3α, 4β,16α,17β-tetrol or monoesters or diesters of these compounds, e.g., compounds containing one or two acetate or propionate esters at the 3- or 17-positions, are examined in a similar manner for their capacity to decrease the level or activity of PEPCK or a 11β-HSD, such as 11β-HSD type 1 or 11β-HSD type 2, in hepatocytes or liver-derived cells or in other tissues or cells such as kidney, muscle, bone tissue or cells, adipose tissue or cells or CNS tissue or cells, e.g., neurons or glia.

Example 20

Inhibition of the generation of CD4$^+$CD25$^+$ T regulatory cells or their activity in vivo. Purified CD4$^+$CD25$^-$ T cells (5×10$^6$ cells) from congenic B6.5JL mice (CD45.1) per group were adoptively transferred into each of five B6 mice (CD45.2). The purified CD4$^+$CD25$^-$ T cells were obtained by fluorescence activated cell sorting (FACS) of the donor cells at least twice. Vehicle (0.1% carboxymethylcellulose, 0.9% saline, 2% tween 80, 0.05% phenol) or 16α-bromoepiandrosterone in vehicle (1 mg/animal/day in 100 µL vehicle) was injected subcutaneously before transfer of the cells from the CD45.1 donor animals and the injections were continued daily for 14 days. Thymus, lymph nodes and spleens were collected from the animals at day 15. Samples of thymus, lymph node and spleen were obtained from individuals, and the cells were labeled with fluorescent antibody that bound to CD4, CD25, CD103 or Foxp3. The cells were then analyzed by flow cytometry to enumerate the numbers of the various cell types. The remainder of cells from lymph nodes and spleen of each treatment group were pooled, pre-enriched for CD4$^+$CD25$^+$ cells and then analyzed for CD4$^+$CD25$^+$ that arose from the host (endogenous CD45.2 cells) and from donor cells (CD45.1 cells that converted from the CD4$^+$CD25$^-$ donor phenotype to the CD4$^+$CD25$^+$ phenotype after residing in vivo for 15 days). The cells were analyzed by cell sorter. To test for regulatory function, varying numbers of purified converted CD45.1 or endogenous CD45.2 CD4$^+$CD25$^+$ cells were co-cultured with 2000 CD4$^+$CD25$^-$ responder cells, 1×10$^5$ irradiated spleen cells as antigen presenting cells, and 0.5 mg/ml of anti-CD3 antibody. Fresh CD4$^+$CD25$^+$ cells were used as controls. Proliferation was determined by measurement of $^3$H-thymidine uptake 4 days after initiation of culture.

The results showed that the number of donor CD45.1 CD4$^+$CD25$^+$ Treg cells in the spleens from drug treated animals was lower than the number of CD45.1 CD4$^+$CD25$^+$ Treg cells in the spleens from vehicle control animals. The average vehicle control CD45.1 CD4$^+$CD25$^+$ cell number was 1.97× 10$^5$ cells compared to an average of 0.62×10$^5$ CD45.1 CD4$^+$CD25$^+$ cells from the drug treated animals.

The number of endogenous CD45.2 CD4$^+$CD25$^+$ Treg cells in the spleens from drug treated animals was also lower than the number of CD45.1 CD4$^+$CD25$^+$ Treg cells in the spleens from vehicle control animals. The average vehicle control CD45.2 CD4$^+$CD25$^+$ cell number was 9.54×10$^6$ cells compared to an average drug treated 5.49×10$^6$ CD45.2 CD4$^+$CD25$^+$ cells.

The average endogenous CD45.2 CD4$^+$CD25$^+$ cells in the thymus of vehicle control animals was 3.10×10$^5$ compared to 1.59×10$^5$ in the drug treated animals.

The percent of donor CD45.1 CD4$^+$CD25$^+$CD103$^+$ cells compared to total donor CD4$^+$CD25$^+$ cells in the spleens from drug treated animals was lower than the number of CD45.1 CD4$^+$CD25$^+$CD103$^+$ Treg cells compared to total donor CD4$^+$CD25$^+$ cells in the spleens from vehicle control animals. The proportion of endogenous CD45.2 CD4$^+$CD25$^+$CD103$^+$ Treg cells was about the same in spleens from vehicle control animals (13.85%) compared to drug treated animals (13.40%). The average of donor CD45.1 CD4$^+$CD25$^+$CD103$^+$ cells for vehicle controls was 29.06% compared to an average of 9.63% in the drug treated animals. The CD103 surface antigen is expressed by activated Treg cells. This indicated that the relative proportion of activated CD45.1 CD4$^+$CD25$^+$ cells was lower in the drug treated animals than in the vehicle controls, which is consistent with inhibition of Treg cell activity for the donor cells in vivo.

Suitable variations of this protocol include (1) the use of a higher number of donor CD4$^+$CD25$^-$ T cells per animal, e.g., 1×10$^6$/animal, 1.5×10$^6$/animal or 2×10$^6$/animal, (2) different daily dosages of the drug, (3) a different route of administration of the drug, (4) a different compound as the drug and (5) inclusion of additional groups of animals, e.g., a group that receives another therapeutic agent such as an antiinflammatory or immune suppressive glucocorticoid such as dexamethasone or cortisol. Some of these variations can apply to the protocols at example 3 or the some of cited references.

Example 21

Increase of CD4$^+$CD25$^+$ T regulatory cells or their activity in vivo. The compound 17α-ethynylandrost-5-ene-3β,7β, 17β-triol was administered to mice essentially as described in a previously described collagen induced arthritis animal model. H. Offner et al., *Clin. Immunol.*, 110:181-190, 2006.

DBA/1 Lac/J mice were used for the study. The mice were obtained from Jackson Laboratories (Bar Harbor, Harbor, Mass.) and housed in accordance with applicable institutional guidelines. Bovine type II collagen (bCII) was used to induce collagen induced arthritis (CIA) by immunizing 8-week-old mice with 200 μg of bCII emulsified 1:1 with CFA containing 200 μg *Mycobacterium tuberculosis* (100 μL; Difco, Detroit, Mich.). The antigen was injected intradermally at the base of the tail. The animals were monitored for 4-7 weeks to observe the onset and progression of the disease post-immunization. The arthritic severity was evaluated with a grading system for each paw according to the following scale: 0=no redness or swelling; 1=slight swelling in ankle or redness in foot; 2=progressed swelling and inflammation and redness from ankle to mid foot; 3=swelling and inflammation of entire foot; 4=swelling and inflammation of entire foot including toes.

After immunization, the mice were treated with the drug at 40 mg/kg/day in vehicle by oral gavage beginning at the start of observable clinical disease (beginning at about 26-27 days after immunization). The vehicle that was used for the protocol was 30% cyclodextrin-sulfobutylether in water. The cyclodextrin-sulfobutylether was obtained commercially (Captisol™ available at cyclexinc.com). The drug formulation was 20 mg drug/mL in the vehicle.

The results obtained from drug treated animals indicated that administration of the 17α-ethynylandrost-5-ene-3β,7β,17β-triol increased the frequency of Foxp3$^+$ and CD4$^+$ Foxp3$^+$ expressing cells in whole splenocytes as shown below.

|  | Vehicle (n = 3) | drug (n = 3) | p value |
| --- | --- | --- | --- |
| Total Foxp3$^+$ | 1.6% ± 0.16 | 2.39% ± 0.16 | 0.00001 |
| CD4$^+$Foxp3$^+$ | 1.1% ± 0.09 | 1.34% ± 0.05 | <0.00001 |

Cell sorter analysis showed an increase in Foxp3+ CD4$^+$ cells in drug treated animals (1.4%) relative to control animals (1.0%). The Foxp3 protein is associated with differentiation or conversion of CD4$^+$CD25$^-$ T cells to CD4$^+$CD25$^+$ Treg cells and an increase in the number of cells expressing Foxp3 indicates increased development of Treg cells from their precursor cells. After immunization, the mice were treated with the drug at 40 mg/kg/day in vehicle by oral gavage beginning at the start of observable clinical disease (beginning at about 26-27 days after immunization). The results obtained from drug treated animals indicated that administration of the 17α-ethynylandrost-5-ene-3β,7β,17β-triol increased the frequency of Foxp3$^+$ and CD4$^+$Foxp3$^+$ expressing cells in whole splenocytes as shown below. Consistent with this was a statistically improved clinical score in the drug treated animals compared to vehicle controls at days 44-49 after immunization. Between days 34-49 the vehicle control animals had a mean clinical score of about 6.8-8 while the drug treated animals had a maximum mean clinical score of about 5 at day 34 with a slow decline to a mean score of about 3 by day 49. These results indicated that the compound slowed the progression of arthritis and reduced its maximum severity compared to vehicle control animals.

Example 22

Synthesis of compounds is described below.

Androst-5-ene-3β,7β,16α,17β-tetrol (7)

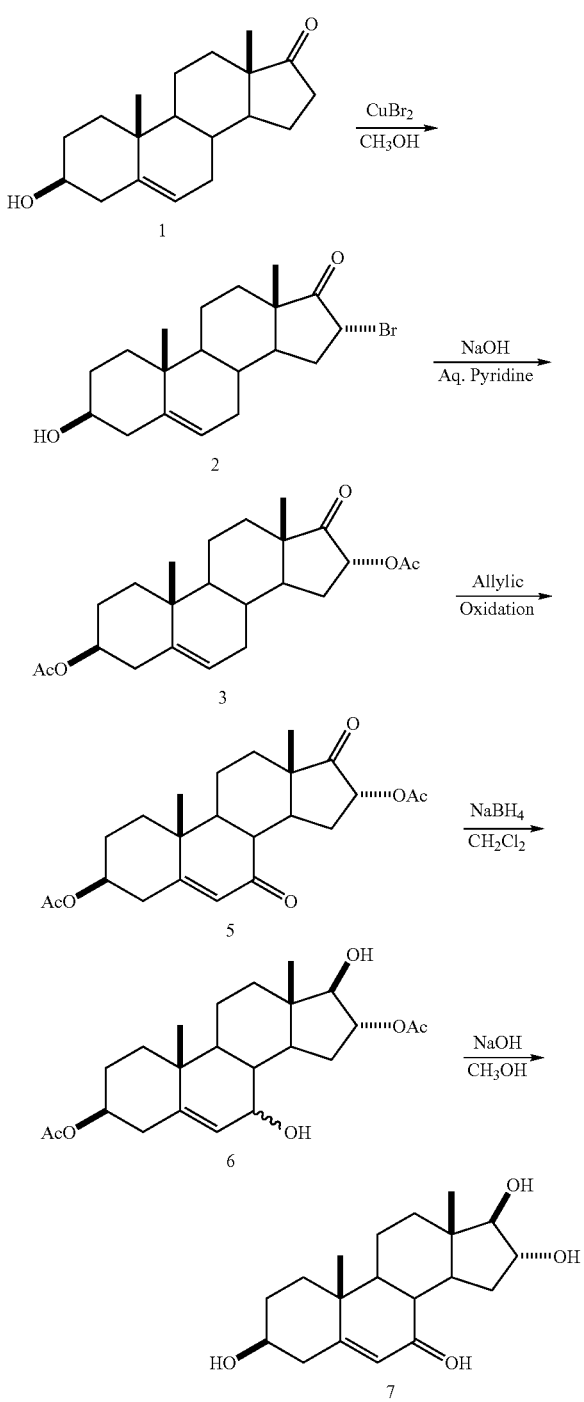

5-androstene-3β,16α-diol-17-one diacetate (3). 16α-bromodehydroepiandrosterone 2 was prepared by refluxing DHEA (1) in methanol with copper (II) bromide. To 15.0 g of 2 (40.8 mmol) in pyridine (129 mL) and water (309 mL) was added 120 mL of 1N aqueous sodium hydroxide and the mixture was stirred in air for 15 minutes. The reaction mixture was poured into ice/water saturated with sodium chloride and containing excess hydrochloric acid. The crude product was filtered, washed with water until neutral and dried in vacuo over anhydrous calcium chloride at 55-60° C. Recrystallization from methanol afforded 8.21 g of 16α-hydroxy-DHEA (Mp 194.4-195.1° C.). This product was then converted to the diacetate 3 by treatment with excess acetic acid in pyridine and purified by flash chromatography.

5-Androstene-3β,16α-diol-7,17-dione (5). To a solution of 3 (20.1 g, 51.7 mmol) in benzene containing celite (60 g) and pyridinium dichromate (75 g) was added 22 mL of 70% tert-butyl hydrogen peroxide. After 2 days of stirring at room temperature, diethyl ether (600 mL) was added and precipitate was filtered and washed with ether (2×100 mL). The residue was purified by flash chromatography (60% ethyl acetate in hexanes) and recrystallized to give 16.0 g (39.8 mmol, 77%) of 5 as prisms. Mp 205.6-206.2° C.

5-Androstene-3β,7β,16α,17β-tetrol (7). To a solution of 5 (10.0 g, 24.8 mmol) in dichloromethane (75 mL) and methanol (255 mL) at 0° C. was added 1.5 g of sodium borohydride and the mixture was stirred at 0° C. for 1 hour. After quenching with acetic acid (3.5 mL) the reaction mixture was partitioned between dichloromethane and water. The organic layer was concentrated to a mixture of 7α and 7β diacetate tetrols. This mixture was purified by flash chromatography and HPLC to give 2.90 g of the 7β-epimer (9.5 mmol, 38%). Mp 216.8-220.8° C. Saponification in methanol (100 mL) with 1N sodium hydroxide (60 mL) for 2 days at room temperature and purification by HPLC gave 7 (1.41 g, 4.4 mmol, 46%) as fine needles from aqueous acetonitrile. Mp 202.1-206.4° C.; [a]D+1.35 (methanol, c=1). Selected $^1$H NMR peaks (CD$_3$OD): d 0.77 (s, 3H), 1.01 (s, 3H), 3.39 (d, 1H), 3.46 (m, 1H), 3.74 (t, 1H), 4.04 (m, 1H), 5.55 (dd, 1H).

3α,7α,17β-Triacetoxyandrost-5-ene-16α-ol (8), androst-5-ene-3α,7α,16α,17β-tetrol (9)

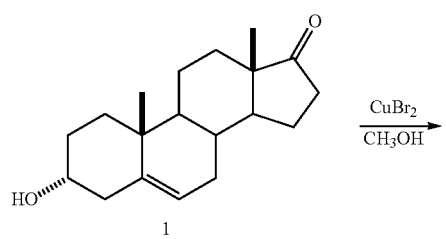

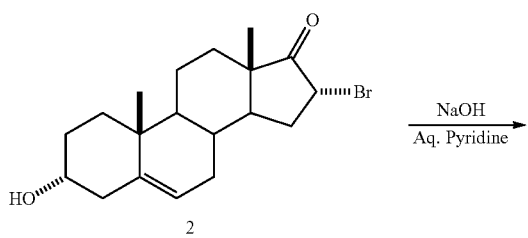

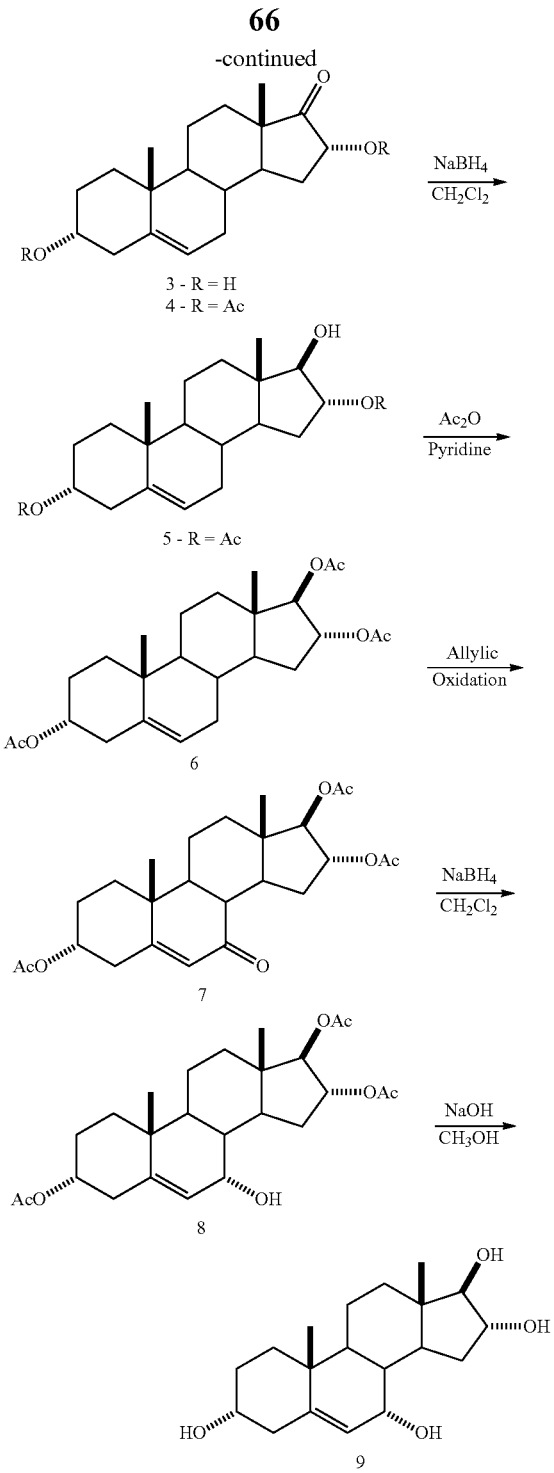

16α-Bromo-5-androstene-3α-ol-17-one (2). A solution of 5-dehydroandrosterone (1) (17.8 g, 61.7 mmol) in methanol (1.35 L) was refluxed with copper (II) bromide (36.4 g, 163 mmol) with stirring for 19 hours. To the cooled reaction mixture was added water (1.35 L) and dichloromethane (1.5 L). The organic layer was filtered through anhydrous sodium sulfate and the product crystallized as fine needles from methanol (16.7 g, 45.5 mmol, 74%). Mp 195-207° C.

3α,16α-Diacetoxy-5-androsten-17-one (4). To a solution of 2 (12.0 g, 32.7 mmol) in pyridine (1.032 L) and water (0.247 L) in air was added aqueous 1N sodium hydroxide (90 mL) and the mixture was stirred at room temperature for 15 minutes. The reaction mixture was added to an ice/water mixture containing 1.2 L of 1N hydrochloric acid. After saturating the solution with sodium chloride, it was extracted with ethyl acetate (2×1 L). The combined organic layers were washed with brine (250 mL), filtered through anhydrous sodium sulfate and concentrated. The crude 5-androstene-3α,16α-diol-17-one (3) was treated with excess acetic anhydride in pyridine at room temperature overnight and purified by column to give 4 (7.46 g, 19.2 mmol, 59%) as prisms from methanol. Mp 172.7-173.7° C.

5-Androstene-3α,16α,17β-triol 3,16-diacetate (5). To a solution of enediolone diacetate 4 (7.46 g, 19.2 mmol) in dichloromethane (45 mL) and methanol (120 mL) at 0° C. was added sodium borohydride (950 mg). The solution was stirred at 0° C. for 1 hour. After addition of excess acetic acid the reaction mixture was partitioned between dichloromethane and water. The organic layer was filtered through anhydrous sodium sulfate and concentrated to yield a mixture of the 17α (minor) and 17β (major) epimers. This mixture was purified by flash chromatography (25% ethyl acetate in hexanes) to give 6.1 g (15.6 mmol, 81%) of the 17β epimer 5. Mp 126.9-128.6° C. The triacetate 6 was made from 5 treated with excess acetic anhydride in pyridine at room temperature overnight and was purified by column to give 6.0 g (13.9 mmol, 89%).

5-Androstene-3α,16α,17β-triol-7-one triacetate (7). A solution of the triacetate 6 (6.0 g, 13.9 mmol) in benzene (255 mL) was treated with celite (25.5 g), pyridinium dichromate (31.5 g) and 70% tert-butyl hydrogen peroxide (9.0 mL) and stirred at room temperature for 19 hours. Anhydrous diethyl ether (255 mL) was added and reaction mixture was cooled in an ice bath for 1 hour. The resulting solid was filtered off and washed with ether (2×50 mL). The combined organic portions were concentrated and purified by flash chromatography (29% ethyl acetate in hexanes) to give 3.45 g of 7 (7.7 mmol, 55%).

5-Androstene-3α,7α,16α,17β-tetrol (9). To a solution of 7 (3.45 g, 7.7 mmol) in dichloromethane (15 mL) and methanol (30 mL) at 0° C. was added sodium borohydride (1.0 g) and the solution was stirred at 0° C. for 2 hours. After addition of excess acetic acid (1.5 mL) the reaction mixture was partitioned between dichloromethane and water. The organic layer was filtered through anhydrous sodium sulfate and concentrated to yield a mixture of the 7α (minor) and 7β (major) epimers. This mixture was saponified in methanol (100 mL) with 1N sodium hydroxide (60 mL) overnight at room temperature. The crude tetrols were recovered by partitioning the saponification mixture between ethyl acetate and brine. The epimers were separated by HPLC to give 220 mg of 9 (0.68 mmol, 9%). Mp 243-248.3° C.). Selected $^1$H NMR peaks (CD$_3$OD): δ 0.77 (s, 3H), 1.02 (s, 3H), 2.11 (m, 1H), 2.57 (m, 1H), 3.34 (s, 1H), 3.44 (d, 1H), 3.70 (brt, 1H), 4.04 (m, 2H), 5.55 (dd, 1H). The epimers of 8 are separated by HPLC to obtain purified 8 and its 7β-acetete epimer.

Androst-5-ene-3β,7β,11β,17β-tetrol-3β-acetate (8), androst-5-ene-3β,7β,11β,17β-tetrol (9), androst-5-ene-3β,7β,17β-tetrol-3β-acetate-11-oxime (10)

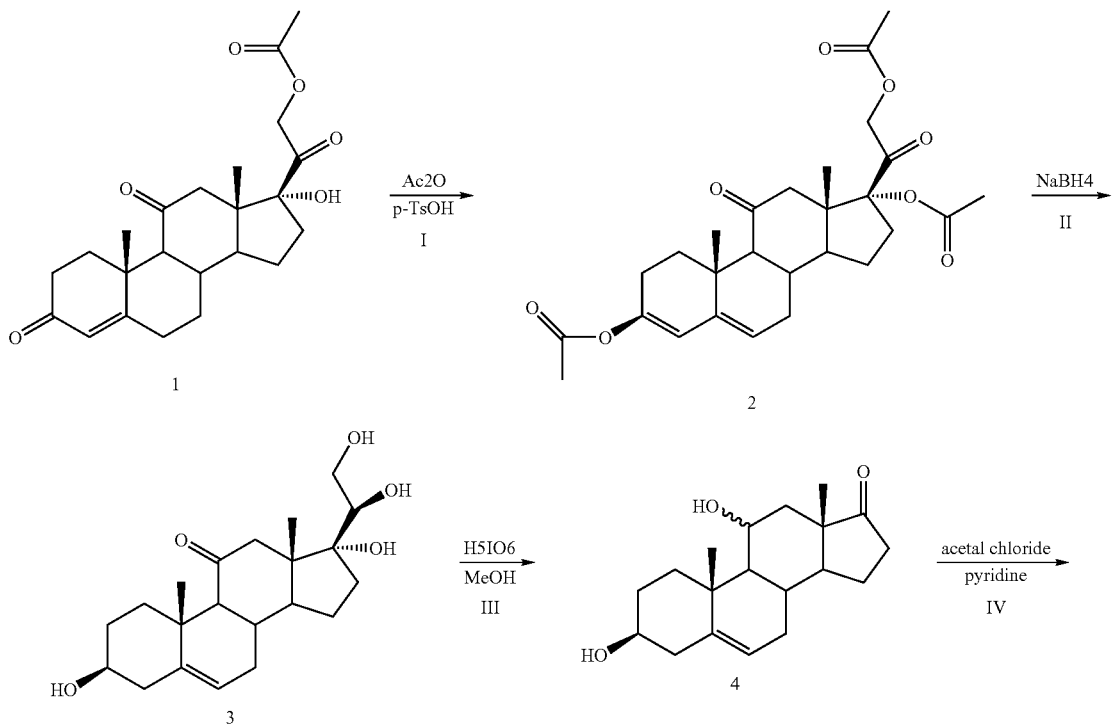

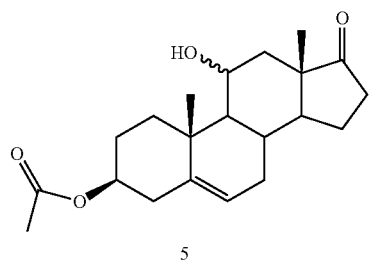
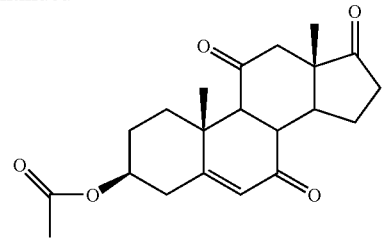
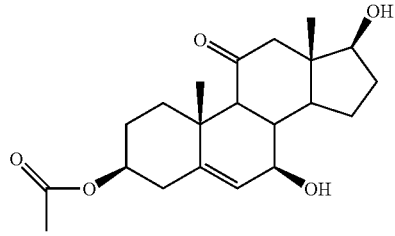
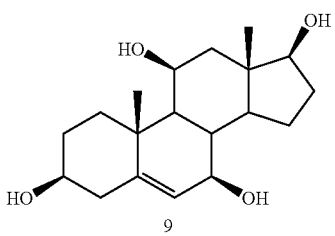

I: To a solution of 1 (4 g) in 150 ml Ac$_2$O, was added p-TsOH 2.8 g, at room temperature, overnight, work up with adding 700 mL ice water, stirring for 1 hr until solid formed, filtered out to yield white solid product 2, 4.55 g II: To a solution of 1.5 g NaBH4 in 35 ml EtOH and 5 ml MeOH, was slowly added a solution of 2 (1.2 g) in 30 ml EtOH and 10 ml chloroform at 0° C. The solution was continued with stirring for 2 hrs at 0° C., then at room temperature 2 hrs. After this time 4 ml acetic acid was added to quench NaBH4, then 50 ml water. The product was isolated by extracting with EtOAc 50 ml×3, removal of solvent in vacuo to yield crude product. Purification was accomplished via column chromatography to yield 3, 250 mg.

III: To a solution of 3 (200 mg) in 8 ml MeOH, was added a solution of 0.36 g H5IO6 in 2 ml water, stirring for 1 hr at room temperature, removal of solvent in vacuo, addition of water and dicholormethane extraction. Purification used column chromatography to yield product 4, 60 mg.

IV: To a solution of 4 (0.4 g) in 5 ml pyridine was added 0.5 ml acetetyl chloride, slowly at 0° C., stirring continued for 15 min at 0° C., then room temperature for 30 min. The reaction was quenched by adding 20 ml water, extraction with EtoAc 15 ml×3, washing with 1N HCl, saturated NaHCO3, brine, then dries over Na2SO4. Concentration in vacuo gave a yield of 5, 520 mg.

V: To a solution of 5 (0.5 g) and 0.13 g CuI in 15 ml acetonitrile, was added 3 ml 70% t-BuOOH slowly, stirring for 1 hr then 50° C. for 2 hrs. Add 12 ml 10% Na2S2O5 solution, extract with EtOAc, dry over Na2SO4, remove solvent, run column to yield 6, 80 mg.

VI: To a solution of 6 (50 mg) in 1.5 ml THF and 3 ml MeOH, was added 260 mg CeCl3.7H2O, then added 75 mg NaBH4 slowly at 0° C., stirring for 30 min, add 0.5 mL 1N HCl and 5 ml water, extract with EtOAc 5 ml×3, dry over Na2SO4, remove solvent to yield 7, 49 mg.

VII: To a solution of 300 mg NaBH4 in 4 ml EtOH and 1 ml MeOH, was added a solution of 7 (40 mg) in 0.5 ml EtOH and 0.5 ml chloroform, stirring for 8 hrs at 0° C., then in a freezer overnight. Add acetic acid to quench reaction, add water and EtoAc extraction to yield 8, 30 mg. mp>250° C.; $^1$H NMR (CD$_3$OD) δ 0.86 (s, 3H), 1.35 (s, 3H), 1.95 (s, 3H), 3.55 (t, 1H, J=7.5 Hz), 3.71 (dd, 1H, J=7 Hz, J=2.5 Hz), 4.32 (d, 1H, J=2.7 Hz), 4.55 (m, 1H), 5.21 (s, 1H)

VIII: To a solution of 8 (30 mg) in 1 mL MeOH, was added a solution of 50 mg NaOH in 0.25 mL water. Stirring for 15 min at 50° C., then add 1N HCl 1 mL, water 5 mL, EtOAc 5 mL×3 to extract, remove solvent to yield 9, 20 mg. mp 170-172° C.; $^1$H NMR (CD$_3$OD) δ 0.95 (s, 3H), 1.32 (s, 3H), 3.41 (m, 1H), 3.51 (t, 1H, J=8.0 Hz), 3.78 (dd, 1H, J=7.1 Hz, J=2.5 Hz), 4.31 (d, 1H, J=2.5 Hz), 5.15 (s, 1H)

IX: To a solution of 29 mg NH$_2$OH.HCl and 17 mg NaOH in hot 1 mL EtOH, was added a solution of 9 (50 mg) in hot 1 mL EtOH, refluxing for 2 hrs at 100° C., filtered out salt, recrystallized in EtOH/H$_2$0 to yield 10, 40 mg. mp>250° C.; $^1$H NMR (CD$_3$OD) δ 0.72 (s, 3H), 1.02 (s, 3H), 2.03 (s, 3H), 3.86 (t, 1H, J=8.5 Hz), 4.08 (dd, 1H, J=8.0 Hz, J=2.6 Hz), 4.60 (m, 1H), 5.19 (s, 1H)

17α-Methylandrost-5-ene-3β,17β-diol-3β-acetate-7,11-dione (7), 17α-methylandrost-5-ene-3β,7β,17β-triol-3β-acetate-11-one (8), methylandrost-5-ene-3β,7β,17β-triol-11-one (9)

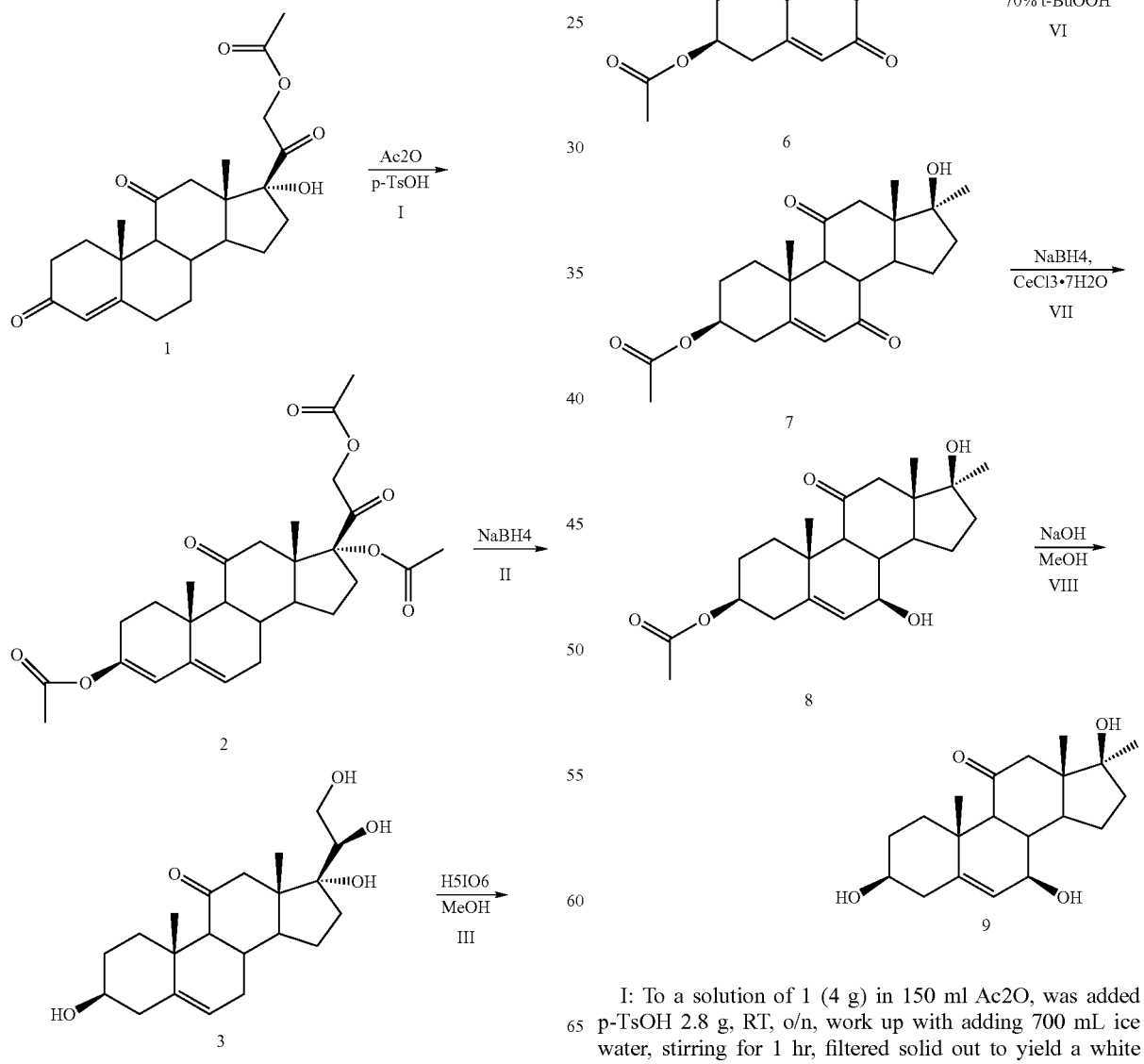

I: To a solution of 1 (4 g) in 150 ml Ac2O, was added p-TsOH 2.8 g, RT, o/n, work up with adding 700 mL ice water, stirring for 1 hr, filtered solid out to yield a white product 2, 4.55 g.

II: To a solution of 1.5 g NaBH$_4$ in 35 mL EtOH and 5 mL MeOH, was added a solution of 2 (1.2 g) in 30 mL EtOH and 10 mL chloroform at 0° C., slowly, continued to stir for 2 hrs at 0° C., and RT 2 hrs, added 4 mL acetic acid to quench NaBH$_4$, add 50 mL water, extracted with EtoAc 50 mL×3, then removed solvent to yield crude product. Column yield 3, 250 mg.

III: To a solution of 3 (200 mg) in 8 ml MeOH, was added a solution of 0.36 g H5IO6 in 2 ml water, stirred for 1 hr at RT, removed solvent, add water and DCM extraction, then ran column to yield product 4, 60 mg.

IV: To a solution of 4 (250 mg) in 1.5 mL THF and 3.5 mL ether at −78° C. under N$_2$, was added 1 mL 22% MeMgCl in THF slowly, stirring for 1.5 hrs at −78° C., then RT for 1 hr, then refluxed for 1 hr at 75° C. Added 4 mL 1N HCl and 10 mL water at 0° C. EtoAc extraction, removed solvent to yield crude 249 mg. Column run yielded 5, 46 mg.

V: To a solution of 5 (1.0 g) in 15 mL pyridine was added 1.1 mL acetic chloride slowly at 0° C., stirring for 15 min at 0° C., then RT for 30 min. add 50 mL water, extracted with EtoAc 50 mL×3, washed with 1N HCl, Sat NaHCO3, brine and dried over Na$_2$SO$_4$. Solvent removal yielded 6, 1.02 g.

VI: To a solution of 6 (1.0 g) and 0.3 g CuI in 40 mL acetonitrile, was added 6 mL 70% t-BuOOH slowly, stirring for 1 hr at RT then at 50° C. for 2 hrs. Added 24 mL 10% Na$_2$S$_2$O$_5$ solution, extracted with EtoAc, dry over Na$_2$SO$_4$, removed solvent, ran column to yield 7, 285 mg. mp>250° C.; $^1$H NMR (CD$_3$Cl) δ 0.82 (s, 3H), 1.29 (s, 3H), 2.05 (s, 3H), 4.70 (m, 1H), 5.75 (s, 1H)

VII: To a solution of 7 (45 mg) in 1.5 mL THF and 3 mL MeOH, was added 150 mg CeCl$_3$.7H$_2$0, then added 30 mg NaBH$_4$ slowly at 0° C., stirring for 10 min, add 0.5 mL 1N HCl and 5 mL water, extracted with EtoAc 5 mL×3, dried over Na$_2$SO$_4$, removed solvent to yield 8, 41 mg. mp 108-110° C.; $^1$HNMR (CD$_3$OD) δ 0.725 (s, 3H), 1.25 (s, 3H), 2.01 (s, 3H), 4.02 (dd, 1H, J=8.2 Hz, J=2.4 Hz), 4.53 (m, 1H), 5.29 (s, 1H)

VIII: To a solution of 8 (22 mg) in 1 mL MeOH, was added a solution of 23 mg NaOH in 0.1 mL water. Stirred for 10 min at 50° C., then added 1N HCl 1 mL, water 5 mL, EtoAc 5 mL×3 to extract. Removed solvent to yield 9, 10 mg. mp>250° C.; $^1$H NMR (CD3OD) δ 0.75 (s, 3H), 1.24 (s, 3H), 3.41 (m, 1H), 3.99 (dd, 1H, J=8.2 Hz, J=2.5 Hz), 5.23 (s, 1H)

17α-Ethynylandrost-5-ene-3β,7β,16α,17β-tetrol (8),
17β-ethynylandrost-5-ene-3β,7β,16α,17α-tetrol (9)

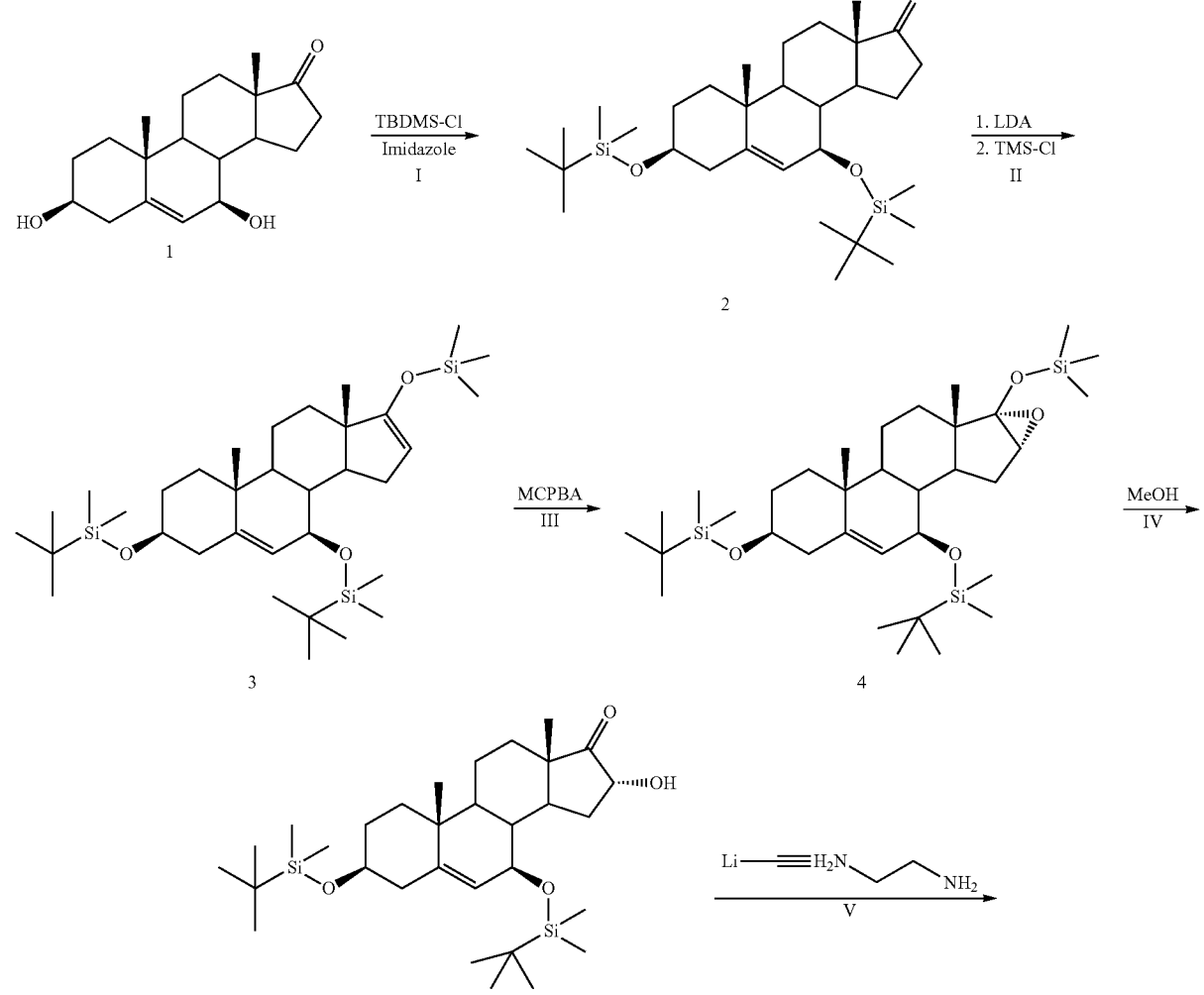

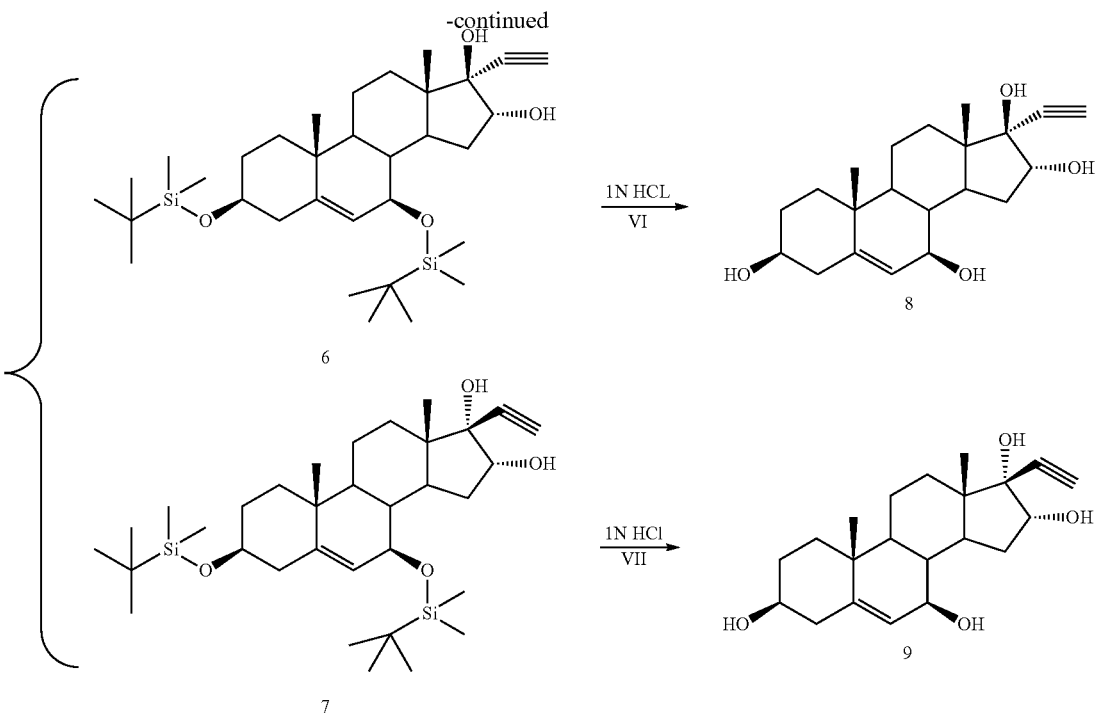

I: To a solution of 1 (1.0 g) and 0.56 g imidazole in 15 ml DMF, was added TBDMS-Cl 1.24 g, RT, o/n, work up with adding 50 ml water, solid show up, filtered out to yield white solid product 2, 1.75 g.

II: To a solution of 2 (1.64 g) in 50 ml THF cooled to −78° C., was added 2.3 ml LDA, 30 min later, was added 0.62 ml TMSCl slowly, stirring for 30 min at −78° C., then warm up to RT stirring for 1 hr, TLC shows RXN was completed, extraction with ether 150 ml×2, washed with water and brine, dried over Na2SO4 to yield yellow product 3, 1.87 g.

III & IV: To a solution of 3 (10 g) in 250 ml THF cooled to −20° C., was added m-CPBA 4.2 g, stirring for 3 hrs to form 4, then add 250 ml MeOH slowly, stirring for 30 min at −20° C., then adding 200 ml Na2SO3 solution slowly at −20° C., stirring for 1 hr. Warm up to RT, extract with ether 150 ml×3, washed with Sat NaHCO3, brine, dry over Na2SO4 to yield crude 11 g, in order to remove some extra m-CPBA in the product, run short column, 100% Hex 50 ml×5, then 50% Hex/EtoAc 100 ml×5 to collect crude product 5, 8.5 g.

V: To a solution of 10 g 90% lithium acetylide ethylene diamine complex in 250 ml dry THF, was added a solution of 5 (5 g) in 50 mL dry THF by syringe pump, which took about 8 hrs. Let it stir for o/n at RT. Added 500 mL water at 0° C., extracted with EtoAc 150 mL×3, washed with 200 mL 0.1N HCl, 150 mL saturated NaHCO$_3$, 100 mL brine, dry over Na$_2$SO$_4$, remove solvent to yield crude 5.5 g, run column to collect two isomers, 17-β-OH, 6 (1.5 g) and 17-α-OH, 7 (1.2 g).

VI: To a solution of 6 (265 mg) in 4 mL MeOH and 3 mL THF, was added 4 mL 1N HCl at RT, 1.5 hrs. Added 10 mL saturated NaHCO$_3$, removed organic solvent at RT, added 10 mL water, stored in freezer o/n to remove water, added THF to the solid, filtered, removed THF to yield a white solid product 8, 130 mg. mp 214-216° C.; $^1$H NMR (CD$_3$OD) δ 0.92 (s, 3H), 1.06 (s, 3H), 2.99 (s, 1H), 3.42 (m, 1H), 3.72 (dt, 1H, J=7.2 Hz, J=2.5 Hz), 4.17 (dd, 1H, J=8.2 Hz, J=2.7 Hz), 5.24 (d, 1H, J=1.0 Hz).

VII: To a solution of 7 (500 mg) in 8 mL MeOH and 6 mL THF, was added 8 mL 1N HCl at RT for 1.5 hrs. Added saturated NaHCO$_3$ to neutralize the solution pH=8. Added 50 ml water to obtain a white solid, filtered, washed with water, dried over vacuum to yield the white solid product 9, 225 mg. mp>250° C.; $^1$H NMR (CD$_3$OD) δ 0.90 (s, 3H), 1.06 (s, 3H), 2.75 (s, 1H), 3.42 (m, 1H), 3.72 (dt, 1H, J=7.0 Hz, J=2.0 Hz), 4.37 (dd, 1H, J=8.1 Hz, J=2.6 Hz), 5.24 (t, 1H, J=2.0, J=1.0 Hz).

4β-Acetylandrost-5-ene-3β,16α,17β-triol (7), androst-5-ene-3β,4β,16α,17β-tetrol (compound 8)

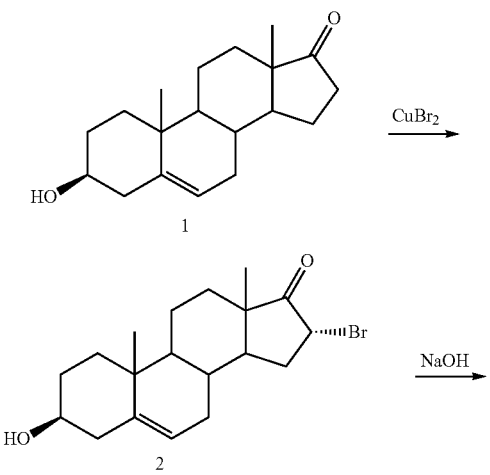

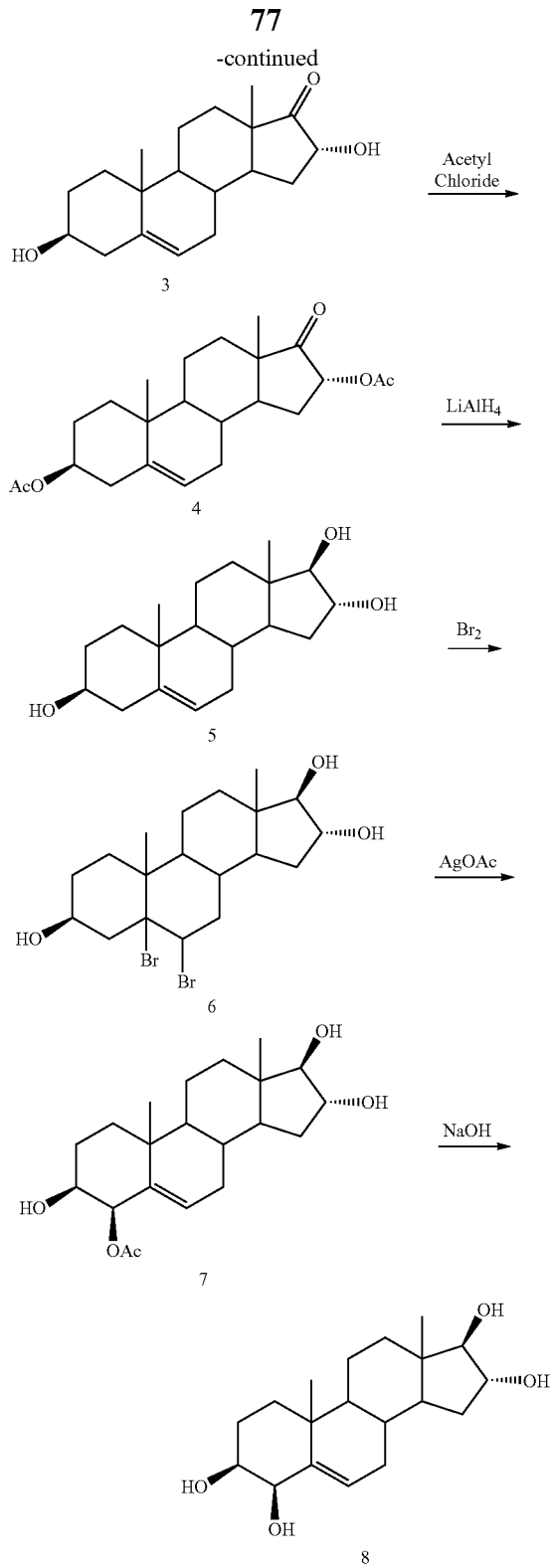

Step 1: A mixture of compound 1 (24.0 g, 0.0832 mol) and copper bromide (56.0 g, 0.20 mol) in anhydrous methanol (800 mL) was refluxed for 16 hr. Most of solvent was removed under vacuum and water (500 mL) was added. The resulting precipitate was collected by filtration and washed with water. The solid was recrystallized in methanol twice to afford compound 2 as a pale yellow solid (19.7 g)

Step 2: To a stirring solution of compound 2 (22.0 g, 0.060 mol) in 200 mL N,N-dimethylformamide was added 1 N sodium hydroxide aqueous solution (66 mL, 0.066 mol). The reaction mixture was stirred at room temperature for 1 hr. 1N aqueous hydrochloric acid (8 mL) and 400 mL water were added. The resulting precipitate was collected by filtration and washed with water. Purification of this crude product by recrystallization from methanol to afford compound 3 as a white solid (11.8 g).

Step 3: To a solution of compound 3 (11.8 g, 0.0387 mol) in pyridine (50 mL) was added acetyl chloride (11.8 g, 0.128 mol) at 0° C. The reaction mixture was stirred at 0° C. for 1 hr. The resulting mixture was warmed up to room temperature and stirred for another 1 hr. Water was added. The precipitate was collected by filtration and washed with water. The solid was dried over vacuum to give compound 4 (12.6 g) which was carried on without further purification.

Step 4: Lithium aluminum hydride (1.13 g, 0.030 mol) was added to a cold (0° C.) solution of compound 2 (3.10 g, 0.00916 mol) in 80 mL of anhydrous ether under nitrogen. The ice bath was removed and the resulting mixture was stirred at room temperature for 0.5 h and then refluxed for 1 h. The reaction was quenched by the addition of 6 N aqueous hydrochloric acid. Ether was removed under reduced pressure. The resulting solid was filtered and washed with water. The crude product was recrystallized in methanol to afford compound 5 (1.1 g) as a white solid.

Step 5: To the solution of 5 (914 mg, 2.98 mmol) in 20 mL of chloroform was added bromine (303 mg, 3.16 mmol). The reaction mixture was stirred at room temperature for 20 min. Solvent was removed in reduced pressure to give compound 6 which was carried on without further purification.

Step 6: Preparation of 4β-acetylandrost-5-ene-3β,16α,17β-triol (7). Compound 6 was dissolved in 30 mL of anhydrous ether and 10 mL of anhydrous pyridine. A solution of silver acetate (1.03 g, 1(914 mg, 2.98 mmol) in 5 mL of anhydrous pyridine was added. The reaction mixture was stirred under dark for 0.5 hr. A heavy greenish precipitate was deposited. Ether (50 mL) was added and precipitate was filtered off. The filtrate was under vacuum to dryness. The residue was purified by flash chromatograph on silica gel eluted with 50:50 ethyl acetate:hexanes to afford the title compound 7 (124 mg) as a white solid. Selected $^1$H NMR data: (CD$_3$OD, 300 MHz): δ 5.78 (d, 1H, J=2.2 Hz), 5.34 (br, 1H), 4.02 (t, 1H, J=4.5 Hz), 3.52 (dt, 1H, J=7.7 Hz, 3.0 Hz), 3.37 (d, 1H, J=4.9 Hz), 2.03 (s, 3H), (1.12 (s, 3H), 0.75 (s, 3H). Melting Point: 152-153° C.

Step 7: Preparation of androst-5-ene-3β,4β,16α,17β-tetrol (8). The compound 7 (50 mg, 0.137 mmol) was dissolved in 1 N sodium hydroxide aqueous (1 mL) and methanol (5 mL) and the resulting solution was refluxed for 1 hr. Methanol was removed under vacuum and the residue was extract with ethyl acetate (3×30 mL). The combined extracts were dried over magnesium sulfate, filtered, and concentrated under vacuum to afford a solid. The crude product was purified by recrystallization from methanol to afford title compound 8 ((23 mg) as a white solid. Selected $^1$H NMR data: (CD$_3$OD, 300 MHz): δ 5.62 (d, 1H, J=3.2 Hz), 4.05 (d, 1H, J=2.4 Hz), 4.02 (m, 1H), 3.43 (dt, br, 1H, J=11.7 Hz, 3.6 Hz), 3.36 (d, 1H, J=4.2 Hz), 1.197 (s, 3H), 0.76 (s, 3H). Melting Point: 238-241° C.

Androst-5-ene-3β,4β,7β,17β-tetrol (12) (method 2), androst-5-ene-3β,3β,7β,17β-triacetoxy-4β-ol (11)

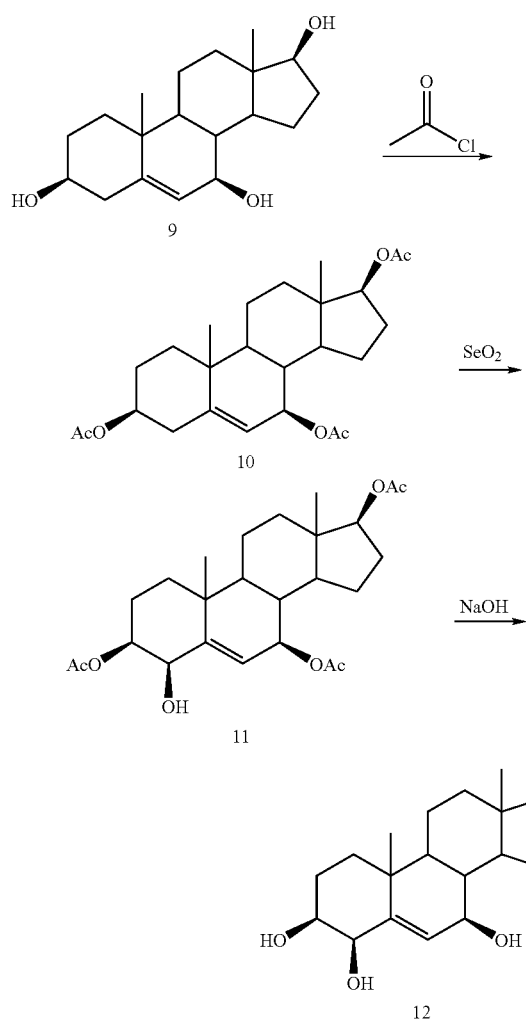

Step 1: To a solution of compound 9 (5.0 g, 0.0138 mol) in pyridine (20 mL) was added acetyl chloride (11.8 g, 0.128 mol) at 0° C. The reaction mixture was stirred at 0° C. for 5 hr then most solvent was removed under vacuum. The residual sludge was partitioned between ethyl acetate (80 ml) and water (20 ml). The organic layer was washed with 1N aqueous hydrochloric acid, saturated sodium bicarbonate aqueous solution then dried over magnesium sulfate, filtered, and evaporated to a solid. The crude product was recrystallized from ethyl acetate and hexane to afford compound 10 (4.8 g) as white solid.

Step 2: To a solution of compound 10 (720 mg, 1.66 mmol) in dioxane (15 mL) and acetic acid (10 mL) was added selenium dioxide (185 mg, 1.66 mmol) in water (1.5 mL) and dioxane (5 mL). The reaction mixture was heated at 95° C. for 36 hr. The mixture was cooled to room temperature, diluted with ethyl acetate, and washed sequentially with water, saturated sodium bicarbonate, and brine then dried over magnesium sulfate, filtered, and concentrated under vacuum to dryness. The crude product was purified by flush chromatograph on silica gel elute with 3:2 hexane:ethyl acetate to afford compound 11 (174 mg) as a white solid.

Step 3: The compound 11 (148 mg, 0.33 mmol) was dissolved in 1 N sodium hydroxide aqueous (3 ml) and methanol (10 ml) and the resulting solution was refluxed for 1 hr. Most of methanol was removed under vacuum. Water was added and mixture was sonicated and filtered. The collected solid was dried over vacuum to afford 12 (82 mg) as white solid. Selected ¹H NMR data: (CD₃OD, 500 MHz) δ 5.48 (d, 1H, J=2.8 Hz), 4.04 (d, 1H, J=2.7 Hz), 3.74 (dd, J=8.3 Hz, J=2.5 Hz), 3.56 (t, 1H, J=8.5 Hz), 3.43 (dt, 1H, J=7.6 Hz, J=4.2 Hz), 1.25 (s, 3H), 0.75 (s, 3H). Melting Point: 144-147° C.

(VI), 16α-bromoandrost-5-ene-3β-ol-11β-acetoxy-17-one (VII), (VIII), androst-5-ene-3β,11β,16α-triacetoxy-17-one (IX), androst-5-ene-3β,11β,16α-triacetoxy-17β-ol (X), androst-5-ene-3β,11β,16α,17β-tetrol (XI)

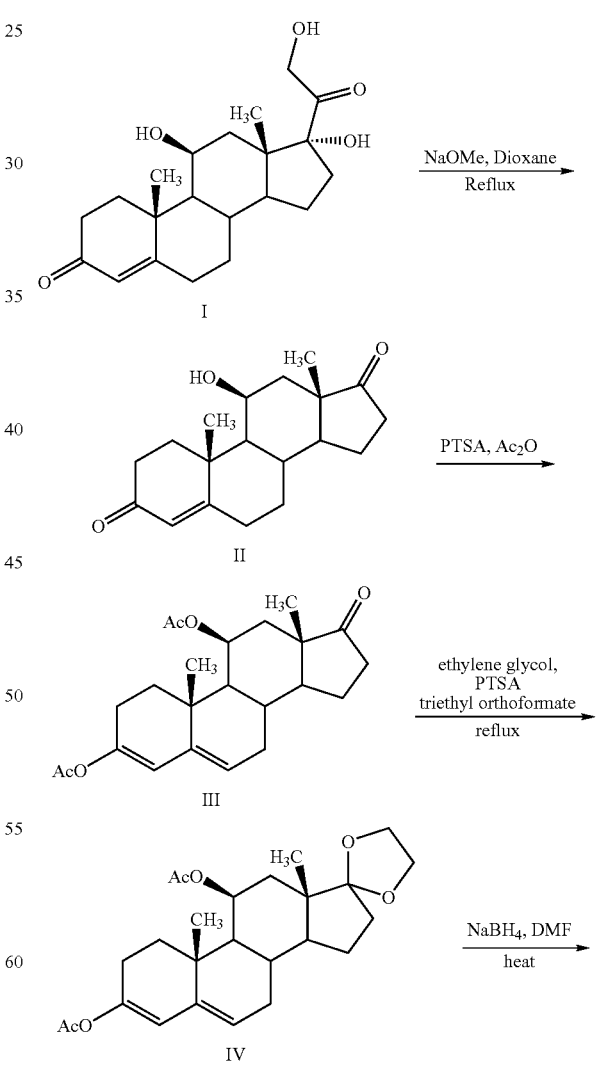

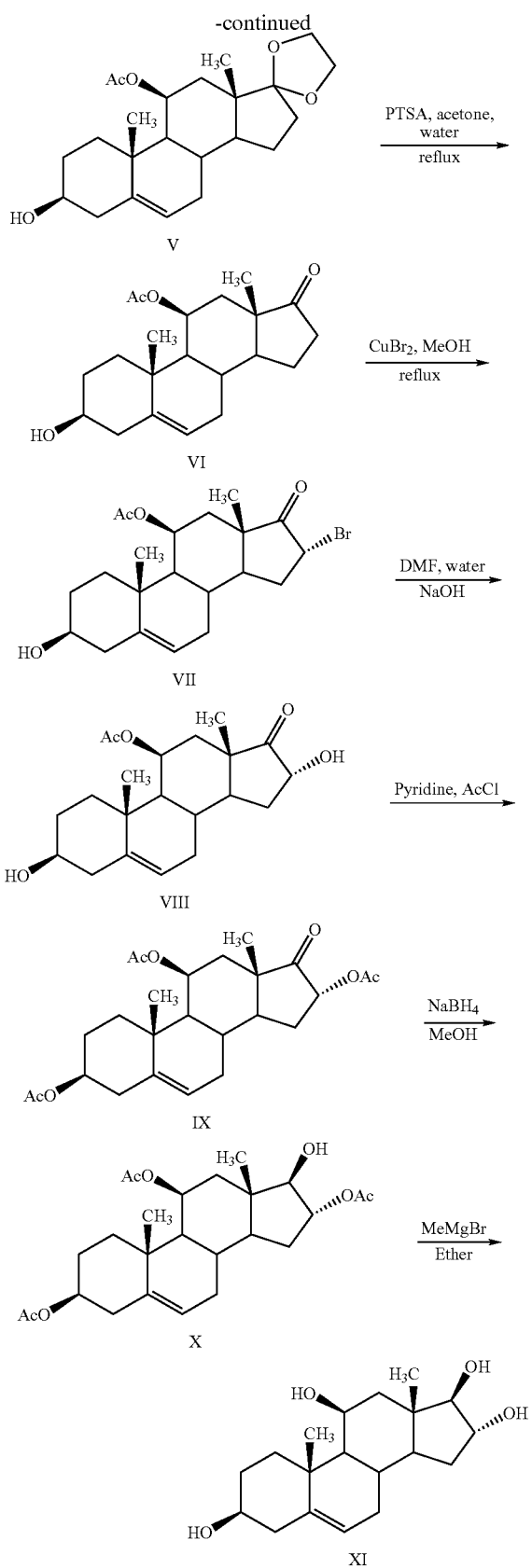

II. Compound I (4.0 g, 11.4 mmol) was dissolved in 100 ml anhydrous 1,4-dioxane. Sodium methoxide (3.0 g, 55.2 mmol) was added and the mixture was refluxed under anhydrous conditions for 3 hours with monitoring by HPLC. Solvent was removed to ⅓ volume and mixture was acidified w/ 2N HCl to pH=5-6. Mixture was extracted with 3×50 ml DCM. Organic layers were recombined and washed with 50 ml sat'd sodium bicarbonate and 50 ml brine. After drying over sodium sulfate and evaporation of solvent, 3.56 g of 95% pure product were isolated.

III. Compound II (13.5 g) and p-toluenesulfonic acid (2.45 g) were stirred for 18 hours in 175 ml anhydrous acetic anhydride. The mixture was then poured into 800 g of ice and stirred for 1 hour. Filtration through a short silica gel plug gave 3.14 g of compound III.

IV. Compound III (100 mg) was dissolved in 1.55 ml ethylene glycol, followed by addition of triethyl orthoformate (3.77 ml) and p-toluenesulfonic acid (50 mg). The mixture was then refluxed for 1.5 hours, and then poured into a hot mixture of 6 ml methanol and 0.08 ml pyridine. The mixture is cooled and 15 ml water was added. The mixture was extracted with 3×30 ml ethyl acetate and washed with sat'd sodium bicarbonate (20 ml) and brine (20 ml)). Drying over sodium sulfate and evaporation of solvent gave 50 mg of 97% pure V.

V. To a solution of 50 mg IV in 2 ml DMF was added a solution of 27 mg sodium borohydride dissolved in 0.5 ml water at room temperature. The solution was heated to 100° C. with vigorous stirring for 15 minutes, followed by cooling to room temperature. The reaction was poured into 18 ml water, followed by 0.2 ml acetic acid. The mixture was extracted with ethyl acetate (2×10 ml) and washed with sat'd sodium bicarbonate (10 ml) and brine (10 ml). Drying over sodium sulfate and evaporation of solvent gave 39 mg of compound V.

VI. Compound V (50 mg) and p-toluenesulfonic acid (2 mg) were suspended in a mixture of 2 ml acetone and 0.21 ml water refluxed for 1.5 hours. After evaporation of acetone, 10 ml water was added and product precipitated out of solution. Filtration gave 42 mg of desired product 95% pure.

VII. Compound VI (315 mg) and $CuBr_2$ (611 mg) were added to 7 ml anhydrous methanol and refluxed for 24 hours. The reaction mixture was then cooled and poured into 15 ml hot water and crude product is filtered off. The crude product was then dissolved in 25 ml methanol/THF (1:1) and then 200 mg activated carbon was added. The solution was boiled for 10 minutes and the carbon was filtered off. The crude product was recrystallized from methanol to give 426 mg product of 75% purity.

VIII. Compound VII (420 mg) was dissolved in a mixture of 18 ml DMF and 7 ml water. Aqueous sodium hydroxide was added while stirring (1N, 1.31 ml). After 10 minutes, solution was poured into an ice/water mixture containing 1.5 ml 1M HCl. The solution was saturated with NaCl and extracted with 2×5 ml ethyl acetate. After drying over sodium sulfate and evaporation of solvent the crude product was purified by column chromatography to give 300 mg of 95% pure VIII.

IX. Compound VIII (300 mg) was dissolved in 6 ml pyridine, followed by addition of 0.34 ml acetyl chloride. The reaction was stirred for 18 hours, and then poured into 30 ml ice water. The crude product was filtered off, then purified by column to give 180 mg pure product.

X. Compound IX (120 mg) was dissolved in 5 ml methanol and cooled in an ice bath. Sodium borohydride (11.5 mg) was added over 5 minutes and the ice bath was removed. After 1 hour the reaction was quenched with 0.2 ml acetic acid and 15 ml water was added. The mixture was extracted with 3×20 ml ethyl acetate and washed with sat'd sodium bicarbonate (20 ml) and brine (20 ml). Drying over sodium sulfate followed by column chromatography gave 86 mg of the desired product.

XI. Compound X (180 mg) was dissolved in 5 ml dry ethyl ether and cooled to −78° C. Methyl magnesium bromide was added dropwise (1.2 ml, 1M in ethyl ether). The reaction was warmed to room temperature, the refluxed for 3 hours. The reaction was then cooled and neutralized with 1M HCl. Precipitated product was filtered off and recrystallized 3 times from methanol/water to give 36 mg of pure XI. Melting point=220.3-221.6° C. Selected NMR shifts: $^1$H NMR (CD$_3$OD): 5.20 ppm (bs, 1H), 4.26 ppm (dd, J=3 Hz, 5 Hz, 1H), 3.88 ppm (m, 1H), 3.32 ppm (m, 1H), 3.19 ppm (d, J=8 Hz, 1H), 1.24 ppm (s, 3H), 0.92 ppm (s, 3H).

Androst-5-ene-3β,16α-diacetoxy-7,17-dione (4), androst-5-ene-3β,16α-diacetoxy-7β,17β-diol (HE3467)

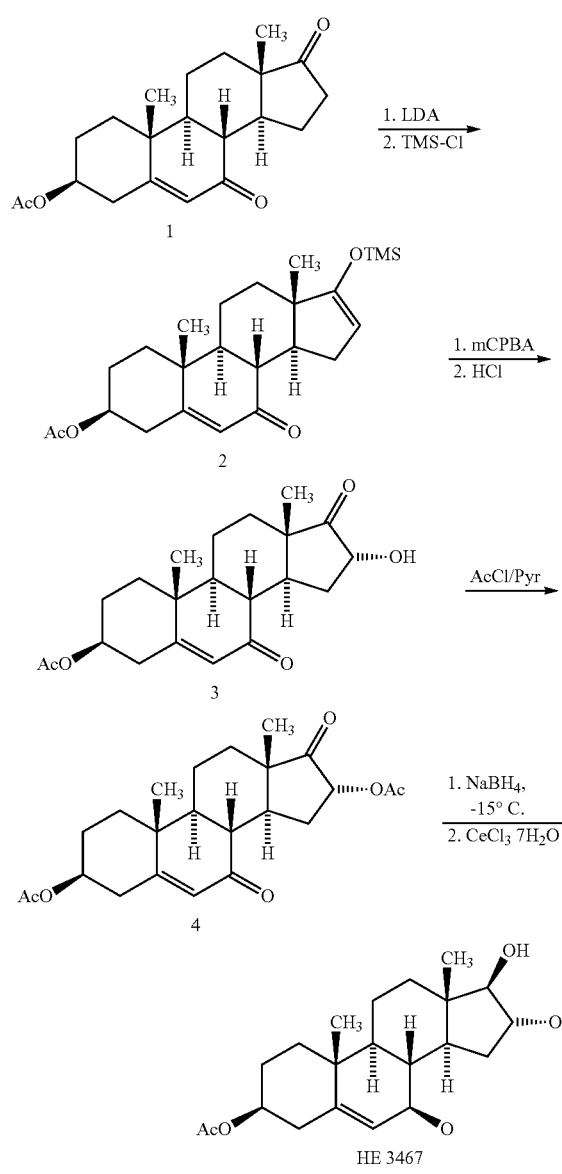

Synthesis of 2. To a solution of 1 (3.44 g, 10 mmol) and TMS-Cl (2.15 ml, 16.5 mmol) in THF (100 ml) cooled to −78° C. was added 2.0 M LDA (7.5 ml, 15 mmol) dropwise. The solution was stirred for 30 min and warmed to room temperature. The reaction mixture was partitioned between 100 ml 1:1 hexane/ether and 100 ml water. The organic layer was washed with brine (3×30 mL) and dried over Na$_2$SO$_4$. A yellow oil was obtained after solvent was removed. The crude was chromatographed silica gel with 5-20% EtOAc/hexane to recover 1.9 g of 1 and 2 as a white solid (600 mg, 1.54 mmol), 31% yield.

Synthesis of 3. To a solution of 2 (100 mg, 0.26 mmol) in THF (3 ml) cooled to 0° C. was added mCPBA (77%, 62.2 mg, 0.27 mmol) and warmed up to room temperature. 0.5N HCl (3 ml) was added and stirred for 20 min, extracted with ether. The extracts were were washed with saturated sodium bicarbonate, brine, dried over Na$_2$SO$_4$. The product 3 was obtained after removing solvent (90 mg, 0.26 mmol), 100% yield.

Synthesis of 4. To a solution of 3 (721 mg, 2.0 mmol) in pyridine (10 mL) cooled to 0° C. was added acetyl chloride dropwise and stirred at 0° C. for 2 hours. The reaction was quenched with water (300 mL) and stirred for 15 min. A solid was formed and collected by filtration. The solid was washed with water, 1N HCl and water, and dried under vacuum to afford an off white solid 4 (737 mg), 90% yield.

Synthesis of HE3467. To a solution of 4 (300 mg, 0.75 mmol) in 1:1 MeOH/THF (15 ml) cooled to −15° C. was added NaBH$_4$ (42.5 mg, 1.12 mmol) over 15 min. A solution of cerium chloride (300 mg, 0.81 mmol) in MeOH cooled −15° C. was added and stirred for 2 min. The reaction was quenched with 1N HCl then poured to 90 mL water. A solid was formed and collected by filtration. The solid was washed with 1N HCl and water, dried under vacuum to afford HE3467 (183 mg, 0.45 mmol), 60% yield. $^1$H NMR (CD3OD): δ 5.29 (s, 1H), 4.89 (m, 1H), 4.55 (m, 1H), 3.74 (d, 1H, J=6.52), 3.60 (d, 1H, J=4.76), 2.36 (d, 2H, J=1.27), 2.15-2.18 (m, 2H), 2.05 (s, 3H), 2.01 (s, 3H), 1.9-1.1 (m, 11H), 1.11 (s, 3H), 0.82 (s, 3H).

5α-Androstane-2β,3α,16α,17β-tetrol (22)

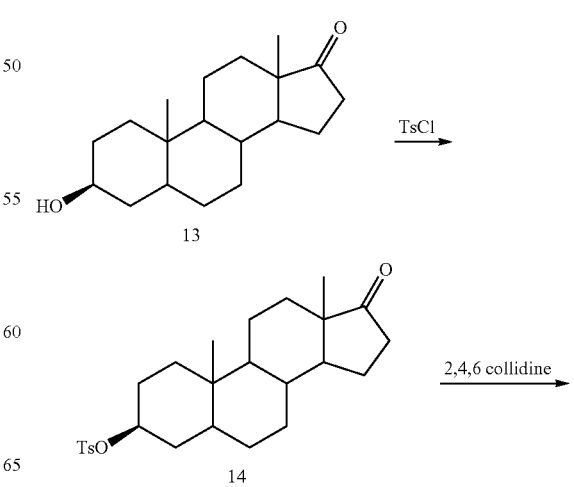

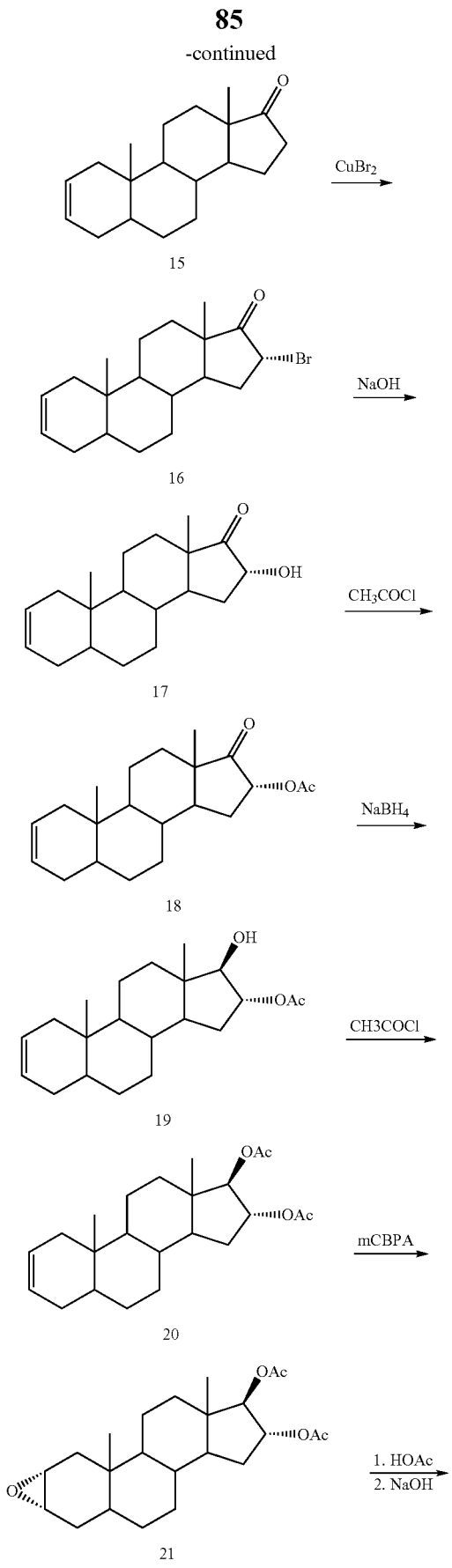

Step 1: To a solution of 13 (50.0 g, 0.172 mol) in pyridine (150 mL) was added p-toluensulfonyl chloride (47.0 g, 0.24 mol) at 0° C. The reaction mixture was stirred at 0° C. for 2 hr and then stirred at room temperature overnight. Water was added. The resulting precipitate was collected by filtration and washed with water. The crude product was purified by recrystallization from methanol to afford 14 (75.2 g) as a white solid.

Step 2: A mixture of compound 14 (75 g, 0.169 mol) in 2,4,6 collidine (200 mL) was refluxed for 5 hr. After cooling, water (500 mL) was added and resulting precipitate was collected by filtration and washed with water. The solid was recrystallized in methanol to give a crude product (42.5 g). The crude product (20.0 g) was dissolved in chloroform (113 mL) and acetic acid anhydride (37 mL). To this solution was added a solution of concentrated sulfuric acid (3 mL) in chloroform (37 mL) and 13 mL acetic acid anhydride at 0° C. The reaction mixture was stirred at 0° C. for 0.5 hr then 700 mL water was added and stirred at room temperature for 6 hours. The resulting precipitate was collected by filtration and washed with water, dried over vacuum to afford 15 (17.2 g) as a white solid.

Step 3: The mixture of 15 (8.17 g, 0.030 mol) and copper bromide (10.8 g, 0.046 mol) in anhydrous methanol (220 mL) was refluxed for 18 hr. After cooling, most of solvent was removed under vacuum and water (150 mL) was added. The resulting precipitate was collected by filtration and washed with water. The solid was recrystallized in methanol to afford 16 as white solid (6.76 g).

Step 4: To the stirring solution of 16 (6.69 g, 0.019 mol) in N,N-dimethylformamide (180 mL) was added 1 N sodium hydroxide aqueous solution (22 mL, 0.022 mol). The reaction mixture was stirred at room temperature for 0.5 hr. 1N aqueous hydrochloric acid (3 ml) and 100 ml water were added. The resulting solution was extracted with ethyl acetate (3×250 mL). The combined extracts were dried over magnesium sulfate, filtered, and concentrated under vacuum to afford 17 (4.37 g) as a waxy solid.

Step 5: To a solution of 17 (3.74 g, 0.013 mol) in pyridine (20 mL) was added acetyl chloride (2.18, 0.028 mol) at 0° C. The reaction mixture was stirred at 0° C. for 1 hr. The resulting mixture was warmed to room temperature and stirred for another 1 hour. Water was added. The precipitate was collected by filtration and washed with water. The solid was dried over vacuum to give 18 (4.25 g) as a white solid.

Step 6: To a solution of 18 (2.4 g, 0.0072 mol) in methanol (80 mL) was added Sodium borohydride (1.2 g, 0.031 mol) at 0° C. The reaction mixture was stirred at 0° C. for 1 hr. The reaction was quenched by the addition of acetic acid (6 mL) and water (15 mL). Most of methanol was removed under reduced pressure. The residual sludge was partitioned between ethyl acetate (80 mL) and water (20 mL). The organic layer was washed with 1N aqueous hydrochloric acid, neutralized with saturated aqueous sodium bicarbonate solution and then dried over magnesium sulfate, filtered, and evaporated to afford crude product 19 (1.92 g) as a white solid.

Step 7: To a solution of 19 (1.9 g, 0.0057 mol) in pyridine (20 mL) was added acetyl chloride (1 mL, 0.014 mol) at 0° C. The reaction mixture was stirred at 0° C. for 1 hr. The resulting mixture was warmed to room temperature and stirred for another 1 hr then most of the solvent was removed under vacuum. The residual sludge was partitioned between ethyl acetate (80 mL) and water (20 mL). The organic layer was washed with 1N aqueous hydrochloric acid, saturated sodium bicarbonate aqueous solution then dried over magnesium sulfate, filtered and evaporated to give a crude product. The crude product was purified by flash chromatography on silica gel and eluted with 1:10 ethyl acetate:hexane to afford the 20 (1.4 g) as a white solid.

Step 8: To a solution of 20 (980 mg, 2.61 mmol) in chloroform (25 mL) was added m-chloroperoxybenzoic acid (3.6 mmol). The reaction mixture was stirred at room temperature for 2 hr. The organic layer was washed with saturated sodium bicarbonate aqueous solution, washed with water and then dried over magnesium sulfate, filtered and evaporated to give a crude product. The crude product was purified by flash chromatograph on silica gel eluted with 1:10 ethyl acetate:hexane to afford 21 (780 mg) as a white waxy solid.

Step 9: The solution of 21 (625 mg, 1.61 mmol) in acetic acid (8 mL) was refluxed for 5 hr. After cooling, the solvent was removed under vacuum to give an oil, which was further dried over vacuum overnight. The resulting waxy solid was dissolved in 2 N sodium hydroxide aqueous (8 mL) and methanol (15 mL) and the reaction was refluxed for 1 hr. Methanol was removed under vacuum and water was added. The resulting precipitate was collected by filtration and washed with water and hot acetone. The collected solid was dried over vacuum to afford androstane-2β,3α,16α,17β-tetrol or 22 (295 mg) as a white solid. Selected $^1$H NMR data: (CD$_3$OD, 500 MHz) δ 3.98 (d, 1H, J=4.8 Hz), 3.79 (br, 1H), 3.74 (br, 1H), 3.35 (d, 1H, 3.6 Hz), 0.99 (s, 3H), 0.77 (s, 3H). mp: 260-263° C.

As will be apparent, the compounds described above can be used to prepare other formula 1 compounds, e.g., other esters or ethers of these compounds. Intermediates in the preparation of the title compounds can also be used in the methods described herein.

Example 23

The capacity of formula 1 compounds to treat multiple sclerosis was evaluated in experimental autoimmune encephalomyelitis (EAE) essentially as described in example 6 above. The protocol for conducting the EAE animal model was described in (D. Auci et. al., *Ann. NY. Acad. Sci. USA*, 1051:730-42, 2005). Female SJL mice (6-8 week old, average body weight of 25 g) obtained from Charles-River were kept under standard laboratory conditions (non specific pathogen germ free) with ad libitum food and water and were allowed to adapt one week to their environment before commencing the study. Animals were randomized into six groups of seven animals each and were (1) mice treated with vehicle, (2) mice treated with SU5416 (Z-3-[(2,4-dimethylpyrrol-5-yl)methylidenyl]-2-indolinone), (3) mice treated with 17β-ethynylandrost-5-ene-3β,7β,17α-triol, (4) mice treated with androst-5-ene-3α, 7β,16α,17β-tetrol, (5) mice treated with androst-5-ene-3β,7β,16α,17β-tetrol, (6) mice treated with 3α-trifluoromethyl-androst-5-ene-3β,17β-diol, (7) mice treated with 17α-trifluoromethyl-androst-5-ene-3β,17β-diol and (8) mice treated with 5α-androstane-3β,17β-diol-16-oxime. EAA was induced with 200 μL of a 1:1 emulsion of 75 μg proteolipid protein (PLP) and 6 mg/mL *Mycobacterium tuberculosis* H37RA in complete Freund's adjuvant (CFA). The 200 μL injection was divided among four sites that drained into the auxiliary and inguinal lymphnodes. Pertussis toxin was used as a co-adjuvant and was administered i.p. at 200 ng/mouse on day zero and day two post immunization. Groups were treated with 0.1 mg of compound in 100 μL vehicle, or with vehicle alone, q.d. po (oral gavage) starting at clinical onset of disease and continuing through to day 30 post immunization. Clinical onset is defined as the time when clinical symptoms of the disease attain a grading between 2-3 in 25% of the mice. Clinical grading was carried out by an observer unaware of the treatment: 0=no illness, 1=flaccid tail, 2=moderate paraparesis, 3=severe paraparesis, 4=moribund state, 5=death. Statistical analysis for significant differences on clinical scores were performed by ANOVA for unpaired data and to the non parametric Mann-Whitney test. A P value <0.05 was considered to be statistically significant. For statistical analysis, the mice that succumbed to EAE were assigned 5 only for the day of death and then were deleted from the experimental group.

As expected, classical signs of EAE developed in 8/8 (100%) of the vehicle-treated mice within day 19$^{th}$ post immunization. The mean day of onset was 15.5±3.9 (SD). In this group of animals the duration of the disease was 12.3±4.3 days. The mean cumulative score from day 1 to 30 was 24.8±7.8 and that from day 31 to day 54 (post treatment) was 22.7±15.8. A course of EAE very similar to that observed in the vehicle-treated mice was observed in the animals treated with SU5416, androst-5-ene-3α,7β,16α,17β-tetrol and 5α-androstane-3β,17β-diol-16-oxime, the so-treated mice exhibiting cumulative incidence of disease, duration of disease and mean cumulative onset comparable to that of the controls. In contrast, the mice treated with androst-5-ene-3β, 7β,16α,17β-tetrol, 3α-trifluoromethylandrost-5-ene-3β, 17β-diol or 17α-trifluoromethylandrost-5-ene-3β,17β-diol exhibited a significantly improved course of EAE as compared to the vehicle-treated mice entailing significantly reduction of both one or more the mean cumulative score and duration. And in further contrast, neither of these 3 compounds significantly influenced the cumulative incidence of EAE or the lethality. Finally, although 17β-ethynylandrost-5-ene-3β,7β,17α-triol only exhibited a trend toward reduced cumulative score and duration vs the vehicle-treated mice, the effects appeared to be biological important (14.9±17.6 and 7±7.9 vs 24.8±7.8 and 12.3±4.3). The lack of statistical significance with this compound is probably due to the large number of mice being assigned score 0 throughout the observation period which therefore resulted in a high standard deviation.

At the end of the treatment on day 30$^{th}$, the mice were monitored for up to additional 24 days. It was possible to observe the disease becoming chronic in the vehicle-treated mice with cumulative scores comparable to that of the treatment period. A substantial increase in the cumulative score during the follow-up period as compared to the treatment period was observed with SU5416 that passed from a mean cumulative score of 25.5±8.9 to 35.5±13.2 and more modestly with 17β-ethynylandrost-5-ene-3β,7β,17α-triol that passed from a mean cumulative score of 14.9±17.6 to 18.4±20.6. In the mice treated with 17β-ethynylandrost-5-ene-3β,7β,17α-triol t it was also possible to observe an increase of the EAE incidence from 57.1% at the end of the treatment period to 85.7% at the end of the follow-up period. On the other hand, the other compounds have appeared to maintain a similar cumulative score in the follow-up period as in the treatment period. This was particularly remarkable for 3α-trifluoromethylandrost-5-ene-3β,17β-diol that passed from a mean cumulative score of 11.2±4.8 during the treatment period to 10.8±10.3 at the end of the follow-up period.

These results show that 17β-ethynylandrost-5-ene-3β,7β, 17α-triol, androst-5-ene-3β,7β,16α,17β-tetrol, 3α-trifluoromethylandrost-5-ene-3β,17β-diol and 17α-trifluoromethyl-androst-5-ene-3β,17β-diol exerted powerful anti-inflammatory properties in the PLP-induced model of EAE in SJL mice. Of particular relevance for the translation of these findings to the clinical setting are the observations that the compounds are active in this EAE model even when given in a protocol starting on day $12^{th}$ post immunization when 24% of the mice had already developed clinical signs of EAE. Of particular note is the finding that SU5416 was ineffective in this setting. It has been previously reported that SU5416 is effective in EAE (L. Bouerat et al., *J. Med. Chem.* 48: 5412-5414, 2005). However, to obtain this result, the SU5416 compound was administered at the same time the animals were immunized. By contrast, in this protocol compounds such as 17β-ethynylandrost-5-ene-3β,7β,17α-triol were not administered to the animals until after disease symptoms were apparent, which shows that the compounds can be used to effectively treat existing disease and to prevent or delay disease onset.

Example 25

Treatment of ionizing radiation exposure. The effect of selected F1Cs on survival of lethally-irradiated female B6D2F1 mice were compared to control animals treated with vehicle alone. The animals were exposed to 10 Gy of total body irradiation at 2.5 Gy/min using a $^{137}Cs$ source. Groups of 12 animals were used in a total of 5 groups. For Groups 1, 2, 3, and 5, test article was administered as a 100 µL volume, by subcutaneous injection, for three consecutive days, with the first dose administered 2 to 4 hours following exposure to radiation. For Group 4, test article was administered as a 50 µL volume, by intramuscular injection for three consecutive days. The formulation was a suspension containing 0.1% w/v carboxymethyl-cellulose, 0.9% w/v sodium chloride and 0.05% v/v phenol. The formulations were agitated to uniformly resuspend the F1C before syringing, and injected into animals within a few minutes of drawing into the syringe to prevent settling in the syringe.

The groups of animals were treated as follows. Group 1 received vehicle only by daily subcutaneous injection for 3 consecutive days. Group 2 received 0.6 mg in 100 µL of a suspension of 3β,17β-dihydroxyandrost-5-ene by daily subcutaneous injection for 3 consecutive days. Group 3 received 3.0 mg in 100 µL of a suspension of 3β,17β-dihydroxyandrost-5-ene by daily subcutaneous injection for 3 consecutive days. Group 4 received 0.6 mg in 50 µL of a suspension of 3β,17β-dihydroxyandrost-5-ene by daily intramuscular injection for 3 consecutive days. Group 5 received 0.6 mg in 100 µL of a suspension of 3β-hydroxy-17β-aminoandrost-5-ene by daily subcutaneous injection for 3 consecutive days. Survival of the animals was monitored for 21 days after irradiation and the following results were obtained. The number of surviving animals is shown for day 6, 7, 12 and 21.

| Group | | Day | | | |
|---|---|---|---|---|---|
| | | 6 | 7 | 12 | 21 |
| 1 | vehicle control | 12 | 11 | 4 | 1 |
| 2 | 0.6 mg s.c. | 12 | 11 | 10 | 7 |
| 3 | 3.0 mg s.c. | 12 | 12 | 9 | 7 |
| 4 | 0.6 mg i.m. | 12 | 12 | 11 | 9 |
| 5 | 0.6 mg s.c. | 12 | 12 | 12 | 11 |

Example 25

Treatment of gastrointestinal inflammation. The capacity of formula 1 compounds to limit or inhibit inflammation or symptoms of inflammation was shown using an animal model for inflammatory bowel disease. Groups of 3 male Wistar rats (180±20 grams) fasted for 24 hours before 2,4-dinitrobenzene sulfonic acid (DNBS) or saline challenge were used. Distal colitis was induced by intra-colonic instillation of 0.5 mL of an ethanolic solution of DNBS (30 mg in 0.5 mL of a 30% ethanol in saline solution) after which 2 mL of air was injected through the cannula to ensure that the solution remained in the colon. The volume used was 0.1 mL per injection of 2 and 20 mg/mL of compound such as androst-5-ene-3β,7β,17β-triol in a liquid formulation, which was administered by subcutaneous injection once a day for 6 days (0.2 mg/animal/day or 2.0 mg/animal/day). The formulation contained 100 mg/mL of compound in a non-aqueous suspension, e.g., 2% benzyl alcohol w/v, 0.1% Brij 96 w/v and equal volumes of PEG 300 and propylene glycol. Concentrations of 2 mg/mL and 20 mg/mL were obtained by diluting the 20 mg/mL formulation with vehicle that lacked compound.

The first dose was given 30 minutes after DNBS challenge. Sulfasalazine (30 mg/mL in 2% Tween 80 in distilled water) was administered orally (PO) once a day (10 mL/kg/day) for 7 days, the first two doses beginning 24 hours and 2 hours before DNBS challenge. The presence of diarrhea was recorded daily by examining the anal area. Animals were fasted for 24 hours prior to being sacrificed. Animals were sacrificed on day 7 or day 8 and their colons are removed and weighed. Before removal of the colon, signs of adhesion between the colon and other organs are recorded. Also, the presence of ulcerations was noted after weighing of each colon. The "net" change of colon-to-body weight (BW) ratio is normalized relative to saline-challenged baseline group. A 25-30% decrease in "net" colon-to-body weight ratio was considered significant. The results showed that androst-5-ene-3β,7β,17β-triol had a modest effect on the course of disease (about 15-20% decrease in net colon-to-body weight ratio), while treatments with 17α-ethynylandrost-5-ene-3β, 7β,17β-triol or androst-5-ene-3β,7β,16α,17β-tetrol were effective (about 25-35% decrease in net colon-to-body weight ratio).

Variations of this protocol include administration of compounds in an aqueous solution of 30% sulfobutylether-cyclodextrin in water using dose levels described above and/or one or more of 0.05 mg/animal/day, 0.1 mg/animal/day, 0.5 mg/animal/day and 1.0 mg/animal/day.

Example 26

Treatment of neuron loss associated with trauma and osteoporosis or bone loss conditions. Immune competence is a complex function that can be acutely impaired following trauma-induced elevations in endogenous glucocorticoid (GC) levels. The compound 5-androstene-3β,7β,17β-triol administered parenterally was used to preserve these immune function by exerting a trophic or anabolic activity. In an animal model of acute cerebral ischemic stroke consecutive to bilateral carotid occlusion in gerbils, treatment with 5-androstene-3β,7β,17β-triol significantly improved cognitive abilities when compared to stroke alone (p=0.03). Thus, the measured food-searching latency period in each group was 6.9±0.9 seconds (sec) for sham, 46.9±13.6 sec for stroke alone and 14.8±4.8 sec for stroke treated with 5-androstene-3β,7β,17β-triol. Concomitantly, the stroke-induced loss in CA1 hippocampal neuron count was markedly abrogated by 5-androstene-3β,7β,17β-triol (sham=362,247±6,839; stroke=152,354±11,575; and stroke+5-androstene-3β,7β,17β-triol=207,854±47,334).

In bone loss conditions, 5-androstene-3β,7β,17β-triol affected the principal bone structures, i.e., cortical and trabecular layers and the growth plate. In thermally-injured mice (20% total body surface area) treated with 5-androstene-3β,7β,17β-triol, loss of cortical (femur) and trabecular/cancellous (tibia) bone mass, as well as suppression of chondrocyte proliferation in proximal tibial epiphyseal growth plate, were all significantly (p<0.01) prevented by 5-androstene-3β,7β,17β-triol treatment. Histomorphometry of the femur cortical bone suggested an increase in bone formation rate. We observed partial protection against loss of bone mineral content as measured by dual X-ray absorptiometry. The femur ash weight was significantly (p<0.01) greater than that in the vehicle-treated burned mice, showing that 5-androstene-3β,7β,17β-triol preserved bone mineral content. Pro-inflammatory effects of chronically high GC levels in brain, suggest that elevated GC levels worsen the outcome of neurological insults. The adrenal steroid DHEA (5-androstene-3β-hydroxy-17-one), an upstream metabolic precursor of 5-androstene-3β,7β,17β-triol, has been demonstrated to prevent dexamethasone-induced thymic involution in mice (K. L. Blauer et al., *Endocrinology*, 129:3174, 1991). Taken together, these findings showed that 5-androstene-3β,7β,17β-triol suppressed GC-induced loss of functional nerve tissue and preserved bone structure after thermal injury.

The capacity of compounds including 5-androstene-3β,7β,17β-triol, 17α-ethynyl-5-androstene-3β,7β,17β-triol and 4-estrene-3α,17β-diol to reverse adverse effects of glucocorticoids in bone growth was shown in the human MG-63 osteosarcoma cell line. MG-63 cells are osteoblasts, which are cells that mediate bone growth. This cell line has been used extensively to study bone biology and to characterize the biological activity of compounds for treatment of bone loss conditions (e.g., B. D. Boyan et al., *J. Biol. Chem.*, 264(20): 11879-11886, 1989; L. C. Hofbauer et al., *Endocrinology*, 140(10):4382-4389, 1999). Adverse toxicities associated with elevated glucocorticoid levels include a decrease in the production of IL-6 and IL-8 by osteoblasts, including the MG-63 cell line, and an increase in the expression of the 11β-hydroxysteroid dehydrogenase type 1 enzyme (11β-HSD). Increased 11β-hydroxysteroid dehydrogenase type 1 enzyme results in increased levels of endogenous glucocorticoid activity by converting endogenous cortisone to the active cortisol, which inhibits bone growth. The 11β-HSD enzyme is expressed in liver, adipose tissue, brain and bone tissues. Cortisol generated by 11β-HSD-1 contributes to osteoporosis, insulin resistance, type 2 diabetes, dyslipidemia, obesity, central nervous system disorders such as stroke, neuron death, depression and Parkinson Disease. Decreases in IL-6, IL-8 and osteoprotegerin are associated with decreased bone growth by osteoblasts. Pilot studies showed that the $IC_{50}$ for inhibition of IL-6 from MG-63 cells by dexamethasone was 10 nM and the $IC_{50}$ for inhibition of growth of MG-63 cells by dexamethasone was 15.3 nM.

In this protocol, MG-63 cells were grown in the presence or absence of the synthetic glucocorticoid dexamethasone at a 30 nM concentration and in the presence or absence of formula 1 compound at 10 nM. Compound 1 in the table below was 5-androstene-3β,7β,17β-triol, compound 2 was 17α-ethynyl-5-androstene-3β,7β,17β-triol and compound 3 was 4-estrene-3α,17β-diol. The results for these compounds are shown below.

| MG-63 growth conditions | IL-6 pg/mL | IL-8 units | 11β-HSD mRNA units | osteoprotegerin pmol/L |
|---|---|---|---|---|
| vehicle control | 6.2 | 0.90 | 0.25 | 445 |
| dexamethasone | 1.3 | 0.12 | 1.0 | 280 |
| compound 1 | 4.0 | 0.53 | 0.73 | — |
| compound 2 | 2.8 | 0.50 | 0.54 | — |
| compound 2 (1 nM) | — | — | — | 455 |
| compound 3 | 4.1 | 0.55 | 0.75 | — |

These results showed that the compounds at 10 nM partially reversed the adverse effects of dexamethasone at 30 nM, which shows that the compounds can reverse multiple toxicities associated with elevated glucocorticoid levels in osteoblasts, which are the cells that mediate bone growth. In a related protocol, the compound 17α-ethynyl-5-androstene-3β,7β,17β-triol at 1 nM also completely reversed the decrease in osteoprotegerin synthesis by MG-63 cells after growth of the cells for 7 hours in the presence of 30 nM dexamethasone as shown in the table above. Osteoprotegerin is a factor associated with bone growth and decreased osteoprotegerin synthesis is associated with bone loss. Other compounds that completely or partially reversed the decrease in osteoprotegerin synthesis by MG-63 cells in the presence of 30 nM dexamethasone were 17α-trifluoromethyl-5-androstene-3β,7β,17β-triol (normal or basal osteoprotegerin levels at 1 μM compound compared to vehicle control with no compound or dexamethasone), 5-androstene-3β,7β,16α,17β-triol (normal osteoprotegerin levels at 0.1 μM), 3β,7α,16α,17β-tetrahydroxyandrost-5-ene (near normal osteoprotegerin levels at 10 nM), 3α,7β,16α,17β-tetrahydroxyandrost-5-ene (normal osteoprotegerin levels at 10 nM), 17α-methylandrost-5-ene-3β,17β-diol-7-one (increased osteoprotegerin levels at 100 nM), 17α-methylandrost-5-ene-3β,7β,17β-diol (normal osteoprotegerin levels at 10 nM). Other compounds that partially reversed the decrease in osteoprotegerin in the presence of 30 nM dexamethasone included androst-5-ene-3β,17β-diol-7-oxime.

In similar protocols the compound 3α,17β-dihydroxyandrost-4-ene showed statistically significant reversal of dexamethasone-induced suppression of IL-8 and IL-6 by MG-63 cells and a decrease in dexamethasone induced 11β-HSD mRNA.

To show that relevant effects could be obtained in vivo, the compound 17α-ethynyl-5-androstene-3β,7β,17β-triol was administered to mice that were also treated daily with dexamethasone for 23 days to reduce levels of osteoprotegerin in the animals. Osteoprotegerin levels in mice that were treated with vehicle and dexamethasone at 10 μg/day (positive control group) had 3.3 pMol/L osteoprotegerin, while animals treated with vehicle, dexamethasone and 17α-ethynyl-5-androstene-3β,7β,17β-triol at 4 mg/kg/day had 6.4 pMol/L osteoprotegerin (p<0.05).

The degree of apoptosis of osteoblasts and osteocytes in murine vertebral bone as a function of estrogen deficiency was examined. Swiss Webster mice (four months old) were ovariectomized. Twenty-eight days later, the animals were sacrificed, vertebrae were isolated, fixed and embedded, and then undecalcified in methacrylate. The prevalence of osteoblast and osteocyte apoptosis was determined by the TUNEL method with $CuSO_4$ enhancement, and was found to be increased following loss of estrogen. Treatment with a reference compound such as 17β-estradiol and with F1Cs such as 4-estrene-3α,17β-diol and or 17α-ethynyl-5-androstene-3β,7β,17β-triol were found to reduce apoptosis, which is consistent with reduced lone loss.

Collectively, the results described in this example are evidence that compounds such as 17α-ethynyl-5-androstene-3β,7β,17β-triol affect bone tissue by both increasing bone growth and by inhibiting bone loss. Compounds such as 17α-ethynyl-5-androstene-3β,7β,17β-triol and 5-androstene-3β,7β,16α,17β-tetrol do not interact with androgen receptor, estrogen receptor-α or estrogen receptor-β, which is consistent with their capacity to treat bone loss conditions without exerting unwanted sex hormone activity.

Example 27

A thermal injury model using mouse ear tissue was used to characterize compounds for their capacity to treat inflammation associated with thermal trauma. The conditions were the minimal burn injury which progressed to tissue necrosis in the exposed ear of untreated mice by 24-72 hours post-burn. Groups of Balb/c mice, approximately nine weeks old were given an identifying mark and then divided into control and treated subgroups. The thickness of the ear to be immersed in hot water was recorded, and then the entire ear of the anesthetized mouse was dipped into 52° C. water for 24 seconds. Each mouse was returned to its cage after an injection of either the propylene glycol vehicle (control) or 100 mg of compound in propylene glycol. Ear swelling changes were monitored on individual mice at pre-burn, and at various times after thermal injury. Ear swelling changes were monitored on individual mice at pre-injury and at 1, 3, 6, 9, 12, 18, 24 and 48 hours after thermal injury. Animals were treated with 100 mg of dehydroepiandrosterone (DHEA) dissolved in propylene glycol. Analysis of edema formation and resolution in control and DHEA-treated mice showed peak ear swelling, as a measure of edema, in both DHEA-treated and untreated burned mice at six hours after injury.

In the untreated control group, the extent of swelling started to decline within 12 hours, and continued to decline rapidly over the subsequent 12 hour periods. Between 24 and 48 hours post-burn, ear tissue showed loss of from the microvascular occlusion of the original zone of stasis. The compounds androst-5-ene-3β,17β-diol and 16α-bromodehydroepiandrosterone protected treated animals against much of the ischemic consequences of thermal injury to the ear. The compounds 16α-hydroxydehydroepiandrosterone was less protective, i.e., it reduced the extent of, but did not totally prevent progressive ischemia, and 16α-chlorodehydroepiandrosterone was only slightly protective against progressive ischemia.

The effect of compounds on hemorrhagic shock and ischemia was examined in another protocol. CF-1 mice at an age of 6-8 months were anesthetized using methoxyfluorothane and prepared for abdominal surgery. Each mouse was tested for the level of respiration, eye blink response and response to a skin pinch to ensure a level of anesthesia appropriate for surgery. The duration of abdominal surgery was approximately two hours, during which time 35-40% of the animal's blood volume is removed over a 30-minute period. The removal of blood in a controlled manner simulates the effect of hemorrhagic shock. A slow intravenous infusion of the removed blood and a 2× volume of resuscitation fluid (lactated Ringers solution) into a central vein was made. The resuscitation fluid was supplemented with either 2 mg dehydroepiandrosterone-3β-sulfate or the excipient as a placebo. The peritoneum and overlying skin were sutured separately. Animals were maintained at 38°-39° C. until recovery is complete. Under these conditions, most of the placebo-treated animals died within 24-48 hours. Four hours after surgery, a colony forming unit (CFU) assay for bacteria was performed and malondialdehyde in liver was assayed using conventional techniques. Mesenteric lymph nodes (MLN) were removed and cultured on blood agar plates and the number of CFUs counted following culturing. The liver was removed and the amount malondialdehyde was measured. Treatment with dehydroepiandrosterone-3β-sulfate resulted in survival of 15/15 mice while 1/15 vehicle control animals survived.

The effect of treatment in a rat model of hemorrhagic trauma was examined. Twenty-four rats were subjected to 40% loss of total blood volume, consisting of catheterization and laparotomy (soft tissue injury) to mimic trauma and hemorrhage. One hour after onset of hemorrhage, the animals were resuscitated with crystalloid fluid and packed red blood cells (PRBCs). Twelve animals received one subcutaneous injection of androst-5-ene-3β,7β,17β-triol in a methyl cellulose suspension at a concentration of 40 mg/kg body weight in 100 μL/kg body weight, one hour after initiation of hemorrhage, but prior to fluid resuscitation. Twelve animals received subcutaneous methyl cellulose control injection at 100 μL/kg body weight. Three days after induction of hemorrhage, the twelve animals that received androst-5-ene-3β,7β,17β-triol had a 100% survival rate; whereas the mortality rate was 25%, in the untreated group (P<0.04, Barnard's unconditional test of superiority using difference of two binomial proportions).

A reduced blood pressure hemorrhagic trauma protocol was also conducted as a second model of hemorrhagic trauma. In this protocol, 15 rats were hemorrhaged described above to a mean arterial pressure of about 35-40 mmHg and resuscitated one hour from onset of the hemorrhage with crystalloid and PRBCs. Seven animals received one animals received one subcutaneous injection of androst-5-ene-3β,7β,17β-triol in a methyl cellulose suspension at a concentration of 40 mg/kg body weight in 100 μL/kg body weight, one hour after initiation of hemorrhage, but before fluid resuscitation. Eight animals received subcutaneous methyl cellulose control injection at 100 μL/kg body weight. Two days after induction of hemorrhage, mortality in the untreated group (n=8) was 75%. The mortality rate in the androst-5-ene-3β,7β,17β-triol-treated animals was 43%, demonstrating that the compound was protective in cases of hemorrhagic trauma where blood pressure was reduced.

Example 28

Metabolic stability. The metabolic stability of selected compounds was examined in vitro using microsomes obtained from liver tissue according to the following protocol. Microsomes in this protocol are capable of hydroxylation reactions and redox reactions that interconvert hydroxyl and ketones on the steroid molecules. Microsomes do not mediate conjugation reactions, e.g., sulfation of 3β-hydroxyl groups or glucuronidation of 3α-hydroxyl groups.

The protocol was performed as follows. (1) Prepared 0.5 mM compound in acetonitrile/water 35:65. For androst-5-ene-3β,17β-diol, prepared 0.145 mg/mL, or 29.0 μL of a 1 mg/mL stock plus 171 μL solvent. For the standard curve dilutions of the 0.5 mM stock was used to obtain final concentrations of androst-5-ene-3β,17β-diol at 10 μM, 5 μM and 1 μM. (2) Set up samples as follows. Each assay consisted of an androst-5-ene-3β,17β-diol control and 1-8 unknown compounds. Tubes for each compound was follows: 1-0' 2-0' 3-0' 4-0'*5-0'*6-5 μM 7-1 μM 8-30' 9-30' 10-30' where * designated denatured microsome negative control reaction tubes. For additional compounds numbering was started at 11, 21, 31, etc. (3) Added 315 μL PBS (pH 7.3-7.5) to each tube. Added 10 μL of the appropriate test article solution to each tube. (4) The internal standard/acetonitrile solution. (5) The NADPH regenerating system (NRS) was 125 μL per tube. To PBS added 1.7 mg/ml NADP, 7.8 mg/ml glucose-6-phosphate, 6 units/mL glucose-6-phosphate dehydrogenase. Fresh NRS for each experiment was kept on ice until use. (6) Each reaction used 125 μL of NRS in each tube. (7) Removed liver microsome preparation from −80° C. freezer and thawed in a room temperature water bath. The microsomal preparation was at a concentration of 20 mg/ml. Each reaction used 0.25 mg/tube and was diluted to a concentration of 5 mg/ml in PBS (i.e. 4-fold dilution) and kept on ice. (8) For the zero-time and denatured microsome control tubes 500 μL acetonitrile at −20° C. was added. Zero time tubes were transferred to ice and denatured microsome controls were preincubated at 37° C. for 5 minutes. (9) Assay tubes containing the microsomal preparation was also preincubated for 5 min at 37° C. (10) For each incubation tube, the reaction was started by addition of 50 μL of the microsome preparation and vortexing to mix. (11) Each reaction was terminated by adding 500 μL acetonitrile at −20° C. and vortexing. (12) After the reaction was terminated, 100 μL from each reaction tube was transferred to a fresh tube and 200 μL of water and 1400 μL of methyl-t-butyl ether was added to each tube. The tubes were Vortexed and centrifuged at 13,000 rpm for 10 min on a microfuge. The tubes were then put on a dry ice-methanol bath until aqueous layer was frozen solid. (13) The methyl-t-butyl ether was transferred from each tube to a fresh tube and the solvent was evaporated ether under nitrogen and the precipitate was then resuspended in 100 μL acetonitrile/water 35:65 and analyzed by LCMS. Results are shown in the table below for the incubation times shown below.

| Compound | parent remaining human microsomes | parent remaining mouse microsomes |
|---|---|---|
| androst-5-ene-3β,17β-diol | 39% (10 min) | 25% (10 min) |
| androst-5-ene-3β,17β-diol | 30% (90 min) | — |
| androst-5-ene-3β,7β,17β-triol | 86% (90 min) | 89% (10 min) |
| 17α-ethynylandrost-5-ene-3β,7β,17β-triol | — | 86%* (30 min) |
| androst-5-ene-3β,7β,16α,17β-tetrol | 100% (10 min) | 100% (10 min) |
| androst-5-ene-3α,7β,16α,17β-tetrol | 100% (10 min) | 100% (10 min) |
| androst-5-ene-3α,7α,16α,17β-tetrol | 100% (10 min) | 100% (10 min) |
| androst-5-ene-3β,7α,16α,17β-tetrol | 100% (10 min) | 100% (10 min) |

*rat microsome instead of mouse preparation

The results show that the tetrol compounds were resistant to redox reactions, which is consistent with a greatly reduced degree of metabolism compared to the androst-5-ene-3β,17β-diol reference compound. This observation was quite unexpected because each of the four hydroxyl groups could potentially be reduced to a ketone, but none was in fact affected. Other compounds that were examined included androst-5-ene-3β,16α,17β-triol, androstane-3β,16α-diol-17-one and androstane-3α,16α,17α-triol, all of which were metabolized by microsomes at a rate similar to the androst-5-ene-3β,17β-diol reference compound.

Example 29

Measurement of drug absorption with CaCo-2 cells. This protocol was used to measure the influx of compounds across a CaCo-2 cell monolayer. CaCo-2 cells are human cells with a polarized, highly differentiated cell line demonstrating an intestinal absorptive cell phenotype (J. Hunter et al., *J. Biol. Chem.*, 268(20):14991-14997, 1993). This cell line is used to study the rate at which various compounds cross the cell monolayer. Typically, confluent monolayers of Caco-2 cells are used to model the intestinal epithelium and to obtain permeability coefficients from the steady-state flux of test compounds. This can provide information about a compound's potential to be orally bioavailable.

In this protocol, the cells were maintained in medium at 37° C., using 100 μL per well of warm medium in a sterile 50 ml tube. The cells were grown on sterile 24-well plates with 600 μL of differentiation medium per well. The wells contained a transwell insert to allow two compartments per well. 100 μL of differentiation medium was carefully added into each well, touching the pipette tip to the side of well. Cells were incubated at 37° C., 5% $CO_2$, saturating humidity for 48 hours to form a monolayer. For each plate, tubes were numbered with tubes 1-24 for basolateral buffer to serve as a basolateral zero time point ($T_o$). Tubes 26 to 49 were apical buffer containing test article to serve as apical $T_o$. Tubes 51-74 were the $T_{20}$ time point (20 minute), 76-99 were the $T_{40}$ time point, 101-124 were the $T_{80}$ time point, 126-149 were the $T_{120}$ time point, and 151-174 were $T_{120}$ apical samples for mass balance determination. Tubes 175-179 were the 5-point standard curve for Compound 1, tubes 180-184 were the standard curve for Compound 2 and so on to tubes 230-234 for Compound 12. Tubes 1-49 were placed in 4 rows in rack 1, 51-99 in rack 2, 101-149 in rack 3, 151-174 in rack 4, and 175-234 in racks 5 and 6.

Buffers were prepared by removing 150 mL of transport buffer from a fresh 1000 mL bottle (at pH to 7.4 with 1 N HCl). This buffer is 'basolateral'. The pH of the remaining 850 mL was adjusted to 6.5 with 1 N HCL for the 'apical' buffer. 150 mL of apical buffer was placed in a separate vessel, and the remaining 700 mL was used the for rinsing. Buffers were stored at 4° C. but used at room temperature for the protocol.

After differentiation medium reached room temperature, about 20 mL was poured into a small beaker. The probe was equilibrated in this medium for 15 min. 24-well plates were removed from the incubator and allowed to reach room temperature. Each well was measured by the probe by inserting the probe into the well without touching the cell monolayer; press the TEST button when the probe is close to the medium surface and the reading will go from 0000 to a number when the probe touches the surface; a reading >1000Ω was acceptable. The apical buffer was then decanted from the transwell insert and the entire plate was rinsed in a 1000 mL beaker containing rinse buffer to remove all differentiating buffer. The transwells were then placed into the T20 plates. 10 μM of test compound and controls (carabamazepine MW 236; hydrochlorothiazide MW 351) was added in apical buffer by adding 0.1 μmol (e.g. 29 μl of a 1 mg/ml androst-5-ene-3β, 17β-diol reference solution) to 10 mL of apical buffer. 0.6 mL of basolateral buffer was then added to all wells.

A solution of 50 μg/ml 3α,7β,16α,17β-tetrahydroxyandrost-5-ene as an internal standard was made by adding 150 μL of the compound (1 mg/mL in ethanol) to 10 mL acetonitrile/water (25:75). Standard curves were made in basolateral buffer for each compound. The 10 μM apical buffer was diluted six fold when passing into the basolateral compartment, so the standard curve was prepared at a six fold lower concentration.

| Concentration | Apical TA (10 μM) | Baso Buffer |
|---|---|---|
| 2 μM | 120 | 480 |
| 1 μM | 60 | 540 |
| 0.5 μM | 30 | 570 |
| 0.2 μM | 12 | 588 |
| 0.05 | 3 | 597 |

600 μL of basolateral buffer was placed in tubes 1-24 for the $T_o$ controls. 100 μL of apical buffer plus test article plus 500 μl apical buffer (so that concentration will be in standard curve range) was added to tubes 26-49 to serve as apical $T_o$. Place 100 μl apical buffer plus compound on the apical side. The time that the transwell was placed in the plate was taken as time zero ($T_o$). At T=20, the transwells were moved to the T40 plate and 600 μL of sample from the T20 plate was added to the appropriate tube. At T=40, the transwell was moved to the T80 plate and 600 μl of sample was taken from the T40 plate to the appropriate tube. At T=80, move the transwell to the T120 plate. Pipette 600 μl of sample from the T80 plate to the appropriate tube and so on for the remaining time points. 100 μL of the apical buffer was added to the appropriate tube for mass balance. Samples will immediately extracted immediately were placed in a freezer.

300 μL of each sample was transferred from the assay tube into a labeled 2 mL tube, except for tubes 151-174 (which contained only 100 μL); 50 μl of these samples were transferred and added to 250 μL of basolateral buffer (resulting in a 6-fold dilution). 20 μL of the 3α,7β,16α,17β-tetrahydroxyandrost-5-ene internal standard was added to each tube and 1500 μL of methyl-t-butyl ether was added to each tube. The tubes were vortexed, centrifuged in a microcentrifuge for 10 min. and placed in methanol/dry ice bath until frozen. Fresh tubes were labeled and the methyl-t-butyl ether was decanted from each frozen tube into the fresh tube. The methyl-t-butyl ether was then evaporated under nitrogen and reconstituted in 120 μL acetonitrile/water (35:65) and analyzed by LCMS. In the table below compound 1 was 3β,7β,16α,17β-tetrahydroxyandrost-5-ene, compound 2 was 17α-ethynylandrost-5-3β,7β,17β-triol, compound 3 was 3α,17β-dihydroxy-17α-ethynylandrostane, compound 4 was 3α,7β,16α, 17β-tetrahydroxyandrost-5-ene, compound 5 was 2β,3α,16α,17β-tetrahydroxyandrostane, compound 6 was 3β,16α-diacetoxy-7β,17β-dihydroxyandrost-5-ene, compound 7 was 3β-acetoxy-17α-ethynylandrost-5-7β,17β-diol, compound 8 was 3β-acetoxyandrost-5-7β,16α,17β-triol and compound 9 was 17α-ethynylandrost-5-3α,7β,17β-triol.

| Compound | Conc. (μM) apical @$T_0$ | Cumulative basolateral conc. (μM) in 80 min | % apical transported in 80 min | Total % transported |
|---|---|---|---|---|
| 1 | 2.195 | 0.017 | 0.008 | 0.8% |
| 2 | 1.911 | 0.470 | 0.246 | 24.6% |
| 3 | 2.727 | 0.411 | 0.151 | 15.1% |
| 4 | 1.664 | 0.019 | 0.012 | 1.2% |
| 5 | 1.817 | 0.162 | 0.089 | 8.9% |
| 6 | 1.776 | 0.185 | 0.104 | 17.8% |
| 7 | 1.710 | 0.195 | 0.114 | 31.4% |
| 8 | 1.724 | 0.123 | 0.071 | 15.9% |
| 9 | 1.773 | 0.531 | 0.299 | 29.9% |

Studies with the CaCo-2 cell line indicated that tetrol compounds such as androst-5-ene-3β,7β,16α,17β-tetrol were not highly permeable and would thus not be expected to be orally bioavailable. Despite that, the compound androst-5-ene-3β, 7β,16α,17β-tetrol was active as described above when administered orally to mice in a diabetes treatment model. Other protocols showed that the degree of sulfation and the degree of glucuronidation for the tetrol compounds such as 3β,7β,16α,17β-tetrahydroxyandrost-5-ene and 3α, 7β,16α, 17β-tetrahydroxyandrost-5-ene was low for tetrol compounds compared to diols. This activity may have arisen at least partly from the low metabolism of tetrol compounds in vivo.

What is claimed is:

1. A method to identify a compound with a potential to treat or ameliorate a metabolic disorder in a mammal, comprising selecting a compound that
    (i) does not activate one, two or three of PPAR-α, PPAR-γ and PPAR-δ in human or mammalian cells in vitro by more than about 30% when compared to suitable negative control human or mammalian cells in vitro;
    (ii) inhibits or decreases the transcriptional activity or level of NF-κB by about 20-80% in human or mammalian cells in vitro when compared to suitable negative control human or mammalian cells in vitro;
    (iii) when compared to a suitable negative control or normal control, (a) decreases the degree of hyperglycemia, (b) slows the progression of hyperglycemia, (c) delays the onset of hyperglycemia, (d) decreases the rate of macular degeneration, (e) delays the onset of macular degeneration, (f) decreases the occurrence or incidence of vascular ulcers, (g) decreases the severity of vascular ulcers, (h) increases insulin sensitivity, (i) decreases glucose intolerance, (j) slows the progression or rate of loss of pancreatic β-islet cell numbers or their capacity to secrete insulin, (k) increases pancreatic β-islet cell numbers or their capacity to secrete insulin, (l) slows the rate of weight increase in db/db mice or mice with diet induced obesity, (m) decreases elevated levels of triglycerides, (n) decreases elevated levels total blood or serum cholesterol, (o) decreases normal or elevated levels of LDL, VLDL, apoB-100 or apoB-48 in blood or serum, (p) increases normal or low levels of HDL or apoA1 in blood or serum, (q) decreases or normalizes an elevated level of a phase reactive protein, optionally C reactive protein or fibrinogen in blood or serum, (r) decreases or normalizes hemoglobin $A_{1C}$, (s) decreases or normalizes fasting blood glucose levels, (t) normalizes serum or blood glucose in an oral glucose tolerance test, (u) normalizes serum or blood glucose in a 2 hour post prandial glucose test or (v) increases whole body or tissue glucose disposal or uptake in a human or another mammal in vivo, for 1, 2 or 3 of the foregoing;

(iv) optionally, does not activate one or more of a glucocorticoid receptor, an androgen receptor an estrogen receptor-α, estrogen receptor-β or a biologically active variant of any of these biomolecules in human or mammalian cells in vitro by more than about 30% when compared to suitable negative control human or mammalian cells in vitro; and (v) optionally inhibits the level or activity of phosphoenolpyruvate carboxykinase (PEPCK) or a 11β-hydroxysteroid dehydrogenase (11β-HSD), optionally 11β-HSD type 1 or 11β-HSD type 2 or the level of a mRNA that encodes PEPCK or a 11β-HSD, in hepatocytes or liver-derived cells in vitro or in liver cells or tissue obtained from liver cells or tissue in vivo; wherein the compound with a potential to treat or ameliorate the metabolic disorder in a mammal is identified and optionally recorded as such in a written or a readable electronic medium.

2. The method of claim 1 wherein the mammal is a rodent, an obese rodent, a human or an obese human.

3. The method of claim 2 wherein the metabolic disorder is type II diabetes, hyperglycemia, elevated nonesterified fatty acids or insulin resistance.

4. The method of claim 3 wherein the compound is selected from formula 1 compounds having the structure

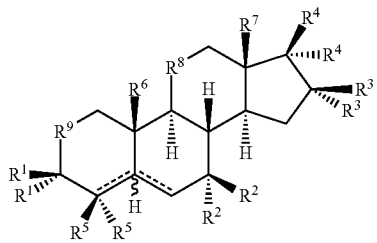

wherein, the dotted lines are optional double bonds or if no double bond is present at the 4-5 or 5-6 positions, then hydrogen is present in the α- or β-configuration;

one $R^1$ is —H or a carbon-linked moiety such as optionally substituted alkyl and the other $R^1$ is an oxygen-linked moiety, a sulfur-linked moiety or a nitrogen-linked moiety, or both $R^1$ together are =O, =NOH or =NO—$C_{1-6}$ alkyl;

one $R^2$ is —H or a carbon-linked moiety such as optionally substituted alkyl and the other $R^2$ is —H, an oxygen-linked moiety, a sulfur-linked moiety or a nitrogen-linked moiety, or both $R^2$ together are =O;

one $R^3$ is —H or a carbon-linked moiety such as optionally substituted alkyl and the other $R^3$ is —H, an oxygen-linked moiety, a sulfur-linked moiety or a nitrogen-linked moiety;

one $R^4$ is —H or a carbon-linked moiety such as optionally substituted alkyl and the other $R^4$ is an oxygen-linked moiety, a sulfur-linked moiety or a nitrogen-linked moiety, or both $R^4$ together are =O, =NOH or =NO—$C_{1-6}$ alkyl;

one $R^5$ is —H or a carbon-linked moiety such as optionally substituted alkyl and the other $R^5$ is —H, an oxygen-linked moiety, a sulfur-linked moiety or a nitrogen-linked moiety, provided that if a double bond is present at the 4-5 position, then $R^5$ is —H, an oxygen-linked moiety, a sulfur-linked moiety or a nitrogen-linked moiety;

$R^6$ is —H or $C_{1-6}$ optionally substituted alkyl, wherein $R^6$ optionally is —$CH_3$; and $R^7$ is —H or $C_{1-6}$ optionally substituted alkyl, wherein $R^7$ optionally is —$CH_3$, —$CH_2OH$ or —$C_2H_5$;

$R^8$ is —$CH_2$—, or —$C(R^{10})_2$— where $R^{10}$ independently or together are —H, =O, a carbon-linked moiety such as optionally substituted alkyl, an oxygen-linked moiety, optionally —OH or an ester or ether optionally selected from —OC(O)—$CH_3$, —OC(O)—$C_2H_5$, —$OCH_3$ and —$OC_2H_5$ in the α- or β-configuration or $R^8$ is a sulfur-linked moiety or a nitrogen-linked moiety optionally selected from —SH, —SC(O)—$CH_3$, —SC(O)—$O_2H_5$, —$SCH_3$ and —$SC_2H_5$ in the α- or β-configuration; and $R^9$ is —$CH_2$—, or —$C(R^{10})_2$— where $R^{10}$ independently or together are —H, halogen, =O, a carbon-linked moiety such as optionally substituted alkyl, an oxygen-linked moiety, optionally —OH or an ester or ether optionally selected from —OC(O)—$CH_3$, —OC(O)—$C_2H_5$, —$OCH_3$ and —$OC_2H_5$ in the α- or β-configuration, or $R^8$ is a sulfur-linked moiety or a nitrogen-linked moiety optionally selected from —SH, —SC(O)—$CH_3$, —SC(O)—$C_2H_5$, —$SCH_3$ and —$SC_2H_5$ in the α- or β-configuration.

5. The method of claim 4 wherein, the oxygen-linked moiety is —OH, an ester, phosphate, a phosphoester, sulfate, a sulfate ester, amino acid, a peptide, an ether, a carbonate, a carbamate, or a polymer, any of which are in the α-configuration or the β-configuration;

the sulfur-linked moiety is —SH, a thioester or a thioether, any of which are in the α-configuration or the β-configuration;

the nitrogen-linked moiety is —$NH_2$, an amino acid, a peptide, a carbamate, an amide, monosubstituted amine or a disubstituted amine, any of which are in the α-configuration or the β-configuration, or the nitrogen-linked moiety is =NOH or =NO—$C_{1-6}$ alkyl, where the amine substitution(s) optionally are optionally substituted alkyl and provided that there is 0 or one =NOH or =NO—$C_{1-6}$ alkyl moieties present; and the carbon-linked moiety is optionally substituted alkyl, acyl or thioacyl optionally selected from the group consisting of =$CH_2$, =CHOH, —$CH_3$, —$CF_3$, —$C_2H_5$, —$C_2F_5$, —CH=$CH_2$, —CCH, —CCOH, —C(O)$CH_3$, —C(O)$CF_3$, —C(O)$CH_2OH$ and —C(O)$CH_2$-halogen.

6. The method of claim 5 wherein the compound has the formula

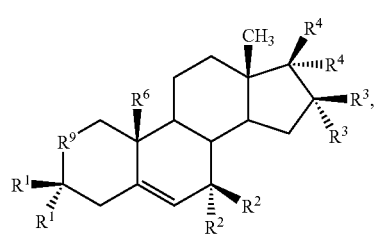

-continued

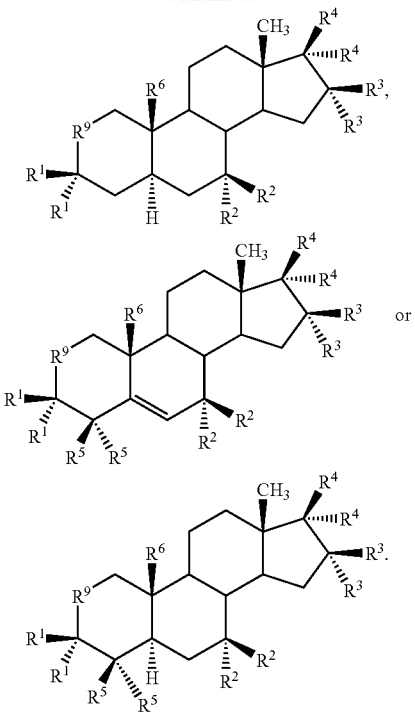

7. The method of claim 5 wherein the compound has the formula

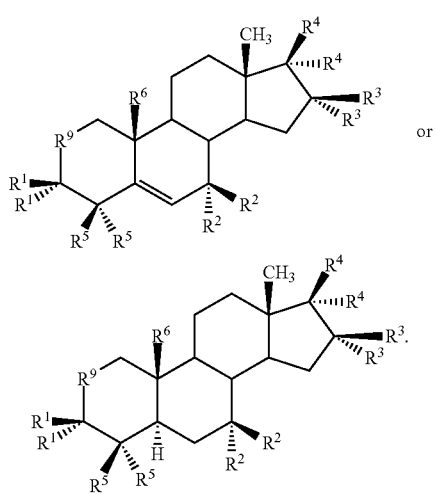

8. The method of claim 5 wherein the compound has the formula

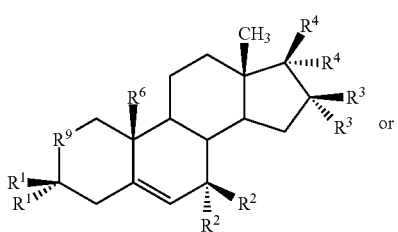

-continued

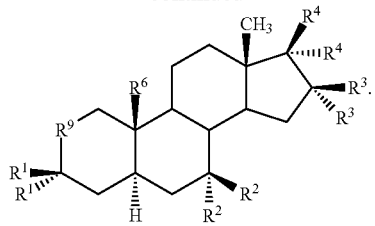

9. The method of claim 5 wherein the compound has the formula

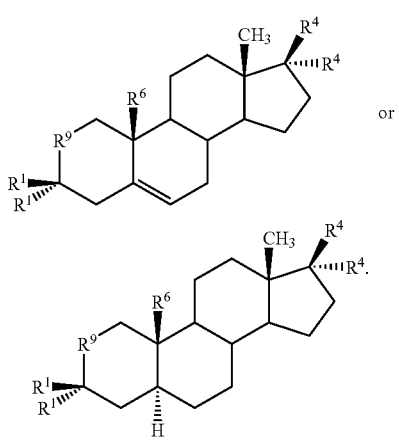

10. The method of claim 4 wherein $R^6$ is —H or —CH$_3$.

11. The method of claim 10 wherein one $R^2$ and $R^3$ is —H, or C1-4 optionally substituted alkyl and the other $R^2$ and $R^3$ is —OH, an ester or an ether, wherein the ester is optionally selected from the group consisting of —O—C(O)—CH$_3$, —O—C(O)—CF$_3$, —O—C(O)—CH$_2$CH$_3$ and —O—C(O)—(CH$_2$)$_2$CH$_3$, and/or wherein one $R^5$ is —H or C1-4 optionally substituted alkyl and the other $R^5$ is —OH, —SH or an ester.

12. The method of claim 11 wherein $R^4$ in the β-configuration is —OH, an ester or an ether and $R^4$ in the α-configuration is or optionally substituted $C_{1-8}$ alkyl optionally selected from the group consisting of —CH$_3$, —CF$_3$, —CN, —C$_2$H$_5$, —C$_2$F$_5$, —CH=CH$_2$, —CCH or both $R^4$ together are =NOH.

13. The method of claim 4 wherein the formula 1 compound is 17α-ethynylandrost-5-ene-3β,7β,16α,17β-tetrol, 17α-ethynylandrost-5-ene-3α,7β,16α,17β-tetrol, 17α-ethynylandrost-5-ene-3β,7β,17β-triol, 17α-ethynylandrost-5-ene-3β,7β,17β-triol, 17β-ethynylandrost-5-ene-3β,7β,17α-triol, 17α-ethynylandrost-4-ene-3β,7β,17β-triol, 17α-ethynylandrostane-3β,7β,17β-triol, 17α-ethynylandrost-5-ene-3α,7β,17β-triol, 17α-ethynylandrost-4-ene-3α,7β,17β-triol, 17α-ethynylandrostane-3α,7β,17β-triol, 17α-ethynylandrost-5-ene-3β,7α,17β-triol, 17α-ethynylandrost-4-ene-3β,7α,17β-triol, 17α-ethynylandrostane-3β,7α,17β-triol, 17α-ethynylandrost-5-ene-3α,7α,17β-triol, 17α-ethynylandrost-4-ene-3α,7α,17β-triol, 17α-ethynylandrostane-3α,7α,17β-triol, 17α-ethynylandrost-5-ene-7β,17β-diol-3-one, 17α-ethynylandrost-5-ene-3β,17β-diol-7-one, 17α-ethynylandrost-5-ene-3α,17β-diol-7-one, 17α-chloroethynylandrost-5-ene-3β,7β,17β-triol, 17α-chloroethynylandrost-5-ene-3α,7β,17β-triol, 17α-ethynylandrost-5-ene-3β,4β,16α,17β-tetrol, 4-acetoxy-17α-ethynylandrost-4-ene-3β,16α,17β-triol, 17α-ethynylandrost-5-ene-3α,4β,16α,17β-tetrol, 4-acetoxy-17α-ethynylandrost-4-ene-3α,16α,17β-triol, 17α-ethynylandrost-5-ene-3β,11β,16α,17β-tetrol, 17α-ethynylandrost-5-ene-3α,11β,16α,17β-tetrol, 17α-ethynylandrost-5-ene-3β,11β,16β,17β-tetrol, 17β-ethynylandrost-5-ene-3β,11β,16β,17α-tetrol, 17α-ethynylandrost-5-ene-2β,3β,16α,17β-tetrol, 17α-ethynylandrost-5-ene-2β,3α,16α,17β-tetrol, 17α-ethynylandrost-5-ene-2α,3β,16α,17β-tetrol, 17α-ethynylandrost-5-ene-2α,3α,16α,17β-tetrol, or an analog of any of these compounds wherein the hydroxyl group at the 3-position, if present, is replaced with an ester, optionally selected from —OC(O)CH$_3$ and —OC(O)C$_2$H$_5$.

14. The method of claim 4 wherein the formula 1 compound is 17α-ethynylandrost-5-ene-3β,7β,17β-triol.

* * * * *